United States Patent
Albany et al.

(10) Patent No.: US 11,896,783 B2
(45) Date of Patent: Feb. 13, 2024

(54) CATHETER HOUSING

(71) Applicant: VASONICS, INC., Corona, CA (US)

(72) Inventors: Ramy Albany, Corona, CA (US); Amid Albany, Beirut (LB)

(73) Assignee: VASONICS, INC., Corona, CA (US)

( * ) Notice: Subject to any disclaimer, the term of this patent is extended or adjusted under 35 U.S.C. 154(b) by 14 days.

(21) Appl. No.: 17/178,779

(22) Filed: Feb. 18, 2021

(65) Prior Publication Data
US 2021/0260342 A1    Aug. 26, 2021

Related U.S. Application Data

(63) Continuation of application No. 16/204,689, filed on Nov. 29, 2018, now Pat. No. 10,960,184, which is a (Continued)

(51) Int. Cl.
*A61M 25/02* (2006.01)
*A61B 5/01* (2006.01)
(Continued)

(52) U.S. Cl.
CPC .............. *A61M 25/02* (2013.01); *A61B 5/01* (2013.01); *A61B 5/021* (2013.01);
(Continued)

(58) Field of Classification Search
CPC .............. A61M 25/02; A61M 25/0097; A61M 2025/0019; A61M 2025/0206; A61M 2025/0246; A61B 5/01; A61F 13/00068
See application file for complete search history.

(56) References Cited

U.S. PATENT DOCUMENTS

| 3,194,235 A | 7/1965 | Cooke |
| 3,900,026 A | 8/1975 | Wagner |
| (Continued) | | |

FOREIGN PATENT DOCUMENTS

| DE | 102016003189 B3 | 4/2017 |
| EP | 2008624 A1 | 12/2008 |
| (Continued) | | |

OTHER PUBLICATIONS

*2019 Top 10 Patient Safety Concerns: Executive Brief*, ECRI Institute, 2019, 19 pages.
(Continued)

*Primary Examiner* — Tasnim Mehjabin Ahmed
(74) *Attorney, Agent, or Firm* — Knobbe, Martens, Olson & Bear, LLP

(57) ABSTRACT

A catheter housing device for securing a catheter and needle assembly to a patient. The device can include a cover, an IV/catheter lock, a hub, and one or more fastening straps. The device can replace conventional devices and techniques for securing a catheter and needle to a patient that utilize adhesive materials and/or methods, which are ill-equipped to solve complications including infection/contamination of the insertion site, irritation/damage to the vein or insertion site due to inappropriate angling of the catheter/needle, etc. The devices and methods disclosed herein can provide catheter/needle securement and optimal inclination, a hermetically sealed chamber to resist infection and/or contamination, inert gas or soothing anesthetic vapor drugs in and around the device, and various skin-contacting layers and structures that promote ventilation and patient comfort in and around the insertion site.

21 Claims, 37 Drawing Sheets

Related U.S. Application Data continuation of application No. 15/853,469, filed on Dec. 22, 2017, now Pat. No. 10,173,035.

(60) Provisional application No. 62/439,302, filed on Dec. 27, 2016.

(51) Int. Cl.

| | | |
|---|---|---|
| *A61B 5/021* | (2006.01) | |
| *A61B 5/1455* | (2006.01) | |
| *A61B 5/024* | (2006.01) | |
| *A61M 25/00* | (2006.01) | |
| *A61B 5/00* | (2006.01) | |
| *A61B 5/02* | (2006.01) | |

(52) U.S. Cl.
CPC ...... *A61B 5/02438* (2013.01); *A61B 5/14552* (2013.01); *A61M 25/0097* (2013.01); *A61B 5/002* (2013.01); *A61B 5/02042* (2013.01); *A61B 5/443* (2013.01); *A61B 5/6802* (2013.01); *A61B 5/6824* (2013.01); *A61B 5/6831* (2013.01); *A61B 2560/0475* (2013.01); *A61M 2025/0019* (2013.01); *A61M 2025/0056* (2013.01); *A61M 2025/0206* (2013.01); *A61M 2025/028* (2013.01); *A61M 2025/0246* (2013.01); *A61M 2202/048* (2013.01); *A61M 2205/15* (2013.01); *A61M 2205/18* (2013.01); *A61M 2205/3306* (2013.01)

(56) References Cited

U.S. PATENT DOCUMENTS

| | | | |
|---|---|---|---|
| 3,901,226 | A | 8/1975 | Scardenzan |
| 4,224,937 | A | 9/1980 | Gordon |
| 4,250,880 | A | 2/1981 | Gordon |
| 4,397,647 | A | 8/1983 | Gordon |
| 4,517,971 | A * | 5/1985 | Sorbonne ............... A61M 25/02 604/174 |
| 4,585,443 | A | 4/1986 | Kaufman |
| 4,633,863 | A | 1/1987 | Filips et al. |
| 4,666,434 | A | 5/1987 | Kaufman |
| 4,669,458 | A | 6/1987 | Abraham et al. |
| 4,679,553 | A | 7/1987 | Proulx et al. |
| 4,698,057 | A | 10/1987 | Joishy |
| 4,898,587 | A | 2/1990 | Mera |
| 5,074,847 | A | 12/1991 | Greenwell et al. |
| 5,112,313 | A * | 5/1992 | Sallee ................... A61M 25/02 D24/130 |
| 5,304,145 | A | 4/1994 | Blair |
| 6,231,548 | B1 | 5/2001 | Bassett |
| 6,257,240 | B1 | 7/2001 | Shesol |
| 6,361,523 | B1 | 3/2002 | Bierman |
| 6,375,639 | B1 | 4/2002 | Duplessie et al. |
| 6,500,154 | B1 | 12/2002 | Hakky et al. |
| 6,572,240 | B2 | 6/2003 | Reinert, Sr. |
| 6,572,588 | B1 | 6/2003 | Bierman et al. |
| 6,579,267 | B2 | 6/2003 | Lynch et al. |
| 6,730,113 | B2 | 5/2004 | Eckhardt et al. |
| 6,827,707 | B2 | 12/2004 | Wright et al. |
| 6,890,321 | B2 | 5/2005 | Luther et al. |
| 7,014,627 | B2 | 3/2006 | Bierman |
| 7,022,111 | B2 | 4/2006 | Duplessie et al. |
| 7,083,597 | B2 | 8/2006 | Lynch et al. |
| 7,087,038 | B2 | 8/2006 | Lee |
| 7,112,191 | B2 | 9/2006 | Daga |
| 7,135,010 | B2 | 11/2006 | Buckman et al. |
| 7,214,207 | B2 | 5/2007 | Lynch et al. |
| D547,862 | S | 7/2007 | Dikeman et al. |
| 7,247,150 | B2 | 7/2007 | Bierman |
| 7,270,649 | B2 | 9/2007 | Fitzgerald |
| 7,294,751 | B2 | 11/2007 | Propp et al. |
| D567,941 | S | 4/2008 | Dikeman et al. |
| D568,466 | S | 5/2008 | Dikeman et al. |
| D569,506 | S | 5/2008 | Dikeman et al. |
| 7,377,915 | B2 | 5/2008 | Rasmussen et al. |
| 7,458,964 | B2 | 12/2008 | Mosler et al. |
| 7,569,034 | B2 | 8/2009 | Lynch et al. |
| 7,594,910 | B2 | 9/2009 | Butts et al. |
| 7,594,911 | B2 | 9/2009 | Powers et al. |
| D604,411 | S | 11/2009 | Gomez |
| 7,618,400 | B2 | 11/2009 | Chawki |
| 7,635,354 | B2 | 12/2009 | Navarro et al. |
| 7,635,355 | B2 | 12/2009 | Bierman |
| 7,674,948 | B2 | 3/2010 | Propp et al. |
| 7,695,458 | B2 | 4/2010 | Belley et al. |
| 7,696,182 | B2 | 4/2010 | Prosl |
| 7,699,810 | B2 | 4/2010 | Rosenburg |
| 7,723,561 | B2 | 5/2010 | Propp |
| D618,792 | S | 6/2010 | Bierman |
| 7,731,708 | B2 | 6/2010 | Haarala et al. |
| 7,736,337 | B2 | 6/2010 | Diep et al. |
| 7,753,889 | B2 | 7/2010 | Rosenburg |
| D622,841 | S | 8/2010 | Bierman |
| 7,766,867 | B2 | 8/2010 | Lynch et al. |
| 7,799,001 | B2 | 9/2010 | Bierman |
| 7,806,873 | B2 | 10/2010 | Dikeman et al. |
| 7,812,212 | B2 | 10/2010 | Propp et al. |
| 7,875,019 | B2 | 1/2011 | Barron et al. |
| 7,879,013 | B2 | 2/2011 | Smith et al. |
| 7,887,515 | B2 | 2/2011 | Bierman |
| 7,918,829 | B2 | 4/2011 | Daniels, Jr. et al. |
| 7,967,788 | B2 | 6/2011 | Chandrasekar et al. |
| 7,967,792 | B2 | 6/2011 | Bierman |
| 7,972,310 | B2 | 7/2011 | Kessler |
| 7,981,087 | B2 | 7/2011 | Gesler |
| 8,006,699 | B2 | 8/2011 | Rozier et al. |
| 8,016,792 | B2 | 9/2011 | Wright et al. |
| 8,016,793 | B2 | 9/2011 | Wright et al. |
| 8,016,794 | B2 | 9/2011 | Rosenburg et al. |
| 8,016,813 | B2 | 9/2011 | Rosenburg et al. |
| 8,029,476 | B2 | 10/2011 | Rosenburg et al. |
| 8,029,479 | B2 | 10/2011 | Guthrie |
| 8,038,653 | B2 | 10/2011 | Rosenburg et al. |
| 8,052,648 | B2 | 11/2011 | Dikeman et al. |
| 8,057,443 | B2 | 11/2011 | McNeil |
| 8,123,681 | B2 | 2/2012 | Schaeffer |
| 8,128,602 | B2 | 3/2012 | Tollini et al. |
| 8,137,323 | B2 | 3/2012 | Rosenburg et al. |
| 8,142,401 | B2 | 3/2012 | Rosenburg |
| 8,147,459 | B2 | 4/2012 | Rosenburg et al. |
| 8,157,770 | B2 | 4/2012 | Elwell et al. |
| 8,167,851 | B2 | 5/2012 | Sen |
| 8,197,447 | B2 | 6/2012 | Wright |
| 8,211,064 | B2 | 7/2012 | Sloan |
| 8,235,945 | B2 | 8/2012 | Baid |
| 8,241,253 | B2 | 8/2012 | Bracken |
| 8,286,657 | B2 | 10/2012 | Belley et al. |
| 8,298,212 | B2 | 10/2012 | Haindl et al. |
| 8,313,461 | B2 | 11/2012 | Walker et al. |
| 8,313,469 | B2 | 11/2012 | Fiser |
| 8,328,764 | B2 | 12/2012 | Rosenburg et al. |
| 8,343,108 | B2 | 1/2013 | Rosenburg et al. |
| 8,343,115 | B2 | 1/2013 | Lynch et al. |
| 8,353,876 | B2 | 1/2013 | Suwito et al. |
| 8,366,652 | B2 | 2/2013 | Dacey, Jr. et al. |
| 8,366,678 | B2 | 2/2013 | Bierman et al. |
| 8,394,065 | B2 | 3/2013 | Bierman |
| 8,394,066 | B2 | 3/2013 | Rosenburg et al. |
| 8,394,067 | B2 | 3/2013 | Bracken et al. |
| 8,444,603 | B2 | 5/2013 | Rosenburg et al. |
| 8,460,229 | B2 | 6/2013 | Dacey, Jr. et al. |
| 8,465,458 | B2 | 6/2013 | Bierman |
| 8,486,004 | B1 | 7/2013 | Propp |
| 8,486,026 | B2 | 7/2013 | Koberstein |
| 8,529,544 | B2 | 9/2013 | Haarala et al. |
| 8,540,680 | B2 | 9/2013 | Burn |
| 8,556,859 | B2 | 10/2013 | Nilson et al. |
| 8,579,863 | B2 | 11/2013 | Scherr |
| 8,579,864 | B2 | 11/2013 | Rosenburg et al. |
| 8,585,654 | B2 | 11/2013 | Rosenburg et al. |
| 8,585,655 | B2 | 11/2013 | Bierman |
| 8,591,471 | B1 | 11/2013 | Marble |

(56) References Cited

U.S. PATENT DOCUMENTS

| | | |
|---|---|---|
| 8,603,037 B1 | 12/2013 | Wiley et al. |
| 8,628,511 B2 | 1/2014 | Rosenburg et al. |
| 8,636,699 B2 | 1/2014 | Russo |
| 8,641,677 B2 | 2/2014 | Rawls |
| 8,647,292 B2 | 2/2014 | Dacey, Jr. et al. |
| 8,668,674 B2 | 3/2014 | White et al. |
| 8,696,647 B2 | 4/2014 | Bizup et al. |
| 8,702,640 B2 | 4/2014 | Dacey, Jr. et al. |
| 8,706,211 B2 | 4/2014 | Dacey, Jr. et al. |
| 8,715,242 B2 | 5/2014 | Helm, Jr. |
| 8,715,250 B2 | 5/2014 | Tremblay |
| 8,721,606 B2 | 5/2014 | Simmons et al. |
| 8,734,401 B2 | 5/2014 | Beran |
| 8,734,718 B2 | 5/2014 | Dacey, Jr. et al. |
| 8,740,852 B2 | 6/2014 | Aviles |
| 8,747,360 B2 | 6/2014 | Peterson et al. |
| 8,747,387 B2 | 6/2014 | Belley et al. |
| 8,771,232 B2 | 7/2014 | Rosenburg et al. |
| 8,795,237 B2 | 8/2014 | Vitaris et al. |
| 8,827,959 B2 | 9/2014 | Wright et al. |
| 8,834,426 B2 | 9/2014 | Shipman |
| 8,870,819 B2 | 10/2014 | Walker et al. |
| 8,881,899 B2 | 11/2014 | Fink et al. |
| 8,915,885 B2 | 12/2014 | Smith et al. |
| 8,915,891 B2 | 12/2014 | Bornhoft |
| 8,920,380 B2 | 12/2014 | Rosenburg |
| 8,926,563 B2 | 1/2015 | Steube |
| 8,926,565 B2 | 1/2015 | Cusworth |
| 8,932,263 B2 | 1/2015 | Rosenburg et al. |
| 8,936,576 B2 | 1/2015 | Rosenburg et al. |
| 8,956,329 B2 | 2/2015 | Rosenburg et al. |
| 8,968,253 B2 | 3/2015 | Wallace et al. |
| 8,974,434 B2 | 3/2015 | Rosenburg et al. |
| 8,986,257 B2 | 3/2015 | Rosenburg et al. |
| 9,011,897 B2 | 4/2015 | Ash et al. |
| D731,641 S | 6/2015 | Du |
| D732,160 S | 6/2015 | Du |
| 9,044,539 B2 | 6/2015 | Duncan |
| 9,056,186 B2 | 6/2015 | Wright et al. |
| 9,056,187 B2 | 6/2015 | Rosenburg et al. |
| 9,061,122 B2 | 6/2015 | Bierman et al. |
| 9,084,848 B2 | 7/2015 | Schiltges et al. |
| 9,089,335 B2 | 7/2015 | Okamura |
| 9,138,560 B2 | 9/2015 | Wright et al. |
| 9,155,301 B2 | 10/2015 | Wirsen et al. |
| 9,155,866 B2 | 10/2015 | Bornhoft |
| 9,155,867 B2 | 10/2015 | Peterson et al. |
| 9,180,275 B2 | 11/2015 | Helm |
| 9,186,455 B2 | 11/2015 | Moyer |
| 9,205,230 B2 | 12/2015 | Rosenburg et al. |
| 9,248,093 B2 | 2/2016 | Kelley, III et al. |
| 9,259,349 B2 | 2/2016 | Walker et al. |
| 9,259,564 B2 | 2/2016 | Bagwell et al. |
| 9,283,355 B2 | 3/2016 | Rosenburg et al. |
| 9,314,596 B2 | 4/2016 | Rosenburg et al. |
| 9,352,119 B2 | 5/2016 | Burkholz et al. |
| 9,358,368 B2 | 6/2016 | Beran |
| 9,381,321 B2 | 7/2016 | Rosenburg et al. |
| 9,381,322 B2 | 7/2016 | Rosenburg et al. |
| 9,381,323 B2 | 7/2016 | Rosenburg et al. |
| 9,387,306 B2 | 7/2016 | Andreae et al. |
| 9,486,613 B2 | 11/2016 | Dickert et al. |
| 9,492,640 B2 | 11/2016 | Rosenhan |
| 9,522,254 B2 | 12/2016 | Belson |
| 9,526,868 B2 | 12/2016 | Bennett |
| 9,526,869 B2 | 12/2016 | Beran |
| 9,526,871 B2 | 12/2016 | Wright et al. |
| 9,545,503 B2 | 1/2017 | Rosenberg |
| 9,550,043 B2 | 1/2017 | Rosenberg et al. |
| 9,555,230 B2 | 1/2017 | Jochum et al. |
| 9,561,348 B2 | 2/2017 | Bierman |
| 9,566,417 B1 | 2/2017 | Propp |
| 9,579,487 B2 | 2/2017 | Mancino |
| 9,592,365 B2 | 3/2017 | Stroup et al. |
| 9,604,031 B2 | 3/2017 | Heinecke et al. |
| 9,616,200 B2 | 4/2017 | Smith et al. |
| 9,629,983 B2 | 4/2017 | Sung |
| 9,649,411 B2 | 5/2017 | Hoang |
| 9,652,595 B1 | 5/2017 | Carr et al. |
| 9,656,045 B2 | 5/2017 | Rosenberg et al. |
| 9,662,474 B2 | 5/2017 | Chandrasekar et al. |
| 9,717,885 B2 | 8/2017 | Martinez et al. |
| 9,731,097 B2 | 8/2017 | Andino et al. |
| 9,744,273 B2 | 8/2017 | Kelley, III et al. |
| 9,782,536 B2 | 10/2017 | Skutnik et al. |
| 9,782,567 B2 | 10/2017 | Rosenberg et al. |
| 9,789,227 B1 | 10/2017 | El-Hennawy et al. |
| 9,789,287 B2 | 10/2017 | Ehrlich |
| 9,789,288 B2 | 10/2017 | Rosenberg et al. |
| 9,808,601 B2 | 11/2017 | Helm, Jr. |
| 9,814,863 B2 | 11/2017 | Kyvik et al. |
| 9,827,396 B2 | 11/2017 | Souza et al. |
| 9,849,269 B2 | 12/2017 | Rosenberg et al. |
| 9,861,791 B2 | 1/2018 | Rawls |
| 9,867,966 B2 | 1/2018 | Tanabe et al. |
| 9,872,941 B2 | 1/2018 | Hoang |
| D810,287 S | 2/2018 | Bellnoit et al. |
| 9,895,514 B2 | 2/2018 | Bierman et al. |
| 9,907,934 B2 | 3/2018 | Rosenburg et al. |
| 9,919,134 B2 | 3/2018 | Rosenburg et al. |
| 9,925,358 B2 | 3/2018 | Elsamahy |
| 9,937,327 B2 | 4/2018 | Rosenbueg et al. |
| 9,981,111 B2 | 5/2018 | Friedrich |
| 9,993,620 B2 | 6/2018 | Le et al. |
| D824,515 S | 7/2018 | Kyvik |
| 10,046,142 B2 | 8/2018 | Rosenburg |
| 10,058,682 B2 | 8/2018 | Rosenburg et al. |
| 10,086,168 B2 | 10/2018 | Olson et al. |
| 10,117,971 B2 | 11/2018 | Hoang |
| D835,262 S | 12/2018 | Burkholz et al. |
| 10,173,035 B2 * | 1/2019 | Albany ............... A61M 25/02 |
| 10,173,036 B2 | 1/2019 | Wilborn et al. |
| 10,195,400 B2 | 2/2019 | Vaillancourt et al. |
| 10,232,145 B2 | 3/2019 | Bierman et al. |
| 10,238,839 B2 | 3/2019 | Ehrlich |
| D846,114 S | 4/2019 | Kyvik |
| 10,244,935 B2 | 4/2019 | Ha et al. |
| 10,252,023 B2 | 4/2019 | Wiley et al. |
| 10,252,034 B2 | 4/2019 | Aklog et al. |
| 10,265,507 B2 | 4/2019 | Belson |
| 10,279,148 B2 | 5/2019 | Rosenberg et al. |
| 10,293,140 B2 | 5/2019 | Rosenberg et al. |
| 10,315,009 B2 | 6/2019 | Rosenberg et al. |
| 10,335,322 B2 | 7/2019 | Doshi et al. |
| 10,335,518 B2 | 7/2019 | Appelt et al. |
| 10,335,576 B2 | 7/2019 | Rosenberg et al. |
| 10,342,954 B2 | 7/2019 | Rosenberg et al. |
| 10,350,334 B2 | 7/2019 | Kelley, III et al. |
| 10,350,388 B2 | 7/2019 | Kyvik et al. |
| 10,357,635 B2 | 7/2019 | Korkuch et al. |
| 10,384,037 B2 | 8/2019 | Rosenberg et al. |
| 10,387,613 B2 | 8/2019 | Manetta et al. |
| 10,398,878 B2 | 9/2019 | Engelhardt |
| 10,406,321 B1 | 9/2019 | Macy |
| 10,433,790 B2 | 10/2019 | Ofek et al. |
| 10,441,750 B2 | 10/2019 | Vaillancourt et al. |
| 10,449,575 B2 | 10/2019 | Ryan et al. |
| 10,456,559 B2 | 10/2019 | Wilborn et al. |
| 10,463,837 B2 | 11/2019 | Bierman et al. |
| 10,471,236 B2 | 11/2019 | Rosenberg et al. |
| 10,478,593 B2 | 11/2019 | Jones et al. |
| 10,525,237 B2 | 1/2020 | Burkholz et al. |
| 10,532,188 B2 | 1/2020 | Rosenberg et al. |
| 10,537,714 B2 | 1/2020 | Andino et al. |
| 10,549,070 B2 | 2/2020 | Howell et al. |
| 10,549,072 B2 | 2/2020 | Burkholz et al. |
| 10,576,250 B2 | 3/2020 | Burkholz |
| 10,576,251 B2 | 3/2020 | Parkhurst |
| 10,596,350 B2 | 3/2020 | Kyvik |
| 10,632,289 B2 | 4/2020 | Jones et al. |
| 10,639,453 B2 | 5/2020 | Olson et al. |
| 10,675,440 B2 | 6/2020 | Abitabilo et al. |
| 10,682,499 B2 | 6/2020 | Isaacson et al. |
| 10,682,507 B2 | 6/2020 | Helm |

(56) References Cited

U.S. PATENT DOCUMENTS

| | | | |
|---|---|---|---|
| 10,688,280 B2 | 6/2020 | Blanchard et al. |
| 10,709,874 B2 | 7/2020 | Rosenberg et al. |
| 10,722,685 B2 | 7/2020 | Blanchard et al. |
| D893,707 S | 8/2020 | Burkholz et al. |
| 10,729,888 B2 | 8/2020 | Beran |
| 10,737,063 B2 | 8/2020 | Horst et al. |
| 10,751,512 B2 | 8/2020 | Baid |
| 10,773,054 B2 | 9/2020 | Shimer et al. |
| 10,786,652 B2 | 9/2020 | Doshi et al. |
| 10,799,679 B2 | 10/2020 | Roberts et al. |
| 10,814,105 B2 | 10/2020 | Rosenberg et al. |
| 10,814,106 B2 | 10/2020 | Garrison et al. |
| 10,814,110 B2 | 10/2020 | Gorn et al. |
| 10,874,835 B2 | 12/2020 | Rosenberg et al. |
| 10,898,687 B2 | 1/2021 | Souza et al. |
| 10,905,847 B2 | 2/2021 | Burkholz |
| 10,940,240 B2 | 3/2021 | Babu et al. |
| 10,946,176 B2 | 3/2021 | Isaacson et al. |
| 10,980,980 B2 | 4/2021 | Ishida |
| 10,987,041 B2 | 4/2021 | Maseda et al. |
| 10,987,486 B2 | 4/2021 | Burkholz |
| 11,033,717 B2 | 6/2021 | Overstreet et al. |
| 11,045,629 B2 | 6/2021 | Rosenberg et al. |
| 11,045,630 B2 | 6/2021 | Rosenberg et al. |
| 11,058,853 B2 | 7/2021 | Rosenberg et al. |
| 11,077,286 B2 | 8/2021 | Augustine et al. |
| 11,090,406 B1 | 8/2021 | Cros et al. |
| 11,103,681 B2 | 8/2021 | Tan et al. |
| 11,123,523 B2 | 9/2021 | Harding et al. |
| 11,129,573 B2 | 9/2021 | Ofek et al. |
| 11,141,319 B2 | 10/2021 | Doshi et al. |
| 11,147,951 B2 | 10/2021 | Rosenberg et al. |
| 11,167,112 B2 | 11/2021 | Volpicelli |
| 11,167,113 B2 | 11/2021 | Friedrich |
| 11,191,928 B2 | 12/2021 | Almansouri |
| 11,207,501 B2 | 12/2021 | Funk et al. |
| 11,224,720 B2 | 1/2022 | Brunetti et al. |
| 11,224,723 B2 | 1/2022 | Rosenberg et al. |
| 11,224,724 B2 | 1/2022 | Korkuch et al. |
| 11,247,025 B2 | 2/2022 | Hanson et al. |
| 11,273,291 B2 | 3/2022 | Yokota |
| 11,291,800 B2 | 4/2022 | Yokota |
| 11,298,508 B2 | 4/2022 | Ishida et al. |
| 11,318,287 B2 | 5/2022 | Teoh et al. |
| 11,351,352 B1 | 6/2022 | Kreatsoulas et al. |
| 11,383,074 B2 | 7/2022 | Isaacson et al. |
| 11,389,621 B2 | 7/2022 | Overstreet et al. |
| 11,395,905 B2 | 7/2022 | Burkholz |
| 11,413,432 B2 | 8/2022 | Hyer et al. |
| 11,426,556 B2 | 8/2022 | O'Sullivan et al. |
| 11,426,558 B2 | 8/2022 | O'Bryan et al. |
| 11,452,846 B2 | 9/2022 | Rosenberg |
| 11,458,281 B2 | 10/2022 | Horvath et al. |
| 11,511,081 B2 | 11/2022 | Aklog et al. |
| 11,524,145 B2 | 12/2022 | Baid |
| 11,571,551 B2 | 2/2023 | Burkholz et al. |
| 11,577,051 B2 | 2/2023 | Rosenberg et al. |
| 11,612,717 B2 | 3/2023 | Burkholz et al. |
| 11,617,864 B2 | 4/2023 | Burkholz et al. |
| 11,633,573 B2 | 4/2023 | Ciccone |
| 2002/0092529 A1 | 7/2002 | Lundgaard et al. |
| 2003/0018373 A1 | 1/2003 | Eckhardt et al. |
| 2003/0216686 A1 | 11/2003 | Lynch et al. |
| 2004/0034398 A1 | 2/2004 | Eckhardt et al. |
| 2004/0158209 A1 | 8/2004 | Wright |
| 2004/0204685 A1 | 10/2004 | Wright et al. |
| 2005/0043686 A1 | 2/2005 | Tollini |
| 2005/0197647 A1 | 9/2005 | Dolliver et al. |
| 2005/0215953 A1 | 9/2005 | Rossen |
| 2005/0234405 A1 | 10/2005 | Dikeman et al. |
| 2005/0256458 A1 | 11/2005 | Howard et al. |
| 2005/0256459 A1 | 11/2005 | Howard et al. |
| 2005/0273986 A1 | 12/2005 | Honchel |
| 2005/0273987 A1 | 12/2005 | Honchel |
| 2006/0015068 A1 | 1/2006 | Amisar et al. |
| 2006/0200195 A1 | 9/2006 | Yang |
| 2006/0217669 A1 | 9/2006 | Botha |
| 2007/0043326 A1* | 2/2007 | Navarro ............. A61M 25/02 604/264 |
| 2007/0060874 A1 | 3/2007 | Nesbitt et al. |
| 2007/0083163 A1 | 4/2007 | Rydell |
| 2007/0106222 A1 | 5/2007 | Bennett |
| 2007/0142785 A1 | 6/2007 | Rozier et al. |
| 2007/0156070 A1 | 7/2007 | Schwab |
| 2007/0250011 A1 | 10/2007 | Lee |
| 2007/0259026 A1 | 11/2007 | Ang et al. |
| 2007/0260187 A1 | 11/2007 | Hawkins |
| 2007/0270758 A1 | 11/2007 | Hanner et al. |
| 2007/0299405 A1 | 12/2007 | Kaufmann et al. |
| 2008/0071224 A1 | 3/2008 | Forsyth |
| 2008/0200880 A1 | 8/2008 | Kyvik et al. |
| 2008/0306454 A1 | 12/2008 | Sikora |
| 2008/0319398 A1 | 12/2008 | Bizup |
| 2009/0149814 A1 | 6/2009 | Bailey et al. |
| 2009/0240121 A1 | 9/2009 | Bickoff |
| 2009/0257910 A1 | 10/2009 | Segal |
| 2009/0299294 A1 | 12/2009 | Pinkus |
| 2010/0100049 A1 | 4/2010 | Godfrey |
| 2010/0113871 A1 | 5/2010 | Dias et al. |
| 2010/0256487 A1 | 10/2010 | Hawkins et al. |
| 2011/0021997 A1 | 1/2011 | Kyvik et al. |
| 2011/0040258 A1 | 2/2011 | Robison |
| 2011/0054409 A1 | 3/2011 | Nishtala |
| 2011/0060070 A1 | 3/2011 | Dias |
| 2011/0098654 A1 | 4/2011 | Shipman |
| 2011/0123475 A1 | 5/2011 | Dias et al. |
| 2011/0124772 A1 | 5/2011 | Wang et al. |
| 2011/0160644 A1 | 6/2011 | Dacey, Jr. et al. |
| 2011/0160681 A1 | 6/2011 | Dacey, Jr. et al. |
| 2011/0178466 A1 | 7/2011 | Vioreanu et al. |
| 2011/0178467 A1 | 7/2011 | Bierman et al. |
| 2011/0208102 A1 | 8/2011 | Chawki |
| 2011/0213025 A1 | 9/2011 | Finch, Jr. |
| 2012/0010572 A1 | 1/2012 | Bennett |
| 2012/0016312 A1 | 1/2012 | Brown et al. |
| 2012/0059328 A1 | 3/2012 | Dikeman et al. |
| 2012/0191044 A1 | 7/2012 | Koike |
| 2012/0197204 A1 | 8/2012 | Helm, Jr. |
| 2012/0197206 A1 | 8/2012 | Glenn |
| 2012/0209090 A1 | 8/2012 | Goodall et al. |
| 2012/0209206 A1 | 8/2012 | Scandone, Jr. |
| 2012/0220947 A1 | 8/2012 | Dikeman et al. |
| 2012/0232489 A1 | 9/2012 | Helm, Jr. |
| 2013/0018319 A1 | 1/2013 | Abe et al. |
| 2013/0110048 A1 | 5/2013 | Herzog |
| 2013/0158506 A1 | 6/2013 | Harris et al. |
| 2013/0197325 A1 | 8/2013 | Petisce et al. |
| 2013/0303986 A1 | 11/2013 | Penalosa, Jr. |
| 2014/0039401 A1 | 2/2014 | Kerr et al. |
| 2014/0046265 A1 | 2/2014 | Kay et al. |
| 2014/0066882 A1 | 3/2014 | Heinecke et al. |
| 2014/0155831 A1 | 6/2014 | Lopez et al. |
| 2014/0200549 A1 | 7/2014 | Norkunas |
| 2015/0005712 A1 | 1/2015 | Kyvik et al. |
| 2015/0073347 A1 | 3/2015 | Friedrich et al. |
| 2015/0224285 A1 | 8/2015 | Howell et al. |
| 2015/0224286 A1 | 8/2015 | The et al. |
| 2015/0258309 A1 | 9/2015 | Kyvik et al. |
| 2015/0343177 A1 | 12/2015 | Bond et al. |
| 2016/0008582 A1 | 1/2016 | Burkholz et al. |
| 2016/0015931 A1 | 1/2016 | Ryan et al. |
| 2016/0151607 A1 | 6/2016 | Kyvik et al. |
| 2016/0158499 A1 | 6/2016 | Helm |
| 2016/0166807 A1 | 6/2016 | De Stefano et al. |
| 2016/0206855 A1 | 7/2016 | Howell et al. |
| 2016/0220805 A1 | 8/2016 | Goral et al. |
| 2016/0256665 A1 | 9/2016 | Doshi et al. |
| 2016/0317786 A1 | 11/2016 | Friedrich |
| 2016/0354580 A1 | 12/2016 | Teoh et al. |
| 2016/0361517 A1 | 12/2016 | Yazaki |
| 2017/0073548 A1 | 3/2017 | Karim et al. |
| 2017/0120000 A1 | 5/2017 | Osypka et al. |
| 2017/0143941 A1 | 5/2017 | Augustine et al. |
| 2017/0202218 A1 | 7/2017 | Fridman et al. |

(56) References Cited

U.S. PATENT DOCUMENTS

| | | |
|---|---|---|
| 2017/0246029 A1 | 8/2017 | Clark |
| 2017/0273628 A1 | 9/2017 | Ofek et al. |
| 2018/0071493 A1 | 3/2018 | Konstantarakis |
| 2018/0161546 A1 | 6/2018 | Aslam et al. |
| 2018/0177982 A1 | 6/2018 | Albany et al. |
| 2018/0256855 A1 | 9/2018 | Terasawa et al. |
| 2018/0339135 A1 | 11/2018 | Nathan |
| 2019/0015636 A1 | 1/2019 | Robinson |
| 2019/0054270 A1 | 2/2019 | Bornhoft |
| 2019/0111235 A1 | 4/2019 | Jones |
| 2019/0151618 A1 | 5/2019 | Aklog et al. |
| 2019/0151620 A1 | 5/2019 | Aklog et al. |
| 2019/0184140 A1 | 6/2019 | Delulio |
| 2019/0240459 A1 | 8/2019 | Belson |
| 2019/0247623 A1 | 8/2019 | Helm et al. |
| 2019/0351183 A1 | 11/2019 | Ishida |
| 2019/0366050 A1 | 12/2019 | Oliveira et al. |
| 2019/0381283 A1 | 12/2019 | Burkholz et al. |
| 2020/0030592 A1 | 1/2020 | Cheche |
| 2020/0038634 A1 | 2/2020 | Garrison et al. |
| 2020/0046946 A1 | 2/2020 | Staley et al. |
| 2020/0114123 A1 | 4/2020 | Rosenberg et al. |
| 2020/0155808 A1 | 5/2020 | Burkholz et al. |
| 2020/0171273 A1 | 6/2020 | Bierman et al. |
| 2020/0246592 A1 | 8/2020 | Clavijo et al. |
| 2020/0330651 A1 | 10/2020 | Prosl |
| 2020/0338311 A1 | 10/2020 | Howell et al. |
| 2020/0360665 A1 | 11/2020 | Horst et al. |
| 2020/0368493 A1 | 11/2020 | Ash |
| 2020/0368498 A1 | 11/2020 | Vaillancourt et al. |
| 2020/0406003 A1 | 12/2020 | Shimer et al. |
| 2021/0008347 A1 | 1/2021 | Galgano et al. |
| 2021/0038866 A1 | 2/2021 | Rosenberg et al. |
| 2021/0038868 A1 | 2/2021 | Naing et al. |
| 2021/0060213 A1 | 3/2021 | Rosenblatt et al. |
| 2021/0106786 A1 | 4/2021 | Burkholz |
| 2021/0154438 A1 | 5/2021 | Ishida |
| 2021/0154459 A1 | 5/2021 | Wiley et al. |
| 2021/0170075 A1 | 6/2021 | Babu et al. |
| 2021/0213240 A1 | 7/2021 | Burkholz |
| 2021/0228840 A1 | 7/2021 | Le et al. |
| 2021/0236698 A1 | 8/2021 | Prosl |
| 2021/0236721 A1 | 8/2021 | Skutnik et al. |
| 2021/0283375 A1 | 9/2021 | Spitler |
| 2021/0353908 A1 | 11/2021 | Rosenberg et al. |
| 2021/0361914 A1 | 11/2021 | Ishida |
| 2021/0361927 A1 | 11/2021 | Barry |
| 2021/0370026 A1 | 12/2021 | Rosenberg et al. |
| 2021/0393875 A1 | 12/2021 | Chaves et al. |
| 2021/0402154 A1 | 12/2021 | Baid |
| 2022/0023597 A1 | 1/2022 | Rosenberg et al. |
| 2022/0040456 A1 | 2/2022 | Ishida |
| 2022/0072277 A1 | 3/2022 | Rosenhan |
| 2022/0072278 A1 | 3/2022 | Funk et al. |
| 2022/0126026 A1 | 4/2022 | Ishida |
| 2022/0134058 A1 | 5/2022 | Korkuch et al. |
| 2022/0161005 A1 | 5/2022 | Burkholz et al. |
| 2022/0226614 A1 | 7/2022 | Ishida et al. |
| 2022/0362521 A1 | 11/2022 | O'Bryan et al. |
| 2023/0018539 A1 | 1/2023 | Andino et al. |
| 2023/0145227 A1 | 5/2023 | Burkholz et al. |

FOREIGN PATENT DOCUMENTS

| | | |
|---|---|---|
| EP | 2075029 B1 | 9/2010 |
| EP | 2277581 A1 | 1/2011 |
| EP | 3492134 A1 | 6/2019 |
| FR | 3081714 A1 | 12/2019 |
| GB | 2046095 A | 11/1980 |
| JP | 2005-508664 | 4/2005 |
| JP | 2012-152552 | 8/2012 |
| JP | 2013-501595 | 1/2013 |
| JP | 2016-510676 | 4/2016 |
| KR | 2014-0069877 A | 6/2014 |
| KR | 10-1448359 B1 | 10/2014 |
| TR | 201101486 A2 | 10/2011 |
| WO | WO 1998/047556 A1 | 10/1998 |
| WO | WO 01/68180 A1 | 9/2001 |
| WO | WO 02/102419 | 12/2002 |
| WO | WO 2004/016309 A2 | 2/2004 |
| WO | WO 2004/052427 A1 | 6/2004 |
| WO | WO 2005/009524 A1 | 2/2005 |
| WO | WO 2005/014087 A1 | 2/2005 |
| WO | WO 2005/069954 A2 | 8/2005 |
| WO | WO 2005/102438 A2 | 11/2005 |
| WO | WO 2006/019725 A2 | 2/2006 |
| WO | WO 2006/085331 A9 | 8/2006 |
| WO | WO 2006/097755 A8 | 9/2006 |
| WO | WO 2007/027545 A2 | 3/2007 |
| WO | WO 2007/044878 A2 | 4/2007 |
| WO | WO 2007/082093 A3 | 7/2007 |
| WO | WO 2007/100776 A2 | 9/2007 |
| WO | WO 2007/142746 A1 | 12/2007 |
| WO | WO 2008/058286 A2 | 5/2008 |
| WO | WO 2008/137587 A1 | 11/2008 |
| WO | WO 2008/151047 A1 | 12/2008 |
| WO | WO 2008/157703 A1 | 12/2008 |
| WO | WO 2008/157710 A1 | 12/2008 |
| WO | WO 2009/027778 A1 | 3/2009 |
| WO | WO 2010/039751 A1 | 4/2010 |
| WO | WO 2010/039752 A1 | 4/2010 |
| WO | WO 2010/048401 A2 | 4/2010 |
| WO | WO 2010/057080 A1 | 5/2010 |
| WO | WO 2010/061143 A1 | 6/2010 |
| WO | WO 2010/088192 A1 | 8/2010 |
| WO | WO 2010/144674 A2 | 12/2010 |
| WO | WO 2011/019985 | 2/2011 |
| WO | WO 2011/058171 A1 | 5/2011 |
| WO | WO 2011/109356 A2 | 9/2011 |
| WO | WO 2011/146781 A1 | 11/2011 |
| WO | WO 2012/018891 A2 | 2/2012 |
| WO | WO 2012/048133 A2 | 4/2012 |
| WO | WO 2012/106088 A2 | 8/2012 |
| WO | WO 2012/154754 A1 | 11/2012 |
| WO | WO 2012/162251 A1 | 11/2012 |
| WO | WO 2012/176071 A2 | 12/2012 |
| WO | WO 2013/015836 A2 | 1/2013 |
| WO | WO 2013/058828 A1 | 4/2013 |
| WO | WO 2013/082884 A1 | 6/2013 |
| WO | WO 2013/086098 A1 | 6/2013 |
| WO | WO 2014/015254 A1 | 1/2014 |
| WO | WO 2014/022597 A1 | 2/2014 |
| WO | WO 2014/036348 A1 | 3/2014 |
| WO | WO 2014/120741 A1 | 8/2014 |
| WO | WO 2014/149668 A1 | 9/2014 |
| WO | WO 2014/162381 A1 | 10/2014 |
| WO | WO 2014/169740 A1 | 10/2014 |
| WO | WO 2014/169741 A1 | 10/2014 |
| WO | WO 2015/006892 A1 | 1/2015 |
| WO | WO 2015/017961 A1 | 2/2015 |
| WO | WO 2015/020882 A1 | 2/2015 |
| WO | WO 2015/023358 A1 | 2/2015 |
| WO | WO 2015/023922 A1 | 2/2015 |
| WO | WO 2014/210565 A2 | 3/2015 |
| WO | WO 2015/123684 A1 | 8/2015 |
| WO | WO 2015/166157 A1 | 11/2015 |
| WO | WO 2016/006751 A1 | 1/2016 |
| WO | WO 2016/063287 A1 | 4/2016 |
| WO | WO 2016/077234 A1 | 5/2016 |
| WO | WO 2016/083806 A1 | 6/2016 |
| WO | WO 2016/089894 A1 | 6/2016 |
| WO | WO 2016/123278 A1 | 8/2016 |
| WO | WO 2016/141291 A1 | 9/2016 |
| WO | WO 2016/152378 A1 | 9/2016 |
| WO | WO 2016/152415 A1 | 9/2016 |
| WO | WO 2016/178222 A1 | 11/2016 |
| WO | WO 2016/122305 A1 | 12/2016 |
| WO | WO 2017/015047 A1 | 1/2017 |
| WO | WO 2017/042825 A2 | 3/2017 |
| WO | WO 2017/074674 A1 | 5/2017 |
| WO | WO 2017/074676 A1 | 5/2017 |
| WO | WO 2017/074684 A1 | 5/2017 |
| WO | WO 2017/074685 A2 | 5/2017 |
| WO | WO 2017/075320 A1 | 5/2017 |

(56) References Cited

FOREIGN PATENT DOCUMENTS

| | | |
|---|---|---|
| WO | WO 2017/105202 A1 | 6/2017 |
| WO | WO 2017/139114 A1 | 8/2017 |
| WO | WO 2017/139224 A1 | 8/2017 |
| WO | WO 2017/165831 A1 | 9/2017 |
| WO | WO 2017/174851 A1 | 10/2017 |
| WO | WO 2017/197367 A1 | 11/2017 |
| WO | WO 2018/075499 A1 | 4/2018 |
| WO | WO 2018/106654 A1 | 6/2018 |
| WO | WO 2017/051801 A1 | 7/2018 |
| WO | WO 2018/191361 A1 | 10/2018 |
| WO | WO 2018/217781 A1 | 11/2018 |
| WO | WO 2019/010119 A1 | 1/2019 |
| WO | WO 2013/086099 A1 | 6/2019 |
| WO | WO 2019/119935 A1 | 6/2019 |
| WO | WO 2020/160318 A1 | 8/2020 |

OTHER PUBLICATIONS

Alekseyev, Sonya, et al. "Prolonging the life of a patient's IV: an integrative review of intravenous securement devices." Medsurg nursing 21.5 (2012).

Bastian, Dallas, "Better dressings needed to curb PIVC failures," Nursing Review, Jul. 27, 2018, 3 pages.

Grau, Delphine, et al. "Complications with peripherally inserted central catheters (PICCs) used in hospitalized patients and outpatients: a prospective cohort study." Antimicrobial Resistance & Infection Control 6.1 (2017): 1-8.

Hedayatinejad, Maryam, et al. "Survey of complications of peripheral venous catheterization at an Intensive Care Unit of (ICU) of Susa city." Jentashapir J Health Res [Internet] (2016).

Helm, Robert E., et al. "Accepted but unacceptable: peripheral IV catheter failure." Journal of Infusion Nursing 38.3 (2015): 189-203.

Marsh, Nicole, et al. "Observational study of peripheral intravenous catheter outcomes in adult hospitalized patients: a multivariable analysis of peripheral intravenous catheter failure." Journal of Hospital Medicine 13.2 (2017): E1-E7.

Piper, Russell, et al. "The mechanistic causes of peripheral intravenous catheter failure based on a parametric computational study." Scientific Reports 8.1 (2018): 1-12.

Rickard, Claire M., et al. "Securing All intravenous devices Effectively in hospitalised patients—the SAVE trial: study protocol for a multicentre randomised controlled trial." BMJ open 5.9 (2015): e008689.

Schneider Jr, Laura Valbousquet, et al. "Evaluation of PICC complications in orthopedic inpatients with bone infection for long-term intravenous antibiotics therapy." The journal of vascular access 16.4 (2015): 299-308.

Takahashi, Toshiaki, et al. "Preventing peripheral intravenous catheter failure by reducing mechanical irritation." Scientific reports 10.1 (2020): 1-13.

Zhang, Li, et al. "Infection risks associated with peripheral vascular catheters." Journal of infection prevention 17.5 (2016): 207-213.

Search Report and Written Opinion received in International Application No. PCT/US2021/064998, dated Apr. 27, 2022, in 19 pages.

European Search Report received in Application No. 17888827.7, dated Aug. 13, 2020.

Search Report and Written Opinion in International Application No. PCT/US2017/068343 dated Apr. 13, 2018 in 16 pages.

Search Report and Written Opinion in International Application No. PCT/US2019/038208 dated Oct. 18, 2019, in 26 pages.

* cited by examiner

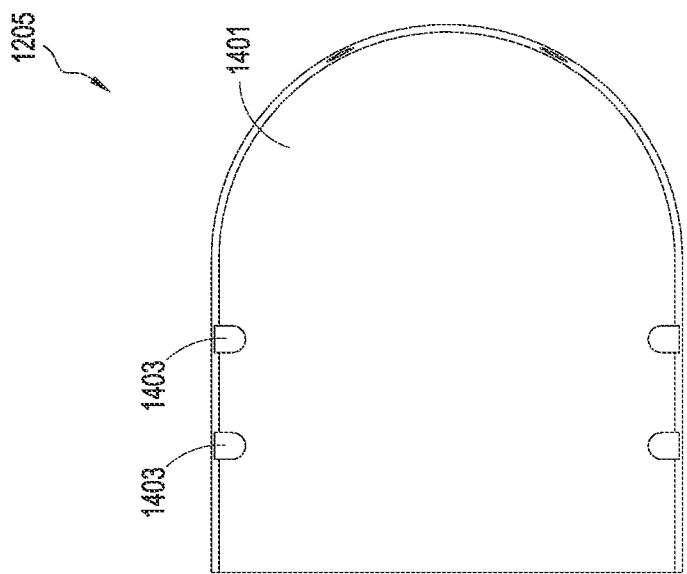
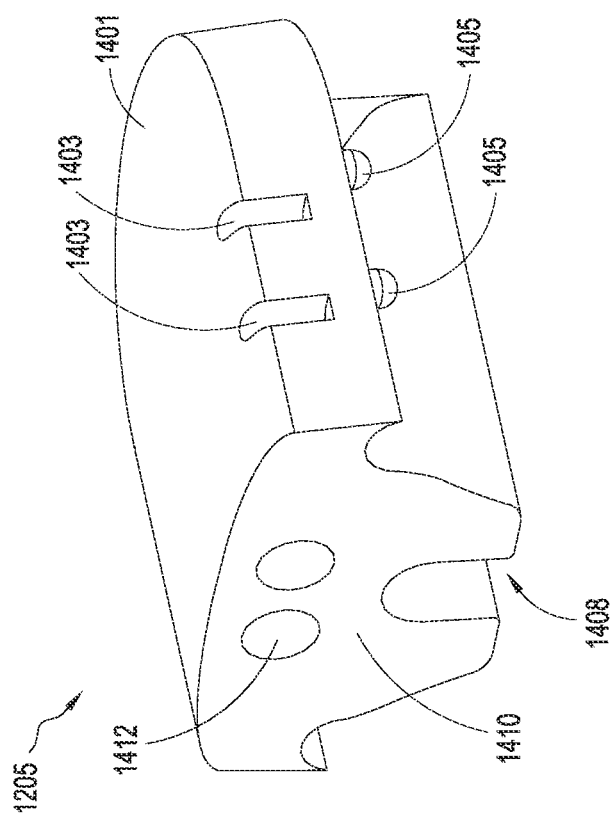
FIG. 14B
FIG. 14A

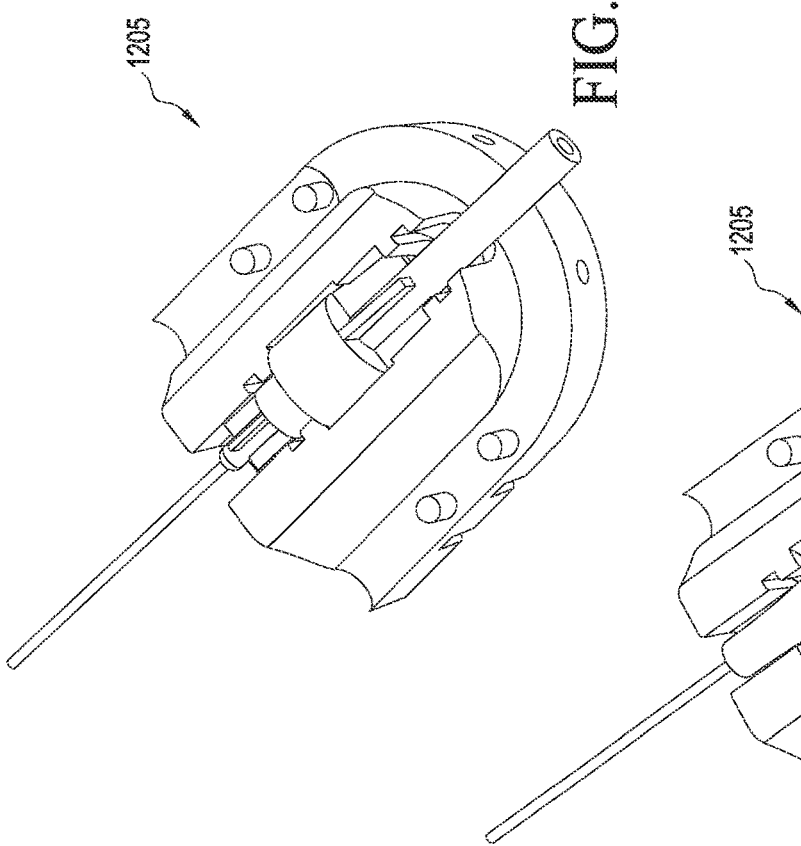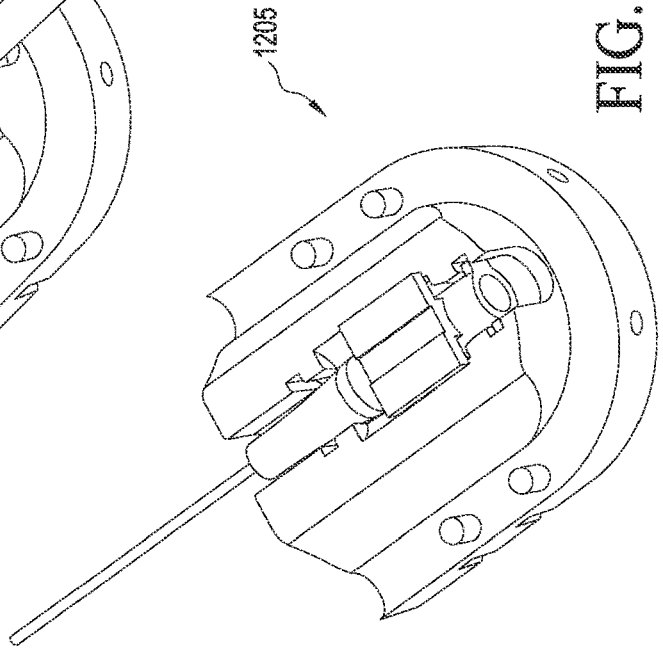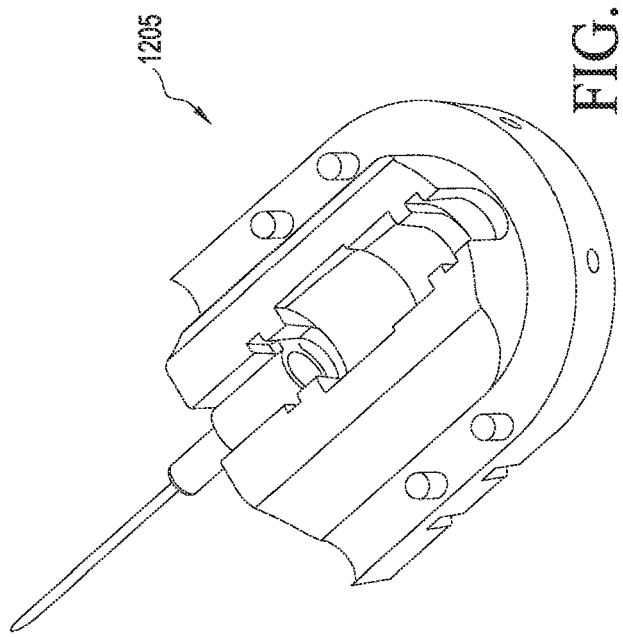

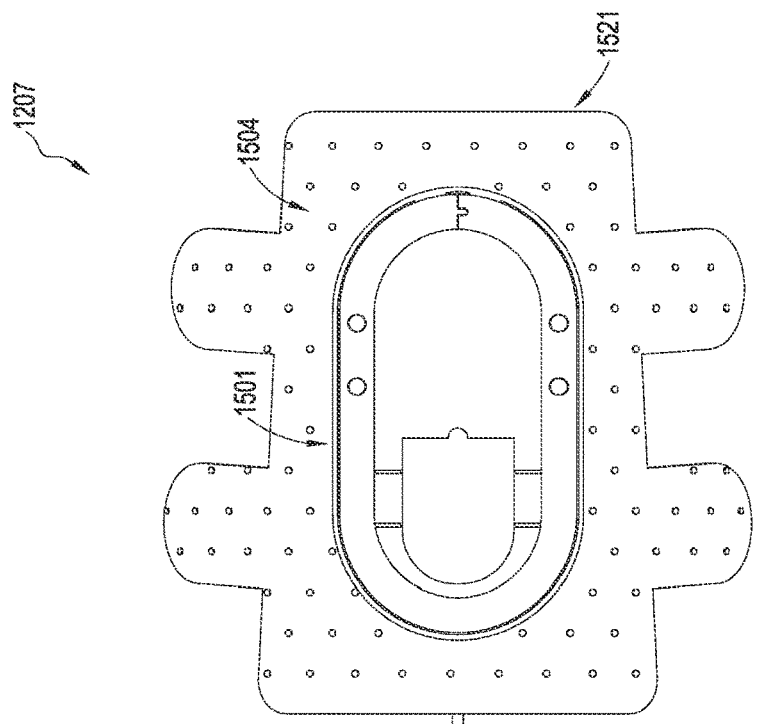
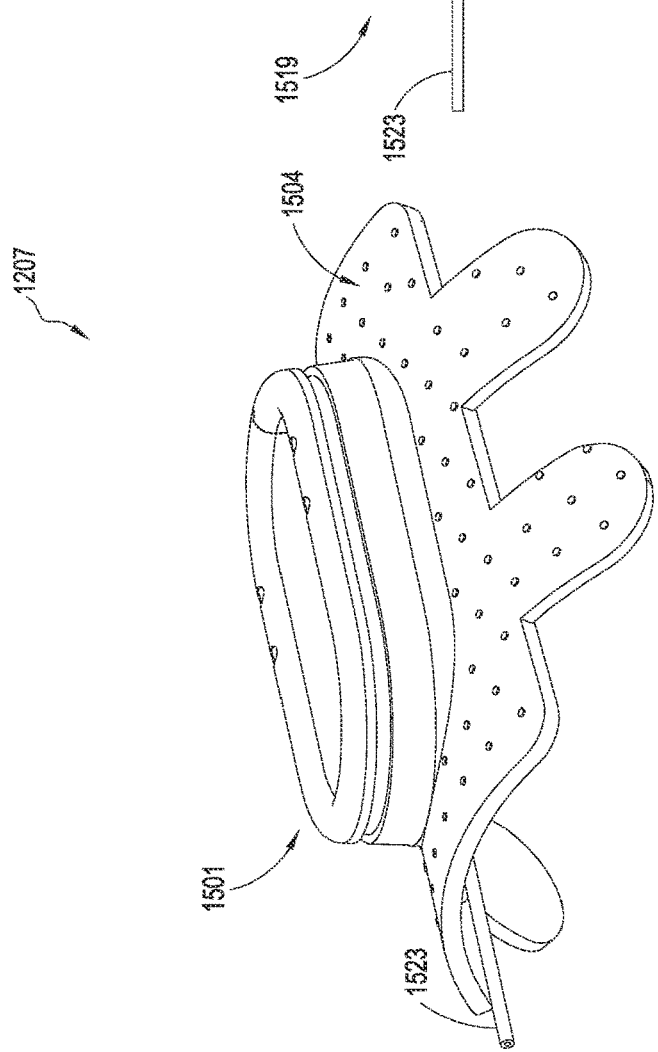
FIG. 15B
FIG. 15A

CATHETER HOUSING

INCORPORATION BY REFERENCE TO ANY PRIORITY APPLICATIONS

This application is a continuation of U.S. patent application Ser. No. 16/204,689, filed Nov. 29, 2018, titled CATHETER HOUSING, which is a continuation of U.S. patent application Ser. No. 15/853,469, filed Dec. 22, 2017, titled CATHETER HOUSING, which claims the benefit of U.S. Provisional Application No. 62/439,302, filed Dec. 27, 2016, titled CATHETER STABILIZER. The entire contents of the above-identified patent applications are incorporated by reference herein.

TECHNICAL FIELD

In general, the present disclosure relates to catheter stabilization or securement devices.

BACKGROUND

Intravenous catheter care has been used on patients for hundreds of years. Peripheral intravenous catheter (herein referred to collectively as "IV catheter") placement is one of the most common invasive procedures performed on patients. After cleaning a catheter site, a catheter needle is inserted into a vein of a patient. However, traditional methods of cleaning the catheter insertion site (for example, a quick swabbing of the insertion region by an alcohol swab or other antiseptic solution) are inadequate to eliminate risks of contamination or infection. Germs and bacteria commonly inhabit layers of the skin underneath the surface layer. For example, up to 80% of resident microorganisms can inhabit the first 5 layers of the skin's stratum corneum, and up to 20% of the remaining microorganisms exist in biofilms in the underlying epidermal and dermal layers and sebaceous glands. Traditional techniques of applying an adhesive film dressing therefore will cover and incubate such germs at or near the insertion site. Such contamination can lead to various infections and complications, such as blood stream infection and/or phlebitis, among others. Furthermore, traditional adhesive catheter securement techniques inhibit normal skin respiration and/or ventilation processes and also raise the humidity and/or temperature levels underneath the adhesive materials. This in turn can also promote microorganism growth.

Another disadvantage of traditional catheter securement devices and techniques is that firmly fixing the catheter device to a patient's skin results in the catheter cannula tip being improperly angled within the vein and/or vein wall or lumen such that the cannula tip can erode or otherwise cause damage to the vein and/or vein wall orlumen and/or surrounding regions. Such erosion or other damage can be exacerbated when the patient moves or the catheter cannula tip is otherwise altered in its angle or position. In traditional approaches, after inserting a needle and/or catheter into a patient. A care provider typically applies a series of tapes in order to stabilize the catheter in an attempt to prevent catheter movement. Unfortunately, IV catheters applied in this manner have a very high failure rate. These failures are due to a variety of reasons including mechanical failures or occlusion, dislodgment, infection, phlebitis (inflammation of the vein that can lead to blood clots), and infiltration to surrounding tissue. Moreover, even without any of these failures, commonly accepted practice requires the removal of catheters after a 72-96 hour dwell time. Thus, even under the best circumstances, catheters have a relatively short life span that requires frequent adjustment and/or movement. Catheter failures and frequent catheter movement can result in costly catheter replacements and eventually to venous depletion. Venous depletion leads to more invasive, risky, and costly venous access devices.

SUMMARY

The present disclosure relates to an IV catheter or arterial catheter housing system which provides stabilization, disinfection, local anesthetic and/or digital monitoring vital signs. The housing system can reduce catheter failure and can extend catheter dwell time beyond the current standard dwell period. Stabilizing a catheter is of critical importance. For example, phlebitis is commonly caused by movement of the catheter relative to the vessel wall. In other examples, catheters can become dislodged from patients due to patient movement or can be pushed further into a patient's arm or other body part, potentially dislodging it from a vein or other tissue and disrupting fluid flow. Moreover, catheters that move in and out of the skin can cause an increased risk of bacterial infection. While tapes used to stabilize catheters are considered the common standard of care, tapes introduce a number of drawbacks that are solved by the present disclosure. It is difficult to maintain a proper angle of a catheter needle with tape. Tape adhesives can also cause irritation to patient skin, particularly when worn for an extended period of time. Compounding this problem, tapes obscure the insertion site and can prevent assessment of IV catheter complications. Tapes can also prevent proper ventilation of areas near and/or surrounding the insertion site, which, among other things, can decrease patient comfort. Moreover, it has been found that tapes on or near the insertion site can introduce and/or incubate bacteria, leading to infections and catheter failure.

The catheter housing devices (also referred to as "catheter stabilizing device" and "catheter housing" herein) and methods described herein can include various disinfection or sterilization methods and components. For example, when fully assembled, the catheter housing can be supplied with sterilizing inert gas which can suffocate microbes or other contaminants in and around the catheter and needle insertion site, including a hub portion of a catheter and a fluid tube. Various components of the catheter housing can be structured to form a hermetic seal which can advantageously inhibit or prevent microbes or other contaminants from entering portions of the catheter housing. The catheter housing device can include a gas line or port which can be used to provide sterilizing gases. Additionally, other gases can be provided in the manner described above, such as local anesthetics. For example, soothing, anesthetic, or similar vapor drugs can be provided to the catheter housing device in a gaseous form to aid healing or reconstruction in and around the insertion site.

The catheter housing devices described herein can also include various sensors, including bio-sensors that can measure, gather, and transmit patient medical condition data. The bio-sensors can include a micro-processor. For example, the bio-sensors can include an illuminated LCD monitor for detecting, measuring, storing and/or displaying patient vital functions, including venous and arterial blood pressure, heart beats, blood oxygen levels, general and topical temperature, and local tissue humidity, and/or venous blood current speed, among others. The measurements and/or calculations performed and/or taken by these sensors can be stored on a flash storage memory positioned on the catheter housing system. Alternatively, the sensor measurements can be wirelessly transmitted to a patient monitoring system for display to a care provider or user.

The catheter housing devices and methods described herein can avoid using adhesives to secure a catheter or portion thereof or connected to a catheter to a patient's skin. The catheter housing devices and methods described herein can also avoid applying pressure directly to the needle. This can dramatically reduce the potential for contamination in and/or around the insertion site. Moreover, because the catheter is not covered with tape, the insertion area remains readily visible to a care provider. This visibility allows the care provider to easily, quickly and repeatedly assess the insertion site for signs of inflammation, failure or infection. The stabilization system also mechanically isolates the catheter from patient movement and holds the catheter at a proper or natural insertion angle. The catheter housing devices and methods described herein can also provide a securement system that is highly skin breathable, allowing for patient comfort and reduced skin irritation.

As discussed herein, the catheter housing device can stabilize a catheter on a patient without using adhesives or applying direct pressure to a catheter insertion site. The catheter housing device (also referred to as "catheter housing" herein) can include a hub, a catheter lock, a cover, and a band. In some alternative designs, the hub comprises a main body configured to at least partially surround a catheter insertion site, and the main body can include at least one port or opening which allows catheter tubing outside of the main body to connect to a catheter inside the main body. The catheter lock can comprise a body configured to engage with the main body of the hub and a securement recess, wherein the securement recess can be configured to receive at least a portion of the catheter, and wherein the securement recess can be configured to stabilize the catheter. The cover can be configured to engage with and fit on a top of the hub. Further, the band can be configured to secure the stabilizing device to the patient. In some alternative designs, the securement recess of the catheter housing device can comprise a hook. The securement recess can also be an opening sized and shaped to fit at least a portion of the catheter in a friction fit. The securement recess can be configured to rotate relative to the body of the catheter lock. This rotation can be limited to a range of 1 to 20 degrees of rotation relative to the body of the catheter lock. The hub of the catheter housing device can comprise an inner groove extending along an inner surface of the main body, and wherein the lock body further comprises a rib configured to engage the inner groove of the hub. The catheter lock of the catheter housing device can comprise a raised sealing structure, wherein the raised sealing structure extends along one side of an interior region of the lock body and is spaced apart from a base of the lock body, and wherein the raised sealing structure is configured to create a compartment surrounding the insertion site. The band of the catheter housing device can be configured to secure the stabilizing device to the patient without chemical adhesives. The band of the catheter housing device can comprise a plurality of contacting structures configured to space the band from direct contact with the patient's skin. In some alternative designs, the plurality of contact structures can comprise one or more of a suction cup or a corrugated strip. The band can comprise at least one sensor for measuring a physiological parameter of the patient. The band can comprise a plurality of arms configured to wrap around an appendage or other body portion of the patient and secure the hub to the patient. The band can comprise an opening configured to fit around a perimeter of the main body of the hub. In some alternative designs, the cover of the catheter housing device comprises a window configured to facilitate viewing of an interior of the device. The hub of the catheter housing device can comprise a flange configured to surround the main body and lay flat against skin of the patient surrounding the insertion site. The hub can be made of flexible silicon. The catheter lock of the catheter housing device can be made of a rigid material.

A method for stabilizing a catheter without using adhesives and without applying direct pressure to a patient insertion site can include: placing a stabilizing device on a patient around a catheter insertion site, the stabilizing device including a hub including a main body and an outer membrane connected to a bottom portion of the main body and configured to lay flat against skin of a patient; connecting a lock body to the hub and the catheter such that the lock body holds at least a portion of the catheter body in a notch configured to receive a portion of the catheter, wherein the lock body is configured to reduce movement of the catheter with respect to the patient; placing a band with an aperture sized and shaped to receive the hub over the hub such that the hub is received within the aperture; and securing the band to the patient without adhesives. The connecting of the lock body to the hub can comprise fitting a rib of the lock body into an inner groove of the hub. The securing step can be performed by wrapping at least a portion of the band around the patient's arm. The band can comprise a plurality of contacting structures configured to space the band from direct contact with the patient's skin. The plurality of contact structures can comprise one or more of a suction cup or a corrugated strip. In some alternative designs, the cover and lock body can comprise a transparent or translucent material. The band can comprise a plurality of arms configured to wrap around an arm of the patient and secure the hub to the patient. The securing of the band can comprise securing less than all of the plurality of arms. The sealing mechanism can be configured to maintain a seal around a portion of the catheter as the catheter passes through the sealing mechanism.

In some alternative designs, a catheter housing device which houses a catheter inserted into a patient at an insertion site can comprise a hub component, a catheter lock component, a cover, and at least one fastening strap. The hub component can be configured to at least partially surround the catheter insertion site on the patient and secure to the patient. The catheter lock component can be configured retain the catheter within the hub component. The cover can be configured to at least partially enclose the catheter lock component and secure to at least a portion of the hub component. The at least one fastening strap can be configured to wrap around at least a portion of the patient's body and secure to at least a portion of the hub component. In some alternative designs, the at least one fastening strap of the catheter housing device can comprise a first partial-length fastening strap and a second partial-length fastening strap, wherein the first partial-length fastening strap being can be configured to secure to at least a portion of the hub component and at least a portion of the second partial-length fastening strap, the second partial-length fastening strap configured to secure to at least a portion of the hub component and at least a portion of the first partial-length fastening strap. The at least one fastening strap can comprise at least one corrugated protrusion along a portion of the at least one fastening strap that contacts the patient's skin. The catheter housing device can comprise at least one sensor located on a member selected from the group consisting of the hub component, the catheter lock component, the cover, and the at least one fastening strap. The at least one sensor can be selected from the group consisting of a temperature sensor, a blood pressure sensor, a blood oxygen saturation sensor, a sensor for liquid and blood leakage, and a skin humidity sensor. In some alternative designs, the cover of the catheter housing device can comprise a slot configured to allow at least a portion of the catheter to pass through the cover. The cover can comprise at least one tube holder configured to secure at least one catheter tube and/or gas tube. The cover can comprise a material selected from the group consisting of plastic, rubber, and silicone. The cover can be substantially waterproof and shockproof. The cover can comprise a transparent material. The cover can comprise a shape selected from the group consisting of trapezoidal, rectangular, square, oval, and circular. The cover can comprise at least one port configured to permit gas to flow into an interior of the cover. The cover can comprise at least one interior notch located along an interior portion of the cover and the catheter lock component can comprise at least one slot configured to secure to the at least one interior notch of the cover when the cover is placed over a portion of the catheter lock component and secured to the catheter lock component. In some alternative designs, the catheter housing device can include at least one port which comprises an opening and at least one port rim, wherein the opening extends outwardly from the cove and the at least one port rim extends radially outward from the opening. The at least one port rim can be configured to secure to a portion of a gas tube in a configuration selected from the group consisting of a snap-fit, a press fit, and a friction fit. In some alternative designs, the catheter housing device can include a catheter lock component which comprises a top portion and a bottom portion, wherein the bottom portion comprises a recess configured to secure the catheter. The recess of the bottom portion can comprise at least one groove configured to secure at least a portion of the catheter. Alternatively, the recess of the bottom portion can comprise a front groove, a back groove, and a middle groove positioned between the front groove and the back groove, wherein the front groove can be configured to secure a first portion of the catheter, the back groove can be configured to secure a second portion of the catheter, and the middle groove can be configured to secure a third portion of the catheter. The middle groove can be angled such that the third portion of the catheter is inclined at an angle when secured by the middle groove. In some alternative designs, the catheter housing device can include a catheter lock component which comprises a top portion and a bottom portion, wherein the bottom portion comprises a first jaw and a second jaw and a cavity in between the first jaw and second jaw, wherein the cavity can be configured to secure at least a portion of the catheter. The first jaw and the second jaw can comprise corresponding grooves configured to secure at least a portion of the catheter at an inclined angle. The cover of the catheter housing device can comprise at least one protrusion located along an interior portion of the cover, and the hub component can comprise at least one peripheral groove configured to secure to the at least one protrusion when the cover is placed over a portion of the hub component and secured to the hub component. The cover can be configured to form a hermetic seal when the cover is secured to the hub component. The catheter lock component of the catheter housing device can comprise at least one pin located on a bottom portion of the catheter lock component, wherein the catheter lock component can be configured to secure to the hub component when the at least one pin secures to an at least one recess located on a portion of the hub component. The catheter lock component can comprise a lip on a bottom portion of the catheter lock component, wherein the lip can be configured to accommodate a portion of the hub component when the catheter lock component is placed atop a portion of the hub component. The catheter lock component can comprise at least one light configured to illuminate a region proximate to the catheter housing device. In some alternative designs, the hub component of the catheter housing device can comprise a main body, a membrane, and an opening in the membrane, wherein the membrane can be configured to secure to the main body and contact at least a portion of the patient's skin, and the opening in the membrane can be positioned around the insertion site. The membrane can comprise at least one arm configured to extend outwardly from a body of the membrane, wherein the at least one arm can be further configured to secure to the at least one fastening strap. The membrane can comprise a top surface and a bottom surface, wherein at least a portion of the top surface can comprise an attachment structure configured to secure to the at least one fastening strap. The attachment structure can be selected from the group consisting of hook and loop fasteners, buckles, and fungi-like attachment. The main body of the hub component can comprise at least one inlet configured to receive a portion of the catheter. The main body can comprise at least one joint configured to be flexibly opened and closed to permit a portion of the catheter to more easily pass through the at least one inlet. The main body and/or the membrane can comprise a transparent material. The main body and/or the membrane can comprise at least one indicator proximate to the insertion site. The main body and/or the membrane can comprise a material selected from the group consisting of plastic, rubber, and silicone. The membrane can be configured to form a hermetic seal around the insertion site on the patient's skin. The membrane can comprise at least one sensor selected from the group consisting of a temperature sensor, a blood pressure sensor, a blood oxygen saturation sensor, a sensor for liquid and blood leakage, and a skin humidity sensor. The membrane can comprise a top layer, a base layer, and a middle layer in between the top layer and the base layer, wherein the top layer can be coupled to the middle layer, the middle layer can be coupled to the base layer, the base layer located adjacent to the patient's skin. The membrane can include a gas line and the base layer can comprise at least one perforated loop tube coupled to the gas line. Gas can be permitted to flow from the gas line through the at least one perforated loop tube to at least a portion of the patient's skin. The base layer of the membrane can comprise a corrugate structure and/or at least one suction cup configured to at least partially secure to the patient's skin. The middle layer of the membrane can be thicker than the top layer and/or the base layer, and the middle layer can comprise a stronger material than the top layer and/or the base layer.

A method for stabilizing a catheter to a patient can include: placing a hub component on the patient wherein the hub component surrounds a catheter insertion site; connecting a catheter lock component to at least a portion of the catheter and the hub component; and securing at least one fastening strap to the hub component and to the patient without using adhesives. The method can comprise securing a cover to the hub component to enclose the catheter insertion site. The method can comprise connecting a gas line to an at least one port that can be located on the cover and permitting gas to flow into an interior of the cover. The cover can comprise at least one interior notch located along an interior portion of the cover and the catheter lock component can comprise at least one slot, wherein the method can include securing the cover to the catheter lock component by securing the at least one interior notch to the at least one slot. The cover can comprise at least one protrusion located along an interior portion of the cover and the hub component can comprise at least one peripheral groove, wherein the cover is secured to the hub component according to the method by securing the at least one protrusion to the at least one peripheral groove. The securing of the cover to the hub component according to the method can form a hermetic seal. The catheter lock component can comprise at least one pin located on a bottom portion of the catheter lock component and the hub component can comprise at least one recess, wherein the catheter lock component is secured to the hub component according to the method by securing the at least one pin to the at least one recess. The catheter lock component can comprise a top portion and a bottom portion, the bottom portion including a recess, wherein the catheter lock component can be connected to at least a portion of the catheter according to the method by securing at least a portion of the catheter to the recess. The hub component can comprise an inlet, wherein, when the catheter lock component secures at least a portion of the catheter and secures to the hub component according to the method, at least a portion of the catheter is positioned through the inlet. The at least one fastening strap can comprise at least one corrugated protrusion along a portion of the at least one fastening strap that contacts the patient's skin when the catheter is stabilized to the patient according to the method. The at least one fastening strap can comprise a first partial-length fastening strap and a second partial-length fastening strap, wherein the method can further comprise securing the first partial-length fastening strap to the hub component and at least a portion of the second partial-length fastening strap and securing the second partial-length fastening strap to the hub component and at least a portion of the first partial-length fastening strap. The method can comprise measuring a physiological parameter of the patient from an at least one sensor located on a member selected from the group consisting of the hub component, the catheter lock component, and the at least one fastening strap. The hub component can comprise a main body and a membrane positioned around the catheter insertion site, the membrane positioned to contact the patient's skin, wherein the catheter lock component can be connected to the main body of the hub component and the at least one fastening strap can be secured to the membrane according to the method. The membrane of the hub component can comprise at least one perforated loop tube and a gas line connected to the at least one perforated loop tube, wherein the method can further comprise permitting gas to flow through the gas line and the at least one perforated loop tube to at least partially contact the patient's skin.

In some alternative designs, a catheter housing device which houses a catheter inserted into a patient at an insertion site can comprise a housing and a catheter lock component. The housing can be configured to surround and enclose the insertion site, wherein the housing does not touch skin of the patient at the insertion site, and the housing can include an opening that allows catheter tubing to be inserted into the housing. The catheter lock component can be configured to secure at least a portion of the catheter. The catheter housing device can comprise at least one fastening strap configured to wrap around at least a portion of the patient's body and secure to at least a portion of the housing. The catheter housing device can comprise at least one arm extending outwardly from the housing, and the at least one fastening strap can be configured to secure to the at least one arm of the housing. The at least one arm can include Velcro and the at least one fastening strap can include Velcro, wherein, when the at least one fastening strap is configured to secure to the at least one arm of the housing, the Velcro of the at least one arm attaches to the Velcro of the at least one fastening strap. The at least one fastening strap can comprise a first partial-length fastening strap and a second partial-length fastening strap, and the first partial-length fastening strap can be configured to secure to at least a portion of the housing and at least a portion of the second partial-length fastening strap, and the second partial-length fastening strap can be configured to secure to at least a portion of the housing and at least a portion of the first partial-length fastening strap. The at least one fastening strap can comprise at least one corrugated protrusion along a portion of the at least one fastening strap that contacts the patient's skin when the at least one fastening strap is wrapped around at least a portion of the patient's body. The catheter housing device can comprise at least one sensor located on a member selected from the group consisting of the housing and the catheter lock component. The at least one sensor can be selected from the group consisting of a temperature sensor, a blood pressure sensor, a blood oxygen saturation sensor, a sensor for liquid and blood leakage, and a skin humidity sensor. The housing of the catheter housing device can comprise a slot which can be configured to allow at least a portion of the catheter to pass from the catheter lock component outwardly through the housing. The housing can comprise at least one tube holder which can be configured to secure at least one catheter tube, and the catheter tube can be configured to connect with the catheter. The catheter housing device can comprise a material selected from the group consisting of plastic, rubber, and silicone. The catheter housing device can be substantially waterproof and shockproof. The catheter housing device can comprise a transparent material. The housing can comprise a shape selected from the group consisting of trapezoidal, rectangular, square, oval, and circular. The housing can comprise at least one port configured to permit gas to flow through the housing and to the insertion site. The at least one port can comprise an opening and at least one port rim, and the opening can extend outwardly from the housing, and the at least one port rim can extend radially outward from the opening. The at least one port rim can be configured to secure to a portion of a gas tube in a configuration selected from the group consisting of a snap-fit, a press fit, and a friction fit. The catheter lock component can include a top portion and a bottom portion, wherein the bottom portion can comprise a recess configured to secure the catheter. The recess of the bottom portion can comprise at least one groove configured to secure at least a portion of the catheter. The recess of the bottom portion can include a first groove and a second groove, wherein the second groove can be larger than the first groove, and the first groove can be configured to secure a first portion of the catheter, and the second groove can be configured to secure a second portion of the catheter. The second groove can be angled such that, when the second portion of the catheter is secured by the second groove, the catheter is inclined at an angle. The second groove can be angled such that, when the second portion of the catheter is secured by the second groove, the catheter is inclined at an angle between 1 and 25 degrees. The catheter housing device can form a hermetic seal around the insertion site. The catheter housing device can comprise at least one light located on the member selected from the group consisting of the housing and the catheter lock component. The housing can comprise at least one indicator located on a portion of the housing proximate to the opening in the housing. The catheter housing device can comprise a membrane coupled to the housing that extends around the housing and around the insertion site and at least partially contacts the patient's skin. The membrane can comprise at least one perforated loop tube and a gas line connected to the at least one perforated loop tube that can be configured to permit gas to flow through the gas line and the at least one perforated loop tube to at least partially contact the patient's skin. The membrane can comprise a corrugated structure. The membrane can comprise at least one suction cup configured to secure to the patient's skin. The membrane can include a bottom surface and a top surface, wherein at least a portion of the top surface can comprise a first attachment structure configured to secure to a second attachment structure on an at least one fastening strap. The first and second attachment structures can be selected from the group consisting of hook and loop fasteners, buckles, and fungi-like attachment. The membrane can comprise a top layer, a base layer, and a middle layer in between the top layer and the base layer, wherein the top layer can be coupled to the middle layer, the middle layer can be coupled to the base layer, and the base layer can be located adjacent to the patient's skin. The membrane can comprise a gas line, wherein the base layer can include at least one perforated loop tube coupled to the gas line. The base layer can comprise a corrugated structure. The base layer can comprise at least one suction cup that can be configured to at least partially secure to the patient's skin. The middle layer can be thicker than the top layer and/or the base layer, and the middle layer can comprise a stronger material than the top layer and/or the base layer.

A method of stabilizing a catheter to a patient at an insertion site can comprise: placing a catheter housing device on the patient wherein the catheter housing device surrounds and encloses the catheter insertion site, the catheter housing device including an opening positioned around the insertion site and a catheter stabilizing component, wherein the opening is configured to allow catheter tubing to be inserted into the catheter stabilizing component; connecting the catheter stabilizing component to at least a portion of the catheter; and securing the catheter housing device to the patient without using adhesives. The securing of the catheter housing device to the patient can comprise securing at least one fastening strap to the patient and attaching the at least one fastening strap to the catheter housing device. The catheter housing device of the method can comprise at least one arm, wherein securing the catheter housing device to the patient can comprise securing the at least one arm to the patient and attaching the at least one arm to the catheter housing device. The catheter housing device of the method can comprise at least one port, wherein the method further can comprise attaching at least one gas line to the at least one port and permitting gas to flow to the insertion site. The gas permitted to flow to the insertion site can be sterilizing gas and/or anesthetic gas. The catheter housing device of the method can include a top surface and a bottom surface, wherein the bottom surface comprises at least one recess, wherein connecting the catheter stabilizing component to at least a portion of the catheter comprises securing the catheter to the at least one recess. The at least one recess of the bottom surface can comprise at least two grooves configured to secure different portions of the catheter. The at least one recess of the bottom surface can comprise a first groove and a second groove larger than the first groove, the first groove can be configured to secure a first portion of the catheter, and the second groove can be configured to secure a second portion of the catheter. The second groove can be angled such that, when the second portion of the catheter is secured by the second groove, the catheter is inclined at an angle between 1 and 25 degrees.

A universal catheter stabilization device which stabilizes a range of different catheter types can comprise at least one recess extending along a direction from a front portion to a back portion of the catheter stabilization device, wherein the at least one recess can include at least a first groove sized and shaped to secure a first type of catheter and a second groove sized and shaped to secure a second type of catheter, wherein the first type of catheter and the second type of catheter are different types of catheters having different physical dimensions. The first groove and the second groove can occupy substantially the same space. The first groove and the second groove can be formed in a single recess. The first groove and the second groove can be formed in a different recess. The universal catheter stabilization device comprise one recess. The first groove can be positioned near the front portion of the catheter lock, and the second groove can be positioned near the back portion of the catheter lock, and a third groove can be positioned between the first groove and the second groove. The third groove can be longer than the first groove and/or the second groove. The third groove can be longer than the first groove and/or the second groove, and the third groove can comprise at least two sub-grooves, wherein the at least two sub-grooves are angled differently. The first groove can be configured to secure a first portion of the catheter and the third groove can be configured to secure a second portion of the catheter, wherein the second portion of the catheter is larger than the first portion. The first groove of the recess can be inclined, wherein, when at least a portion of the catheter is secured to the first groove of the recess, the catheter can be in an inclined position. When the at least a portion of the catheter is secured by the first groove of the recess, the catheter can be inclined at an angle between 1 and 25 degrees. The first groove and/or the second groove can have an upper portion and a lower portion, and the upper portion can have a wider surface than the lower portion. The first groove and/or the second groove can have an upper portion and a lower portion, and the lower portion can have a wider surface than the upper portion. The first groove can have a deeper recess than the second groove. The second groove can have a deeper recess than the first groove.

A method of securing a portion of a catheter to a catheter stabilizing device can comprise: providing a catheter; providing a catheter stabilizing device including at least one recess extending along a direction from a front portion to a back portion of the catheter stabilizing device, the at least one recess including at least one groove sized and shaped to secure the catheter; and securing the catheter with the at least one groove of the at least one recess. The at least one groove can comprise a first groove sized and shaped to secure a first type of catheter and a second groove sized and shaped to secure a second type of catheter, wherein the first type of catheter and the second type of catheter are different types of catheters having different physical dimensions. The at least one groove can be angled such that, when the catheter is secured by the at least one groove, the catheter is inclined at an angle between 1 and 25 degrees. The at least one groove can comprise a front groove positioned near the front portion of the catheter lock and a back groove positioned near the back portion of the catheter lock, wherein the securing of the catheter by the recess can include securing a first portion of the catheter with the front groove and securing a second portion of the catheter with the back groove. The at least one groove can comprise a front groove positioned near the front portion of the catheter lock, a back groove positioned near the back portion of the catheter lock, and a middle groove positioned between the front groove and the back groove, wherein the securing of the catheter by the recess can comprise securing a first portion of the catheter with the front groove and securing a second portion of the catheter with the middle groove, wherein the second portion of the catheter is larger than the first portion of the catheter. The at least one groove can comprise a front groove positioned near the front portion of the catheter lock, a back groove positioned near the back portion of the catheter lock, and a middle groove positioned between the front groove and the back groove, wherein the securing of the catheter by the recess can comprise securing a first portion of the catheter with the back groove and securing a second portion of the catheter with the middle groove, wherein the second portion of the catheter is larger than the first portion of the catheter. The at least one recess can comprise a front groove positioned near the front portion of the catheter lock, a back groove positioned near the back portion of the catheter lock, and a middle groove positioned between the front groove and the back groove, wherein the securing of the catheter by the recess can comprise securing a first portion of the catheter with the front groove and securing a second portion of the catheter with the back groove and securing a third portion of the catheter with the middle groove.

A catheter housing device which houses a catheter inserted into a patient at an insertion site and seals the insertion site from contamination can comprise: a housing including an opening that allows catheter tubing to be inserted into the housing, the housing configured to surround and enclose the insertion site and form a hermetic seal when the housing is secured to the patient; a catheter lock component configured to secure at least a portion of the catheter; and at least one port coupled to the housing and configured to permit gas to flow to the insertion site. The at least one port can be configured to permit sterilizing gas to the insertion site. The at least one port can be configured to permit ethylene oxide gas to flow to the insertion site. The at least one port can be configured to permit hydrogen peroxide gas plasma to flow to the insertion site. The at least one port can be configured to permit anesthetic gas to flow to the insertion site. The at least one port can be configured to permit both anesthetic and sterilizing gas to flow to the insertion site. The at least one port can comprise a first port and a second port, wherein the first port can be configured to permit anesthetic gas to flow to the insertion site, and the second port can be configured to permit sterilizing gas to flow to the insertion site.

A method of securing a catheter to a patient near an insertion site and sealing the insertion site from contamination can comprise: placing a catheter housing device around the insertion site on the patient, the catheter housing device including a housing, a catheter lock component, and at least one port coupled to the housing; securing the catheter with the catheter lock component of the catheter housing device; and securing the catheter housing device to the patient to form a hermetic seal around the insertion site. The catheter housing device of the method can include at least one arm comprising a first attachment structure, and the housing can include a second attachment structure, wherein the securing the catheter housing device to the patient can comprise wrapping the at least one arm of the catheter housing device around a portion of the patient's body and securing the first attachment structure of the at least one arm to the second attachment structure of the housing. The first attachment structure and the second attachment structure can be selected from the group consisting of hook and loop fasteners, buckles, and fungi-like attachment. The method can comprise attaching a gas line to the at least one port and permitting gas to flow from the gas line through the at least one port and to the insertion site. The gas permitted to flow from the gas line through the port and to the insertion site can be sterilizing gas, ethylene oxide gas, hydrogen peroxide gas, anesthetic gas, or a combination of these or other gases. The at least one port can include a first port and a second port, wherein the method can comprise attaching a first gas line to the first port and permitting gas to flow from the gas line through the first port and to the insertion site, and attaching a second gas line to the second port and permitting gas to flow from the second gas line through the second port and to the insertion site. Anesthetic gas can be provided to the first gas line and sterilizing gas can be provided to the second gas line.

A catheter housing device which houses a catheter inserted into a patient at an insertion site can comprise: a housing configured to surround the catheter insertion site on the patient and secure to the patient, wherein the housing can be configured to stabilize the catheter and reduce the likelihood of catheter movement; and at least one sensor configured to measure at least one physiological parameter of the patient. The housing can comprise a transparent material. The at least one sensor can be configured to measure at least one physiological parameter selected from the group consisting of blood pressure, heartbeat, blood oxygen level, temperature, and humidity. The at least one physiological parameter measured from the at least one sensor can be wirelessly transmitted to a patient monitoring system. The catheter housing device can include a flash storage memory unit, wherein the at least one physiological parameter measured from the at least one sensor can be stored on the flash storage memory unit. The at least one sensor can be selected from the group consisting of a temperature sensor, a blood pressure sensor, a blood oxygen saturation sensor, a liquid leakage sensor, and a skin humidity sensor. The catheter housing device can comprise at least one light. The at least one light can be LED or UV. The housing can comprise a hub component configured to at least partially contact the patient's skin when the housing is secured to the patient, and a catheter lock component configured to retain the catheter within the hub component. The housing can comprise a cover configured to enclose the insertion site and secure to at least a portion of the hub component. The catheter housing device can comprise at least one light located on a member selected from the group consisting of the hub component, the catheter lock component, and the cover. The at least one sensor can be located on a member selected from the group consisting of the hub component, the catheter lock component, and the cover. The hub component can comprise a main body secured to the catheter lock component, a membrane coupled to the main body, and an opening in the membrane positioned around the insertion site, wherein, when the housing is secured to the patient, the membrane at least partially contacts the patient's skin. The catheter housing device can comprise at least one light located on a member selected from the group consisting of the main body, the membrane, and the catheter lock component. The at least one sensor of the catheter housing device can be located on a member selected from the group consisting of the main body, the membrane, and the catheter lock component.

A method of securing a catheter to a patient near an insertion site and measuring a physiological parameter of the patient can comprise: placing a catheter housing device around the insertion site on the patient, the catheter housing device configured to surround and stabilize a catheter in order to reduce the likelihood of catheter movement, the catheter housing device including at least one sensor; attaching the catheter housing device to the patient; securing the catheter with the catheter housing device; and measuring at least one physiological parameter of the patient with the at least one sensor. The measuring of the at least one physiological parameter can comprise measuring a physiological parameter selected from the group consisting of blood pressure, heartbeat, blood oxygen level, temperature, and humidity. The method can comprise wirelessly transmitting the measured at least one physiological parameter to a patient monitoring system. The method can comprise storing the measured at least one physiological parameter on a flash storage memory unit located on the catheter housing device. The method can comprise storing the measured at least one physiological parameter on a flash storage memory unit located on the catheter housing device, and wirelessly transmitting the measured at least one physiological parameter to a patient monitoring system. The method can comprise illuminating a region proximate to the catheter housing device and/or the insertion site with at least one light source. The at least one light source can be LED or UV. The catheter housing device of the method can include a hub component and a catheter lock component, wherein the attaching the catheter housing device to the patient can comprise securing the hub component to the patient, and wherein the securing the catheter with the catheter housing device can include securing the catheter by the catheter lock component. The catheter housing device of the method can include a cover, and the method can include enclosing the insertion site by securing the cover to the hub component and/or the catheter lock component. The method can include illuminating a region proximate to the catheter housing device with at least one light source. The at least one light source can be located on a member selected from the group consisting of the hub component, the catheter lock component, and the cover.

While certain aspects, advantages and novel features of embodiments of the invention are described herein, it is to be understood that not necessarily all such advantages can be achieved in accordance with any particular embodiment of the invention disclosed herein. Thus, the invention disclosed herein can be embodied or carried out in a manner that achieves or selects one advantage or group of advantages as taught herein without necessarily achieving other advantages as can be taught or suggested herein.

BRIEF DESCRIPTION OF THE DRAWINGS

Embodiments disclosed herein are described below with reference to the drawings. Throughout the drawings, reference numbers are re-used to indicate correspondence between referenced elements. The drawings are provided to illustrate embodiments of the inventions described herein and not to limit the scope thereof.

FIG. 14A illustrates a perspective view of a catheter lock component of an alternative design of a catheter housing device.

FIG. 14B illustrates a top perspective view of a catheter lock component of an alternative design of a catheter housing device.

FIG. 14G illustrates a perspective view of an underside of a catheter lock component of an alternative design of a catheter housing device wherein a catheter is secured to the catheter lock component.

FIG. 14H illustrates a perspective view of an underside of a catheter lock component of an alternative design of a catheter housing device wherein a catheter is secured to the catheter lock component.

FIG. 14I illustrates a perspective view of an underside of a catheter lock component of an alternative design of a catheter housing device wherein a catheter is secured to the catheter lock component.

FIG. 15A illustrates a perspective view of a hub component of an alternative design of a catheter housing device.

FIG. 15B illustrates a top perspective view of a hub component of an alternative design of a catheter housing device.

DETAILED DESCRIPTION

Although certain embodiments and examples are disclosed herein, inventive subject matter extends beyond the examples in the specifically disclosed embodiments to other alternative embodiments and/or uses, and to modifications and equivalents thereof. Thus, the scope of the disclosure is not limited by any of the particular embodiments described herein. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures, systems, and/or devices described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

Hub Assembly

Figure 1A:
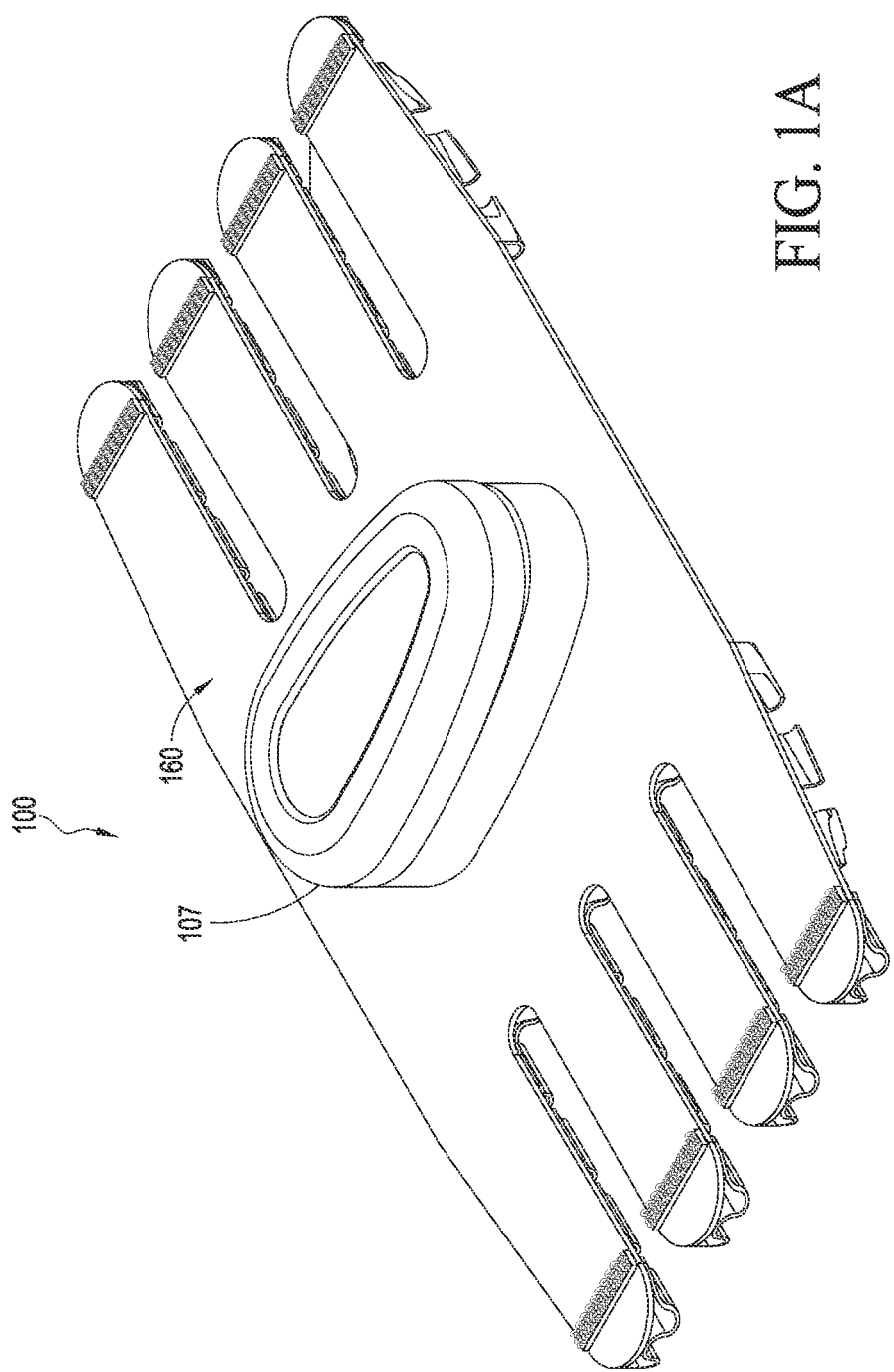
FIG. 1A illustrates a perspective view of an assembly of a catheter housing device.

As illustrated in FIG. 1A, an assembled catheter housing device 100, also referred to herein as "catheter housing" 100, can include a catheter holding structure 107 and a band 160. The catheter holding structure 107 forms a catheter lock that is configured to engage and/or secure a catheter to the patient at a location near, but not directly at, the catheter insertion site. The catheter housing device 100 can be positioned at and/near any location where an IV can be inserted into a patient.

Figure 1B:
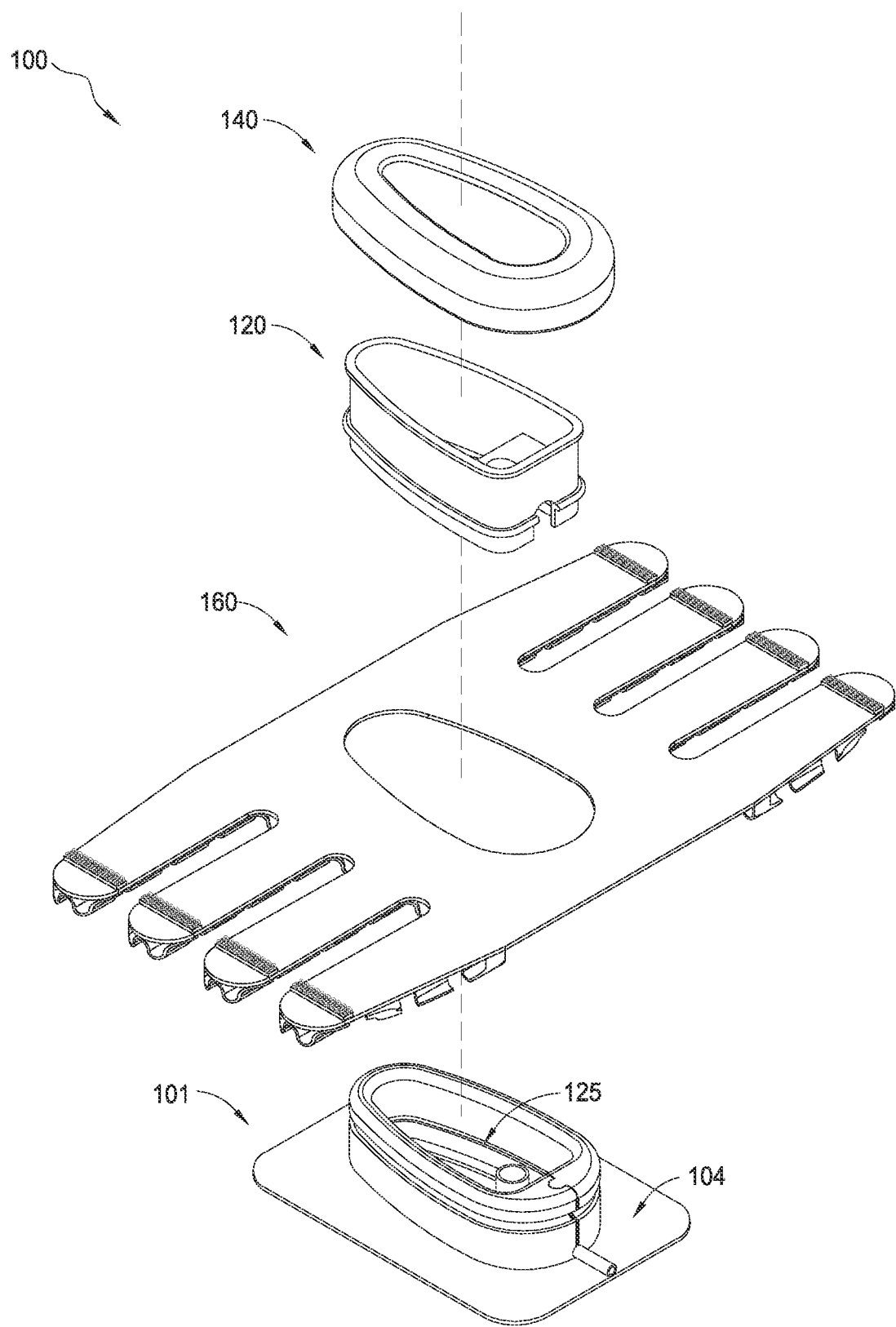
FIG. 1B illustrates an exploded view of a catheter housing device.

FIG. 1B illustrates an exploded view of the catheter housing device 100. Catheter capsule structure 107 of catheter housing device 100 can include a hub 101, a lock body 120 and a cover 140. In some alternative designs, the band 160 can slide and/or fit around at least a portion of the hub 101. The catheter lock 120 can be inserted into an opening in the hub 101 to lock a catheter in place. The cover 140 can be coupled to the hub 101 and/or the catheter lock 120 to secure and/or seal the stabilizing device.

When fully assembled, the catheter capsule structure 107 can be sealed and supplied with inert gas that is free from oxygen to inhibit microbe development. The closed interior compartment of the main body 102 above the insertion site can be supplied with sterilized inert gas and/or a soothing anesthetic vapor drug. For example, the inert gas can suffocate microbes or other contaminants around the needle insertion site. The inert gas can be pumped from a special small metallic ampule attached to the band 160. Alternatively, a needle insertion port can be provided on the cover in order to allow a needle to penetrate through the port and supply the gas. The port can have a self-sealing valve to prevent gas from escaping once the needle is removed. Thus, the interior compartment formed by the main body 102 and cover 140 can advantageously allow for the insertion site to be sterilized before and/or after a catheter is inserted and/or removed.

Figure 2A:
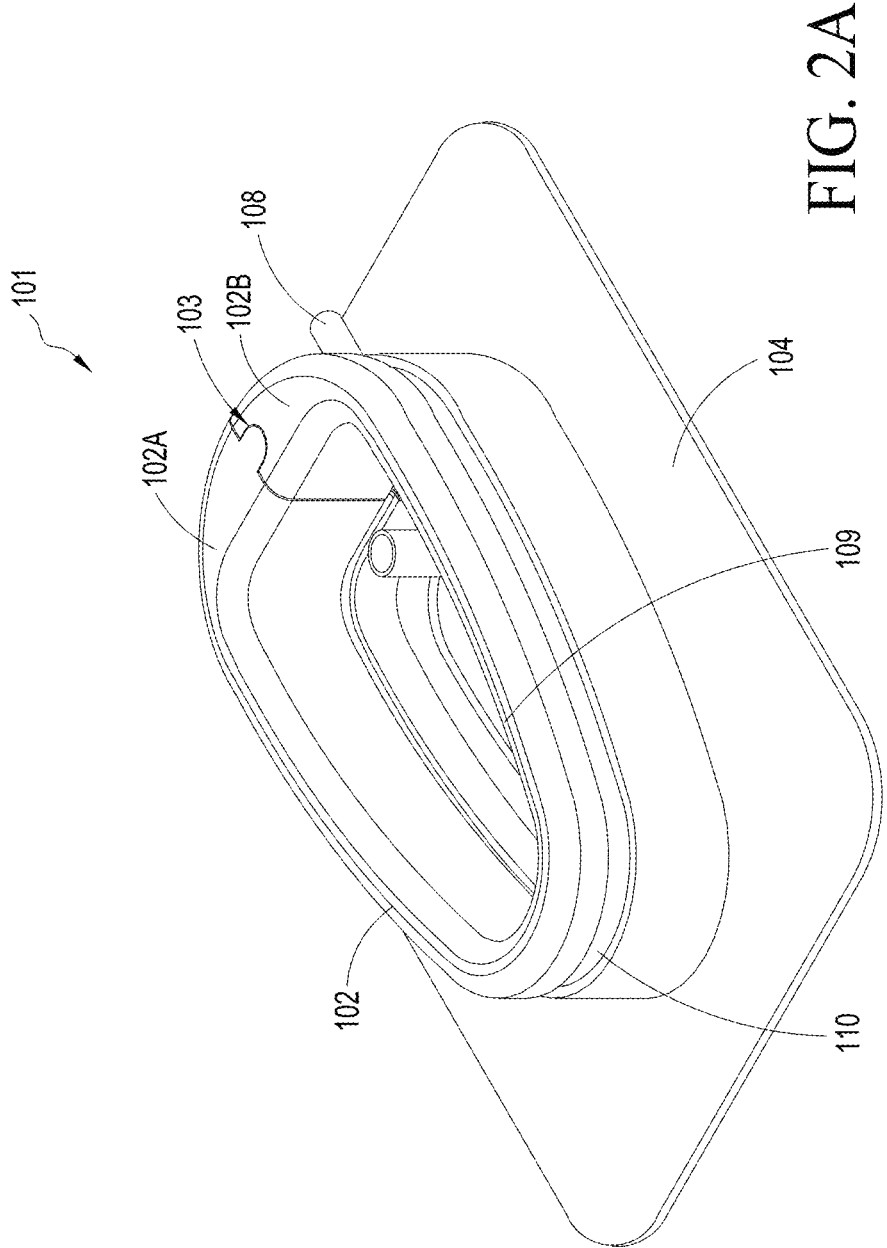
FIG. 2A illustrates a perspective view of a hub of a catheter housing device.

As shown in FIG. 2A, the hub 101 can include a main body 102 and a flange or membrane 104. As used herein, a membrane can comprise a thin, flat, flexible, planar and/or elongate portion of the device. The main body 102 of the hub 101 can be generally egg-shaped. However, the main body 102 can be approximately trapezoidal, rectangular, square, oval and/or circular in shape, among other shapes that can encapsulate the insertion site. The main body 102 can comprise plastic, rubber, and/or silicone, among other materials. Additionally, the main body can comprise a combination of materials. The hub 101 can be manufactured of a soft, pliable material, such as medical grade silicone, that is soft on skin and generally conforms to the shape of the placement site. Alternatively, harder silicone, or rubber can be used.

Figure 2B:
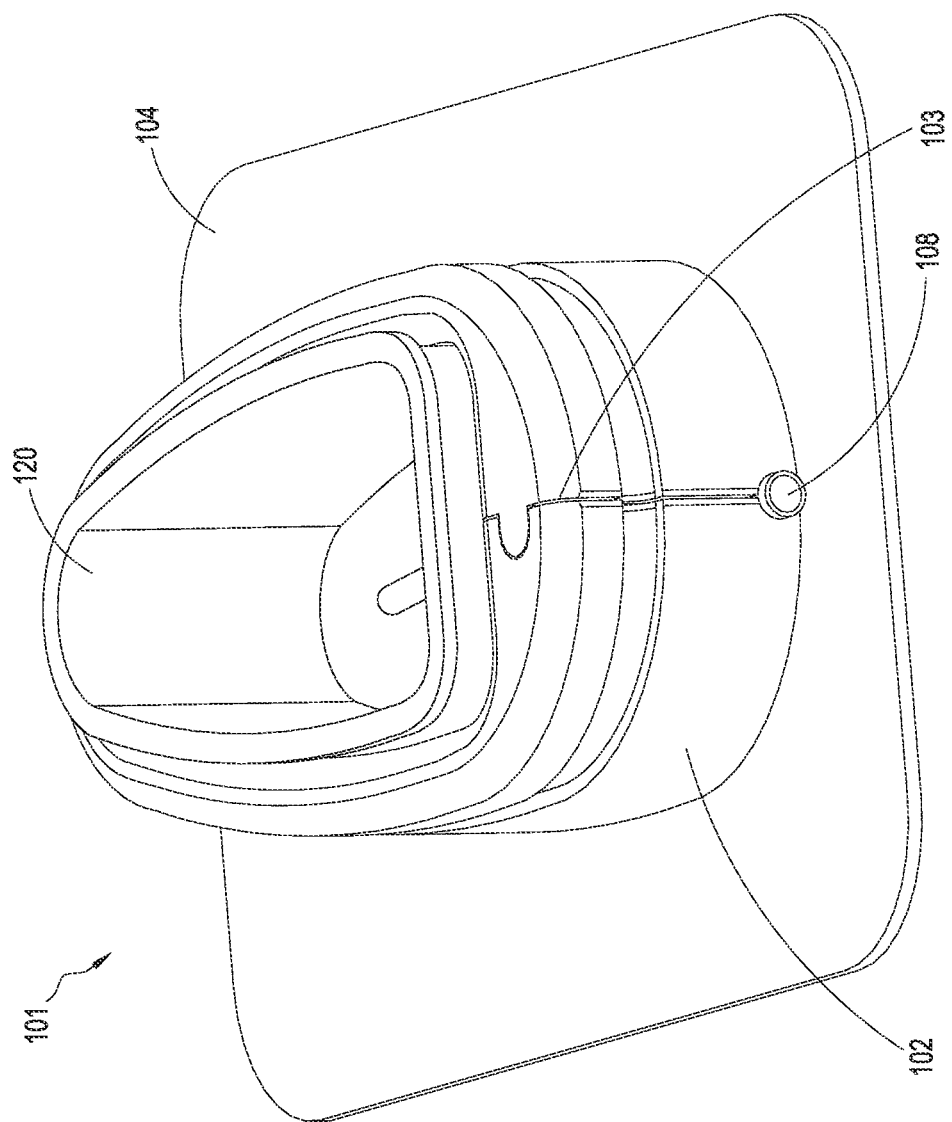
FIG. 2B illustrates a rear view of a hub of a catheter housing device.
Figure 2C:
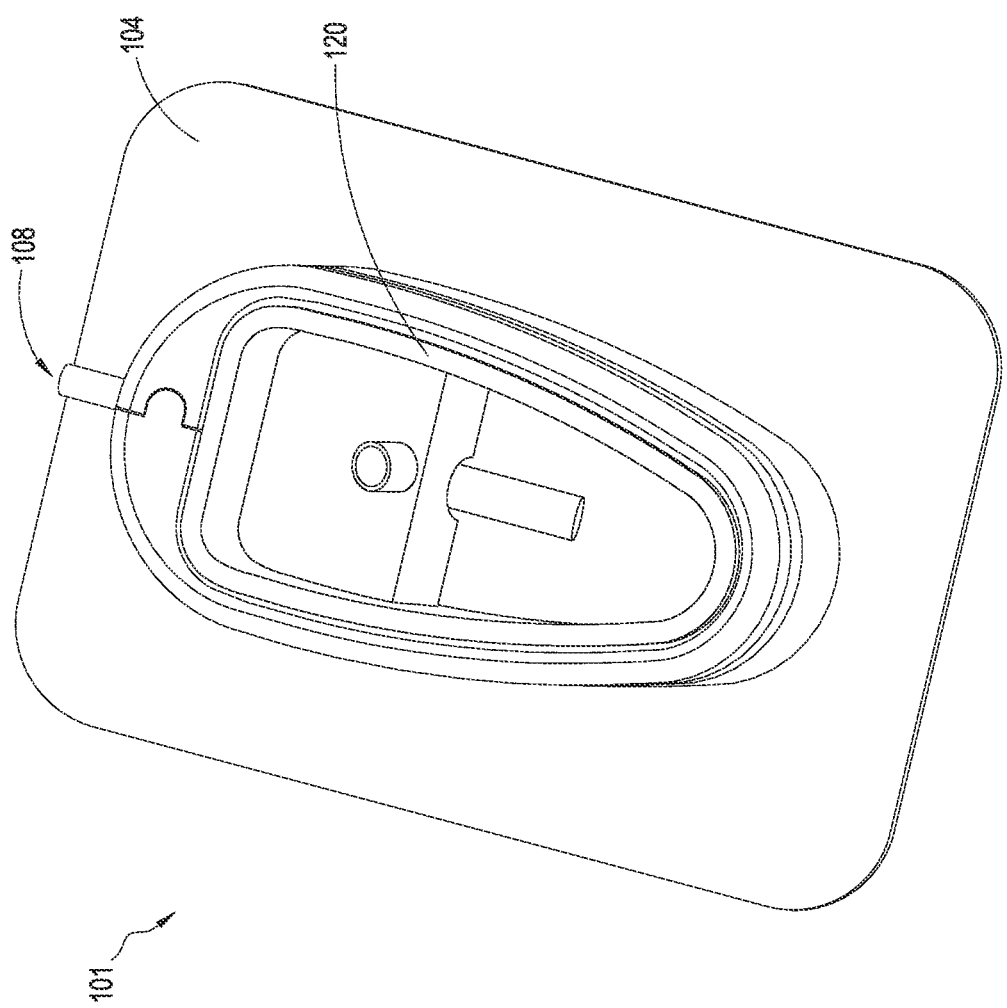
FIG. 2C illustrates a top perspective view of a hub of a catheter housing device.

As illustrated in FIGS. 2A-2C, the main body 102 can include a tubing port and/or tubing port separation 103. The tubing port separation 103 can separate by flexing the main body 102 to allow a path to a tubing port. The tubing port and tubing port separation 103 allows catheter tubing to pass through the main body's 102 side walls and into the catheter insertion area. The port and/or port separation 103 can seal around the tubing once inserted. The main body 102 can be formed so as to not extend continuously around a perimeter of hub 101. Instead, in some alternative designs, a first side 102A and a second side 102B of the main body 102 can be spaced apart, pulled apart, pushed apart, and/or otherwise separated. In some alternative designs, the first side 102A and the second side 102B can be biased towards one another. For example, the portion of the first side 102A and the second side 102B adjacent the tubing port separation 103 can tend to be pushed together, pulled together, and/or otherwise forced together after being separated. Accordingly, the two sides 102A, 102B of the main body 102 of the hub 101 can be pulled apart to allow passage of some portion of the catheter there between, after which the two sides 102A, 102B are pushed together to seal the main body 102 about the catheter tubing. For example, as the catheter passes through the bottom of the main body 102 at the tubing port separation 103, the main body 102 can be divided in half between the first side 102A and the second side 102B. Alternatively, the main body 102 can be formed without a tubing port separation 103, in which tubing is simply threaded through a tubing port.

The main body 102 can include a top wall 109. The top wall 109 can be convex. The top wall 109 can be smooth and/or rounded. The top wall 109 of the main body 102 can advantageously allow the cover 140 to engage with the main body 102. For example, the top wall 109 of the main body 102 can allow the cover 140 to slide over and securely fit around the main body 102. The top wall 109 of the main body 102 can be flat and/or concave.

As shown in FIG. 2A, the main body 102 can include an outer groove 110. The outer groove 110 can extend circumferentially about all or a portion of the main body 102. In some alternative designs, the outer groove 110 is positioned approximately at a center (for example, one-half the height) of the main body 102. The outer groove 110 can be positioned above or below the center of the height of the main body 102. For example, the outer groove 110 can be spaced from the top wall 109 and the base of the main body 102. The outer groove 110 can be advantageously shaped to receive a corresponding tongue 146 of the cover 140 (see FIG. 5) and/or a corresponding inner rib of the cover 140. The outer groove 110 can allow the cover 140 to engage with the main body 102. For example, the outer groove 110 can allow the cover 140 to engage the main body 102 by a snap-fit, press fit, and/or other configurations for securely connecting the cover 140 to the main body 102.

As discussed above, the hub 101 can include a membrane 104. The membrane 104 is generally rectangular in shape. However, in some alternative designs, the membrane 104 is egg-shaped, trapezoidal, square, oval, and/or circular in shape, among other shapes.

The main body 102 can be integrally formed with the membrane 104. For example, the main body 102 can be molded or co-molded with the membrane 104. The main body 102 can also be pressed onto, adhered to, and/or otherwise attached to a top surface of the membrane 104.

The membrane 104 can extend outwardly from a base of the main body 102. For example, the membrane 104 can be coupled with an outer edge of the base of the main body 102. A bottom surface of the base of the main body 102 can be coupled with the membrane 104. For example, at least a portion of the membrane 104 can extend inwardly towards an inner region of the main body 102 (see, for example, FIG. 4). In some alternative designs, the membrane 104 forms a thin layer to surround at least a portion of a perimeter of the main body 102. Thus, the membrane 104 can surround all or a portion of a perimeter of an inner edge and/or an outer edge of the base of the main body 102.

Figure 4:
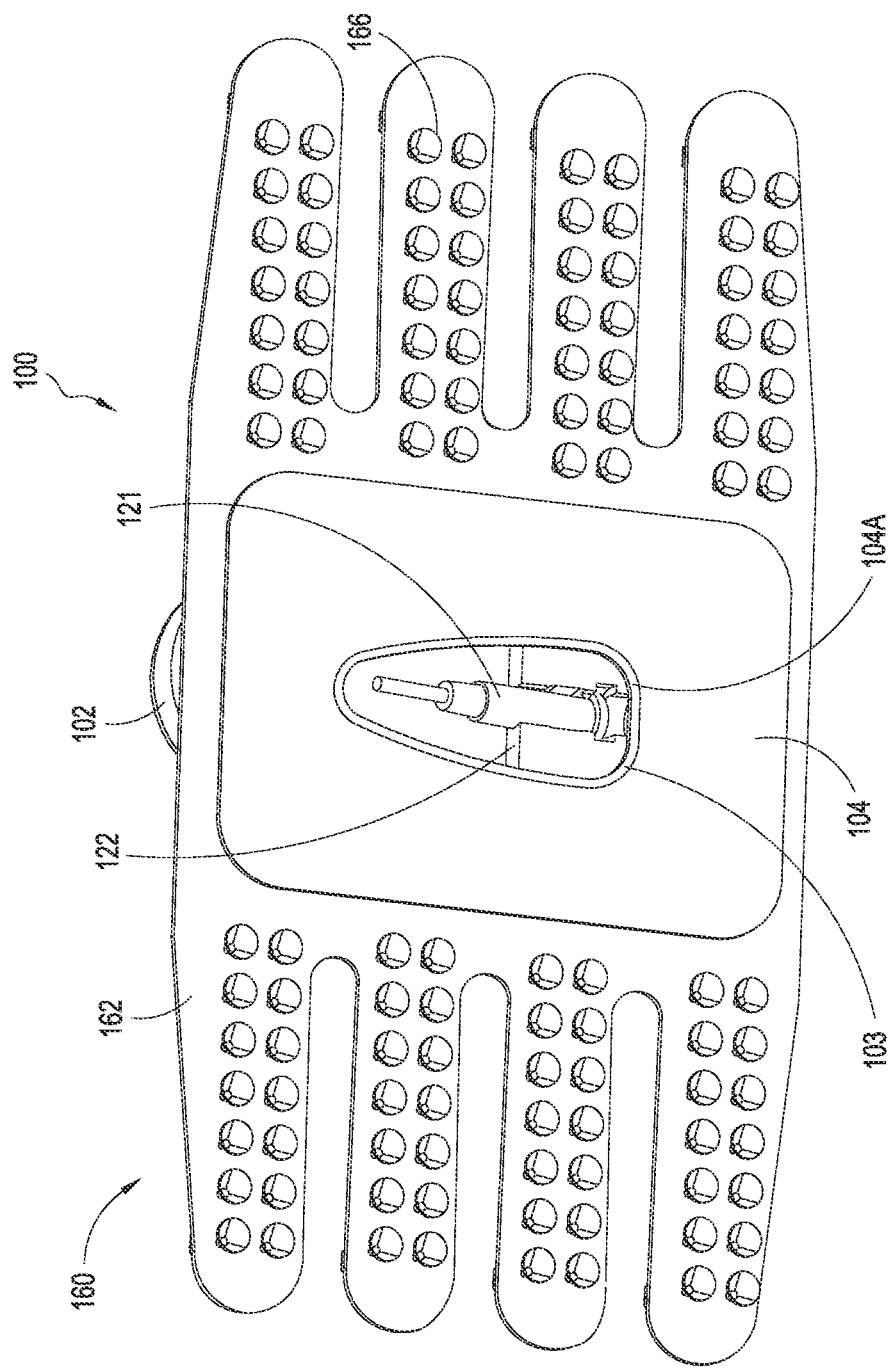
FIG. 4 illustrates a bottom perspective view of an alternative design of a catheter housing device where the band assembly comprises suction cups.

The membrane 104 can form an outer membrane that extends outwardly from and surrounds a perimeter of the base of the main body 102. The hub 101 can include an inner membrane 104A that is formed integrally with and/or is separate from the membrane 104. For example, in some configurations, as shown in FIG. 4, the inner membrane 104A (for example, a skirt, an overhang, a flange, a sealing structure, a ridge, or other structure) can be formed at the bottom of the opening in the hub 101 at the base of an inner region of the main body 102. The inner membrane 104A can be formed between outer portions of the membrane and the base of the inner region of the main body 102. The inner membrane 104A can extend toward the patient.

The inner membrane 104A can at least partially surround the insertion site. Such configurations can advantageously reduce and/or eliminate ingress of pathogens to the insertion site. For example, the inner membrane 104A can include a thin silicone membrane. The inner membrane 104A can overlap and/or surround the needle and/or the insertion site. This can advantageously help to ensure that the hub 101 is secured and/or sealed to the patient's skin. For example, the inner membrane 104A can overlap at least a portion of the insertion site and/or needle to provide a hermetic sealing isolation state between the hub 101 and the patient's skin. Accordingly, the inner membrane 104A can help to inhibit or prevent air and/or gases from an outside environment from entering the insertion site.

Such configurations of an inwardly extending membrane 104A can also inhibit or prevent lower edges of needle lock from contacting the skin underneath the needle lock, as described in more detail below. This can help to inhibit or prevent skin abrasions, ulcers, and/or irritation caused by contact between the needle lock and the patient's skin.

The membrane 104 and/or main body 102 can include a tube port 108. The tube port 108 forms a hole or slot in the main body 102. The port can be positioned near a lower portion of the main body 102. The port 108 can be positioned above, for example, directly above, the membrane 104 to allow the catheter tube to pass through. Such configurations can be configured to receive, snap onto, and/or engage at least a portion of the catheter. Such configurations can secure the catheter in place away from the insertion site.

The main body 102 and the membrane 104 can comprise the same material. The main body 102 and the membrane 104 can include different materials. For example, the membrane 104 can comprise silicone, plastic, and/or rubber, among other materials.

The membrane 104 can also incorporate various sensors to measure physiological parameters or condition of the patient. For example, the sensors can include a temperature sensor to measure a temperature of the measurement site of a patient. The sensors can also include a pulse rate sensor, a blood oximeter sensor, phlebomanometer or artery blood manometer sensor, puncture site hygrometer, blood glucose sensor or any other noninvasive physiological vital signs sensors.

Catheter Lock

Figure 3A:
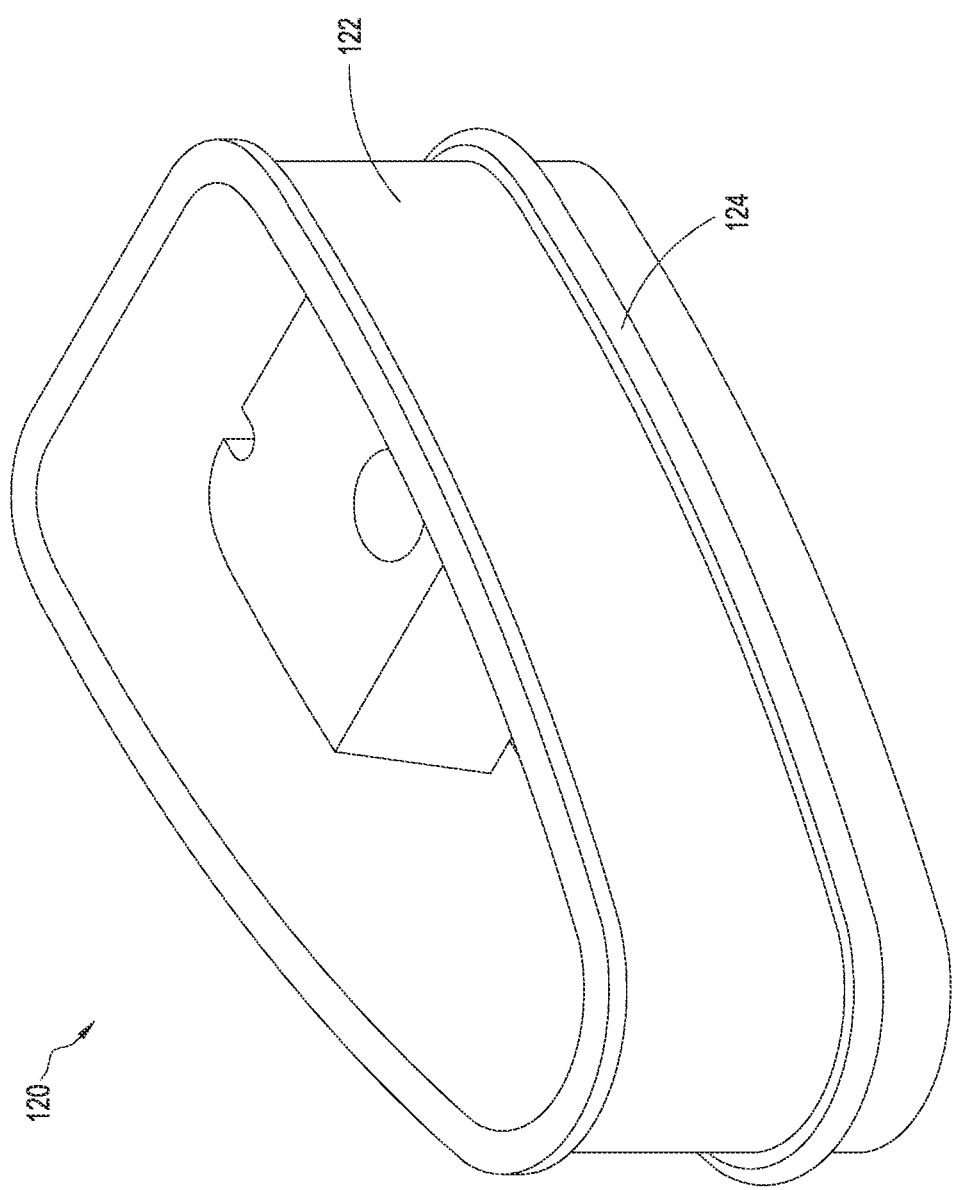
FIG. 3A illustrates a perspective view of a lock body of an alternative design of a catheter housing device.
Figure 3B:
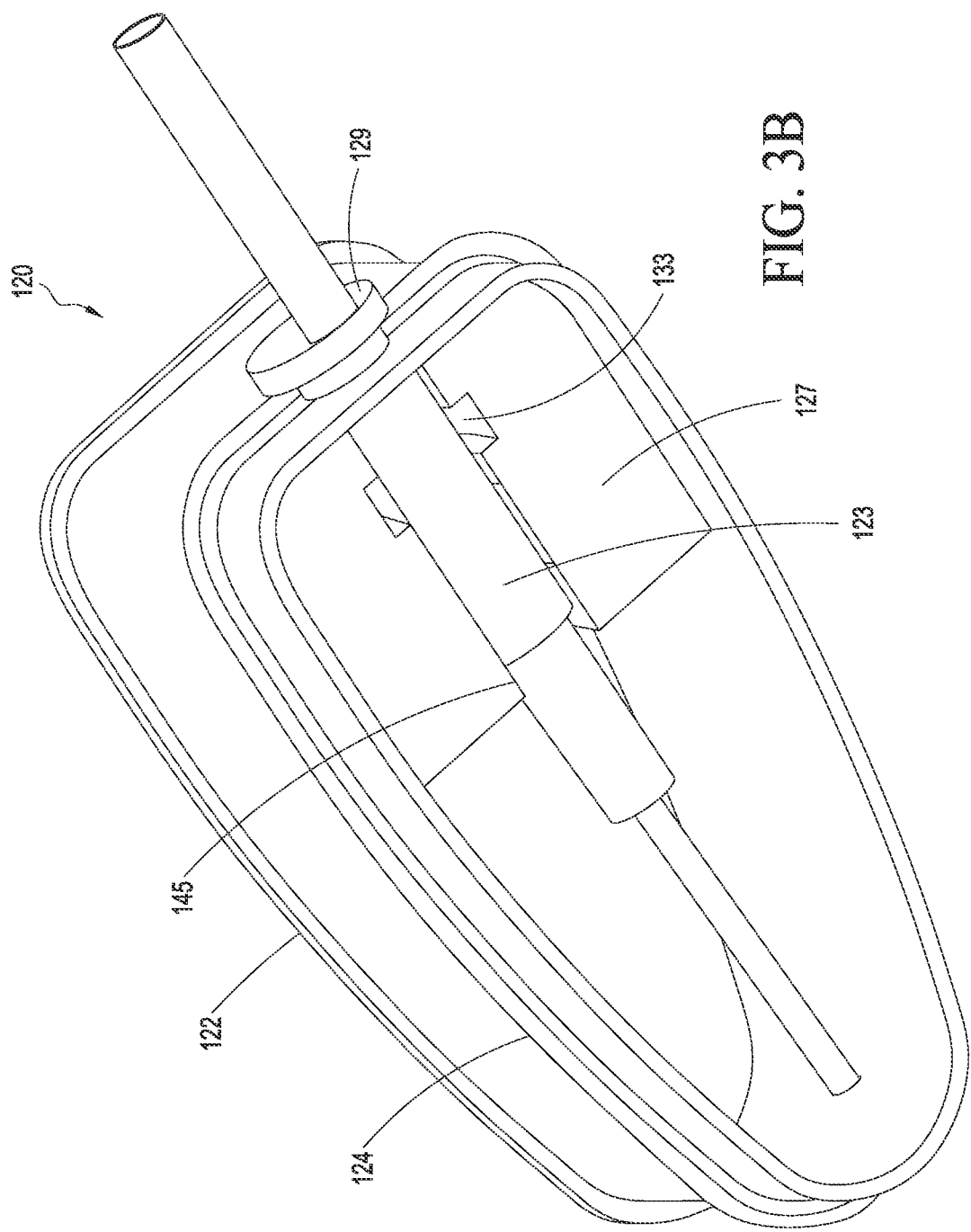
FIG. 3B illustrates a bottom perspective view of a lock body of a catheter housing device.
Figure 3C:
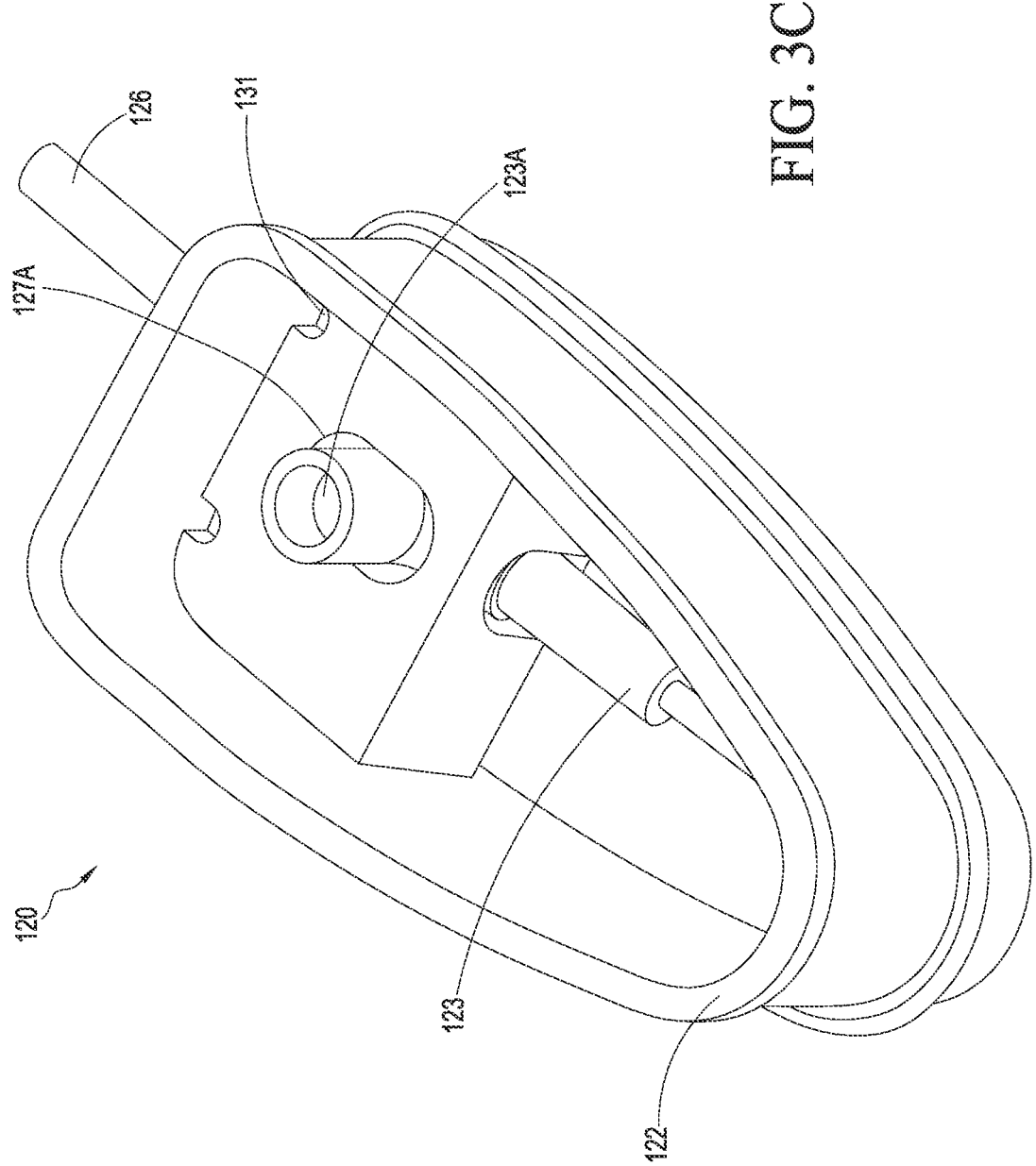
FIG. 3C illustrates a top perspective view of a lock body of a catheter housing device.
Figure 3D:
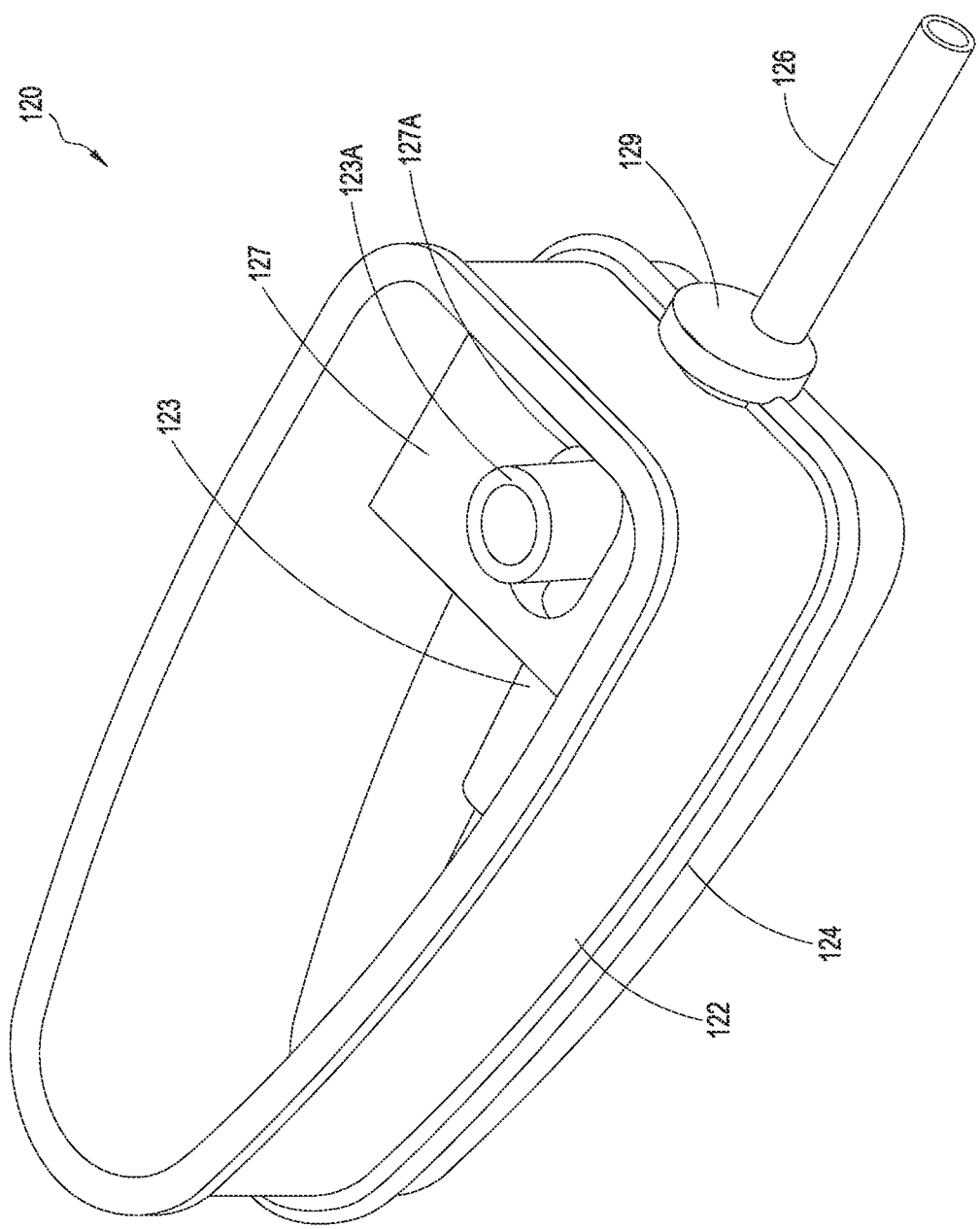
FIG. 3D illustrates another top perspective view of a lock body of a catheter housing device.

FIG. 3A illustrates an alternative design for a catheter lock 120. The catheter lock 120 can include a lock body 122. The lock body 122 can comprise rigid plastic material, such as a hard plastic, and/or hard rubber, among other hard materials. The lock body 122 can be made of a clear or substantially transparent material to allow visibility of the insertion site, for example, through the lock body 122. Transparency can also allow an incorporated LED or UV light to spread light over the insertion site. The lock body 122 or portions of the lock body can also be opaque or partially opaque.

The lock body 122 can include a tongue and/or a groove 124. In FIG. 3A, for example, the lock body 122 includes a tongue 124 to engage a corresponding locking groove 125 (FIG. 1B) positioned along at least a portion of an inner perimeter of an inner wall of the hub 101. This can allow the lock body 122 to securely engage with the main body 102. The lock body 122 can engage with the hub 101 through a snap-fit configuration, press fit configuration, and/or other securement structures or methods. Such configurations can advantageously allow the lock body 122 to securely engage with the main body 102, yet quickly be removed from and/or be attached to the main body 102 when the catheter is removed, replaced, inserted, and/or accessed.

The lock body 122 can enclose the catheter and secure the catheter in place. For example, once inserted through the opening in the main body 102 and the lock body 122 is securely engaged with the main body 102, the lock body 122 can be fixed in a proper position. The engagement between the lock body 122 and the main body 102 can advantageously inhibit and/or prevent movement of the lock body 122 relative to the main body 102. The lock body 122 can inhibit or prevent the catheter from moving once the lock body 122 is secured with the main body 102.

The catheter lock 120 can be configured to secure a hub 123 of the catheter (or other portion of a catheter) in the proper orientation relative to the patient's skin. The securement of the hub 123 of the catheter or other portion of the catheter by the catheter lock 120 can be a physical locking, holding, stabilizing without locking, retaining, stabilizing to prevent movement, stabilizing to minimize or reduce the likelihood of movement, or another type of securement. For example, the lock body 122 can have a recess sized and shaped to hold a portion of the catheter hub in a friction fit configuration, a snap-fit configuration, a press fit configuration, and/or another securement configuration method or structure. Additionally, the securement recess of the catheter lock 120 can comprise a hook. The catheter lock 120 can stabilize the catheter relative to the insertion site while still allowing the catheter to move slightly in order to accommodate patient movement as described further below.

The lock body 122 can fit within the interior region of the main body 102 to form a hermetic sealing structure around the catheter. Thus, the lock body 122 (e.g., in combination with the cover 140) can form a seal around the catheter and/or catheter hub 123. The catheter hub 123 can include a ring 129 or flange. The ring 129 can help to seal and/or lock the catheter in place within the hub lock body 122. For example, the ring 129 can surround the catheter and engage an outer wall of the lock body 122 to securely seal the catheter in place. The ring/flange 129 can be configured to engage with a groove 133 of the bridge structure 127.

The lock body 122 creates an interior compartment above the sealed insertion site once the lock body 122 is positioned within the opening of the main body 102 and/or securely engaged to the main body 102. For example, the lock body 122 can include a raised support bridge or structure 127 to enclose at least a portion of the catheter or catheter hub. The raised support structure 127 extends from an inner side wall of the lock body 122 to an opposite inner side wall of the lock body 122. The raised support structure can be positioned near the insertion site along one end of the lock body 122. The raised support structure 127 can include an aperture 133 to engage the catheter and/or catheter hub 123. The support structure 127 can include a cavity 145 sized and shaped to receive all or a portion of the catheter hub 123. This allows the catheter to pass through the aperture. Some configurations can allow a seal to be formed around the catheter opening and enclose the insertion site.

The raised support structure (bridge) 127 can include a swinging mechanism. The swinging mechanism can allow the structure 127 to rotate and/or tilt. For example, the swinging mechanism can comprise a hinge (e.g., mechanical and/or living hinge) between the raised support structure 127 and the walls of the lock body 122. The swinging mechanism can allow the structure 127 to tilt upwardly and/or downwardly (e.g., about an axis perpendicular to the catheter hub 123. The swinging mechanism can allow the structure 127 to tilt according to the inclination of the needle and/or catheter. For example, the swinging mechanism can allow the structure 127 to tilt as the patient moves, to accommodate movement of the needle and/or catheter. The tilt of the structure 127 can be limited in its rotation to prevent the catheter from swinging too far relative to the body. The structure 127 can also be configured to keep the catheter fixed in its natural position to the patient's skin after insertion. This provides for an optimal catheter holding angle. This can help to limit or prevent irritation caused by contacting of needle's cannula tip with vein lumen sides. For example, the holding angle can be between 1 and 45 degrees. The inclination angle can also be between 1 and 10 degrees, between 10 and 20 degrees, or between 20 and 30 degrees. The holding angle can be more than 45 degrees as well, depending on the implementation of the stabilization device. The holding angle can also be at a very small angle, such as between 0 and 1 degrees. Such configurations can help to limit forces provided to the insertion point. The raised support structure 127 can be made of hard plastic, such as anti-erosion hard plastic, among other hard materials.

Some catheter hubs can include a catheter opening 123A. The raised sealing structure 127 can include an aperture 127A. The aperture 127A can allow the catheter opening 123A to pass through the raised support structure 127. The aperture 127A can be cylindrical, circular, square, or rectangular, among other shapes or combination of shapes. The catheter opening 123A can provide an access point through which a care provider or other person can administer fluids (for example, medicinal, nutritive, and/or hydrating fluids) to the patient instead of or in addition to the fluids provided though the attached catheter 126.

The catheter lock 120 includes at least one light source 131. For example, the catheter lock 120 can include one, two, three, four, five, six, seven, eight, or nine or more light sources 131. Preferably, the catheter lock 120 can include at least two light sources 131. The light sources can include LEDs. The light sources can allow the catheter to be inspected during the day and/or night. The light sources can also indicate that lock structure 122 is properly fit into the main body 102. The light sources can also indicate that the catheter is not properly positioned and/or secured to the patient. For example, the lights can change colors, flash at certain speeds, and/or change brightness to indicate an issue with the catheter lock 120 or catheter. The light source can include a UV light source to help with disinfecting the catheter and/or hub and/or insertion site.

One or more of the light sources can also be used to illuminate various structures. For example, a first light can illuminate an area surrounding and/or proximate to the catheter. For example, the one or more light sources can illuminate a region within 3 feet from the catheter housing device 100. Alternatively, the one or more light sources can illuminate a region within 1 feet from the catheter housing device 100. Alternatively, the one or more light sources can illuminate a region within 5 feet from the catheter housing device 100. The raised sealing structure 127 can distribute light within the hub 101. One light can be used to illuminate the lock structure while a second light can provide an alarm and/or indicator to indicate that a complication is occurring (for example, the catheter or catheter lock is not properly positioned). The light sources can also provide a patient with an indication of wellness and/or that the patient is in a well-state. For example, when the light sources are not emitting light, this can indicate that a patient is in a well state of being.

Cover

Figure 5:
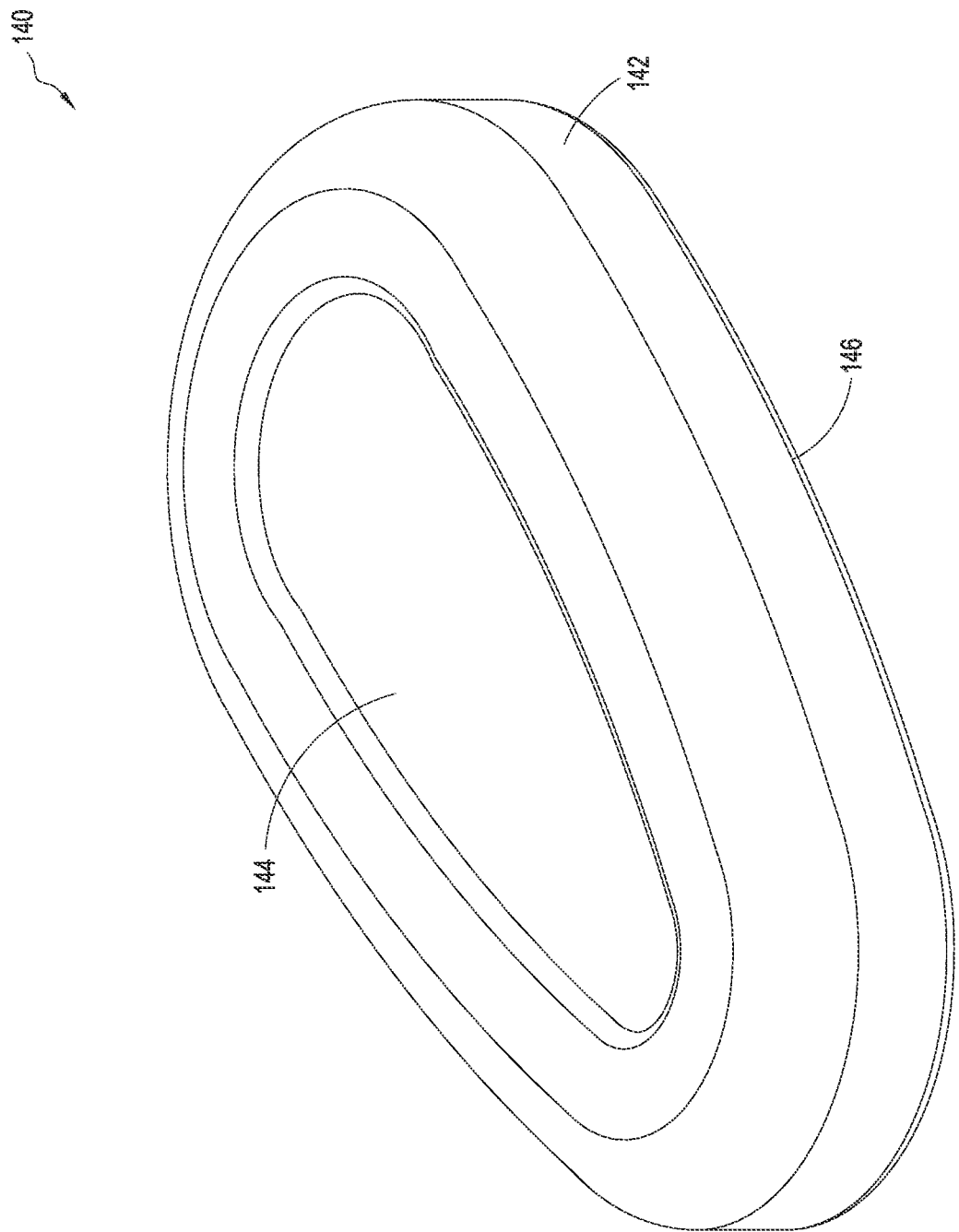
FIG. 5 illustrates a perspective view of a cover of a catheter housing device.

FIG. 5 illustrates an embodiment of the cover 140. The cover 140 can include a cover body 142, a cover window 144, and a cover tongue 146. As shown in at least FIGS. 1A-1B, the cover 140 is configured to enclose the main body 102 and catheter lock 120 within the interior of the hub 101.

The cover body 142 can couple with a top surface of the main body 102 of the hub 101. For example, the cover tongue 146 can be positioned inwardly offset from an outer edge of the cover body 142. The cover tongue 146 can slide over or into an interior or exterior region of the main body 102 of the hub 101. The cover tongue 146 can snap into an interior or exterior region of the main body 102. For example, the cover tongue 146 can contact an outer side wall of the main body 102. The cover tongue 146, or some other portion of the cover 140, engages the outer groove 110 of the main body 102. The cover tongue 146 can contact an inner side wall of the lock body 122 to engage the cover 140 with the hub 101. The cover tongue 146 can slide into and/or snaps into a space formed between an outer wall of the lock body 122 of the catheter lock 120 and an outer wall of the main body 102. Thus, the cover tongue 146 can engage the main body 102 to secure the cover 140 in place and to enclose the external components of the hub 101.

A seal can be formed such that the cover 140 does not allow external air and/or contaminants from entering the enclosed internal volume of the hub 101. For example, the cover 140 can engage the lock body 122 and/or the main body 102 to form a closed and/or isolated atmosphere, which encloses the insertion site. In such configurations, the insertion site can advantageously be sterilized. Similarly, the cover 140 can advantageously help to inhibit or prevent microbe contaminate and help to lower contamination vulnerability. The cover 140 can also be configured to prevent the separation 103 from separating while in use.

As discussed above, the cover 140 can include a cover window 144. As shown in FIG. 5, the cover window 144 can be formed along a top surface of the cover body 142. The cover window 144 can be recessed along the top surface of the cover body 142 such that it extends inwardly towards an interior region of the main body 102 when assembled. The cover window 144 can be substantially clear to allow a doctor and/or a patient to inspect the insertion site and/or catheter. For example, such configurations can advantageously allow a doctor and/or a patient to view the insertion site and/or the catheter position without the need to disassemble the stabilizing device 100. Thus, the cover window 144 can allow the stabilizing device 100 to remain sealed.

Band

Figure 6:
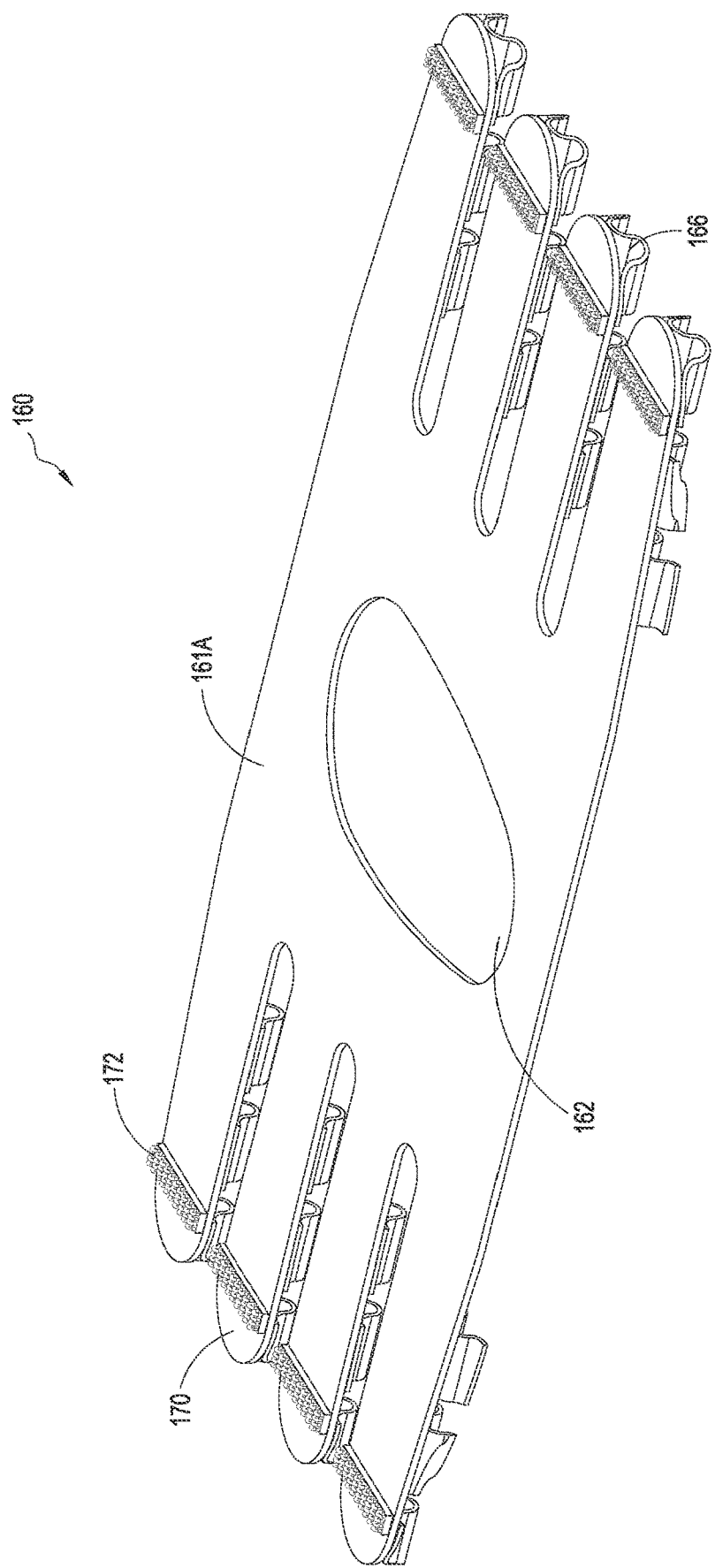
FIG. 6 illustrates a top perspective view of a band base membrane of a catheter housing device.

FIG. 6 illustrates an embodiment of the band 160. The band 160 can include an opening 162 to receive the hub 101. The band 160 can fit over the hub 101 such that the main body 102 extends through the opening 162 of the band 160 and the membrane 104 of the hub 101 is captured below the band 160. The opening 162 can stretch such that the band 160 tightly fits around an outer wall of the main body 102 of the hub 101. Alternatively, the band 160 and main body 102 can be formed together as a single structure.

The band 160 includes an upper surface 161A and a lower surface 161B. The upper surface 161A is configured to face away from the patient's skin in use (see, e.g., FIG. 6) and the lower surface 161B is configured to face towards the patient's skin in use (see, e.g., FIG. 7). At least a portion of the upper surface 161A can include connection structures 172. In one alternative design, the upper surface is entirely covered with connection structures 172.

The band 160 can include one or more attachment arms 170. For example, the band 160 can include one, two, three, four, five, six, seven, eight, nine, ten, eleven or more attachment arms 170. The attachment arms 170 can wrap around a patient's body part including an arm, wrist, leg, hand, and/or neck, among other body parts. The attachment arms can include one or more connection structures 172 such as hook and loop fasteners, clips, hooks, or other known attachment systems. One or more strips (not shown) of a corresponding fastener can be used to attach the one or more arms 170 on one side of band 160 to one or more arms 170 on the other side of the band 170 in order to hold the band 160 in place on a patient. For example, one, two, three, four, five, six, seven, eight, nine, ten, eleven or more strips of a corresponding fastener can be used to attach the one or more arms 170 on one side of band 160 to one or more arms 170 on the other side of the band 170 in order to hold the band 160 in place on a patient. The band 160 can include eight arms. For example, one-half of the arms 170 can be positioned on one side of the opening 162 and one-half of the arms 170 can be positioned on the opposite side of the opening 162. The band 160 can include at least one, two, three, four, five, six, seven, eight, nine, and/or ten or more arms positioned on opposite sides of the opening 162. The arms 170 positioned on opposite sides of the opening 162 can be positioned in an alternating or misaligned configuration. In some such configurations, one side of the opening 162 can include an even number of arms 170 and the other side can include an odd number of arms 170. Such configurations can distribute the band about the entire body part of the patient to increase the strength of the securement of the band 160 to the patient. In some configurations, at least one arm 170 can be configured to wrap around a patient's body part and attach to a corresponding arm, while other arms are left open without a connection. By alternating which arms 170 are used to hold the band 160 onto the patient's tissue, the patient's skin can be provided relief by decreasing pressure and contact between connection structures and the patient's skin.

Alternatively the band 160 can include a single attachment arm 170. The band 160 can be a single arm that is configured to wrap around a patient's body part.

The connection structures 172 can include a plurality of hook and loop structures, buckles, fungi-like attachment, and/or other attachment structures or methods. The connection structures 172 can facilitate connection of other complimentary bands, straps, and/or other components to the band 160. For example and without limitation, the upper surface 161A can include soft hooks to provide a wide surface area for fixing various peripheral tools to the band 160, such as a catheter tube, an LCD monitor of a microprocessor, and/or a metallic ampule of the soothing and sterilizing gas.

The connection structures 172 can facilitate attachment of a first set of arms 170 positioned on one side of the band 160 to a second set of arms 170 positioned on another side of the band 160. For example, in use, the first and second set of arms 170 can be configured to wrap around a patient's arm such that the connection structures 172 of the first set of arms 170 attaches to the connection structures 172 of the second set of arms 170 to secure the catheter housing 100 to the patient.

Figure 7:
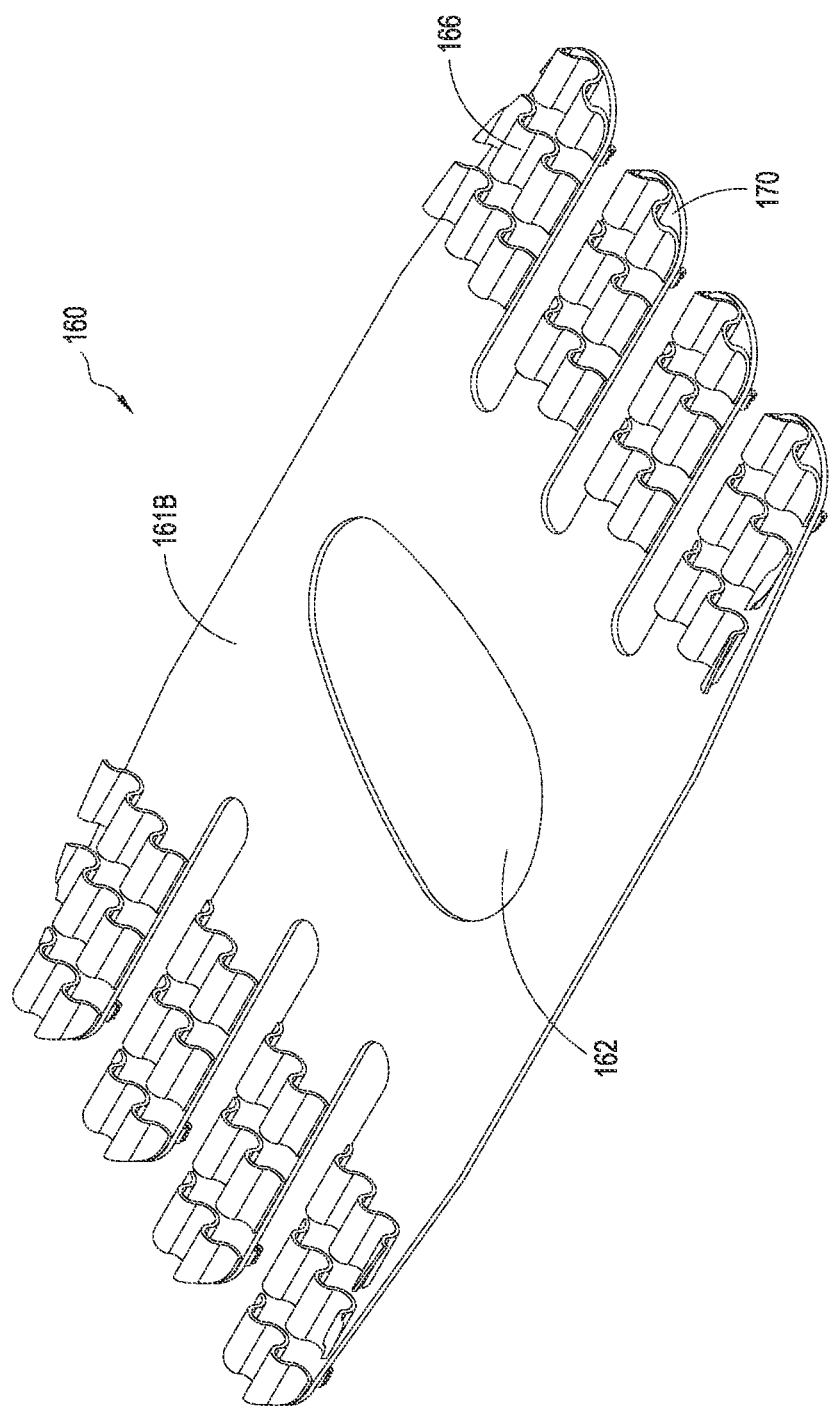
FIG. 7 illustrates a bottom perspective view of a back hand band of a catheter housing device.

FIG. 7 illustrates an embodiment of the lower surface 161B. As discussed above, the lower surface 161B is generally configured to face towards the patient's body in use and/or contact the patient's skin. For example, the lower surface 161B of the band 160 can engage the patient to secure the catheter housing 100 to the patient and/or surround the insertion site. To reduce irritation and allow the patient's skin to breath, the band 160 can include a plurality of contact structures 166. The contact structures 166 can include a plurality of corrugated strips (see FIG. 7), suction cups (see FIG. 4), silicone or hybrid silicone-silk deep velvet structure, and/or other contacting mechanisms. The contact structures 166 can include rows of corrugated strips, suction cups (as shown in FIG. 4), and/or other contacting mechanisms. The contact structures 166 can be positioned in alternating rows. For example, the contact structures 166 can include alternating rows of corrugated strips and suction cups. The band can include alternating arms of various contacting mechanisms, as described below. The contact structures 166 can be configured to space the band from the patient to allow the patient's skin to breath, yet secure the catheter housing 100 to the patient. For example, the contact structures 166 can allow the band 160 to maintain engagement with the patient's skin without the use of adhesives (including, for example, chemical adhesives, tapes, or other adhesives).

The contact structures 166 can advantageously reduce abrasion of the patient's skin. The contact structures 166 promote regular air/blood flow and ventilation along the patient's skin beneath the band 160.

As discussed above, the lower surface 161B of the band 160 can include a plurality of suction cups. The suction cups can be designed to be of a thin narrow circumference creating finely intricate suction cups which can be configured to stabilize a connection between the band 160 and the patient's skin. The band 160 can be manually pressed onto the patient's skin to secure the contacting structures 166 of the band 160 to the patient. The contact structures, such as the suction cups and/or corrugated strips, can engage with the patient's skin such that the band 160 does not necessarily wrap entirely around the patient's arm. For example, the band 160 can wrap around only a portion of the patient's arm. In such configurations, the contact structures 166 can provide sufficient engagement or suction force to securely engage the catheter housing device 100 to the patient with and/or without the use of additional connection structures, such as connection structures 172.

The lower surface 161B comprises a soft flesh-like material to increase comfort and wearability by highly reducing irritation to the patient. Such materials and/or configurations can include miniature pillows. The materials can include silicone or other appropriate FDA approved materials. The connecting structure 166 can comprise a soft material, such as silicone. For example, the lower surface 161B can be made from soft flesh-like, high strength silicone material (for example, FDA compliant) to increase the air circulation between underneath band surface and the patient's skin. The contacting structures 166 can advantageously help to minimize the surface area of the band 160 that contacts the patient's skin to reduce irritation. This can allow the catheter housing 100 to be secured to the patient for longer periods of time without having to be removed unnecessarily. Similarly, such configurations can reduce the risk of complications that can arise from applying the band 160 to the patient's skin.

Figure 8:
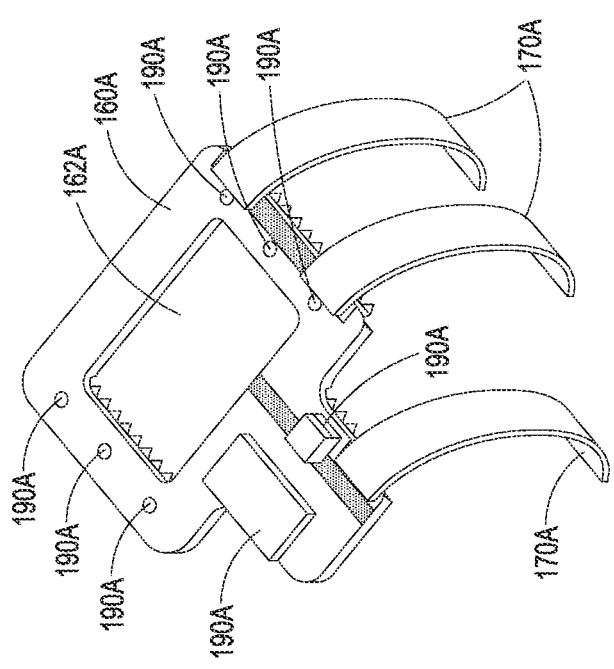
FIG. 8 illustrates a perspective view of a band of a catheter housing device comprising a plurality of sensors.

FIG. 8 illustrates an alternative design of a band 160A. The band 160A is similar to or identical to the band 160 as discussed above in many respects. The band 160A can include any one, or any combination of features of the band 160. The band 160A can be located on any portion of a patient's body. For example, the band 160A can be positioned at and/or near any location where an IV can be inserted into a patient, including but not limited to, a thigh, foot, calf, wrist, leg, hand, and/or neck, among other body parts.

For example, as shown in FIG. 8, the band 160A can include at least three arms 170A. Alternatively, the band 160A can include one, two, four, five, six, seven, or eight or more arms 170A. The band 160A can include an opening 162A for receiving the hub 101. The opening 162A of the band 160A is generally rectangular, however the opening can include other shapes, such as trapezoidal, square, oval, and/or circular in shape, among other shapes. The band 160A can be used in conjunction with and/or instead of the band 160. For example, the band 160A can form a complimentary band that is configured to receive a supplemental hub. The band 160A can alternatively be mounted, for example, on the back of a patient's hand. Such configurations can be advantageous in situations, for example, in which the patient's arm is not accessible or cannot be easily reached. As shown in FIG. 8, the band 160A can include a plurality of sensors 190A, as described in more detail below.

Figure 9:
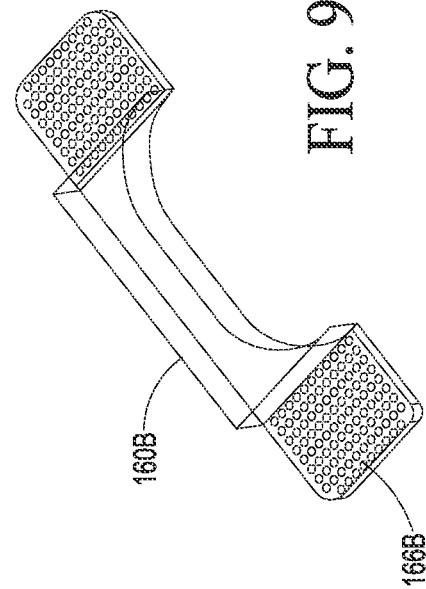
FIG. 9 illustrates a perspective view of a band of a catheter housing device.

FIG. 9 illustrates another embodiment of the band 160B. The band 160B is similar to or identical to the band 160, 160A as discussed above in many respects. The band 160B can include any one, or any combination of features of the band 160, 160A. In some alternative designs, the band 160B forms a multi-purpose attachment strap that can be coupled to the catheter housing 100. The band 160B can include a plurality of contacting structures 166B (e.g., hook and loop fasteners, buckles, or other structures). The band 160B can be located on any portion of a patient's body. For example, the band 160B can be positioned at and/or near any location where an IV can be inserted into a patient, including but not limited to, an arm, thigh, foot, calf, wrist, leg, hand, and/or neck, among other body parts.

Sensors

Figure 10A:
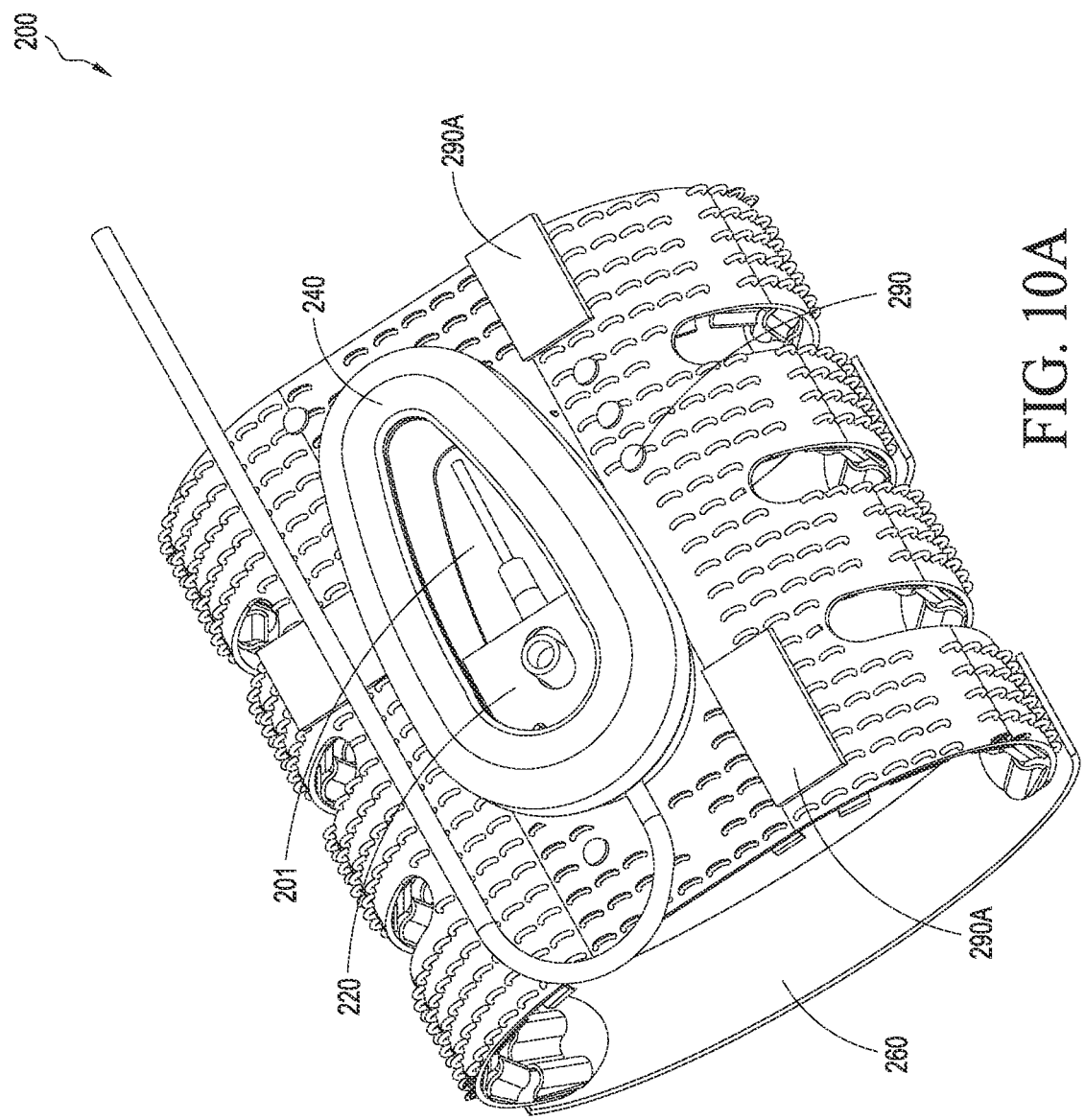
FIG. 10A illustrates a perspective view of a catheter housing device in an assembled form.
Figure 10B:
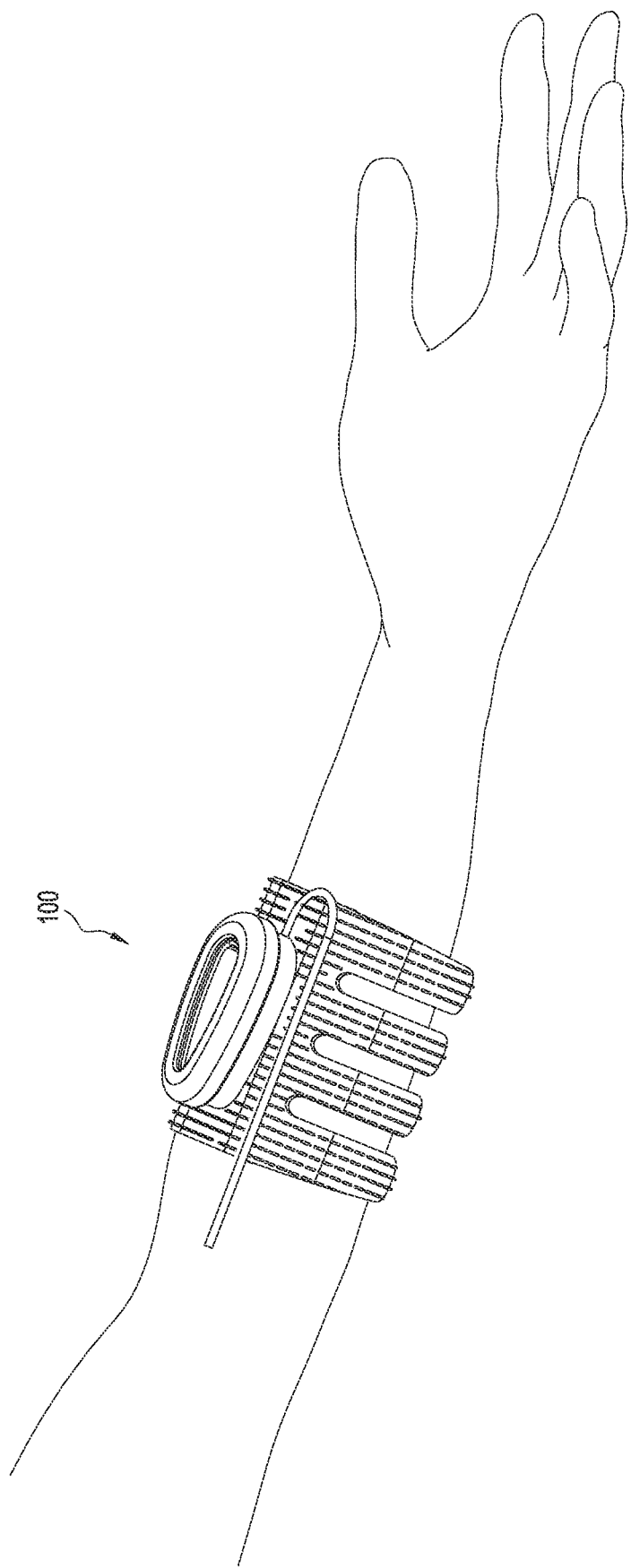
FIG. 10B illustrates a perspective view of a catheter housing device in an assembled form on a human arm.

FIGS. 10A-10B illustrate another example of a stabilizing device 200. The catheter housing 200 (also referred to as "catheter housing device 200" herein) is similar to or identical to the catheter housing 100 discussed above in many respects. As shown in FIGS. 10A-10B, the catheter housing 200 can include a hub 201, a catheter lock 220, a cover 240, and a band 260, which can be respectively similar to the hub 101, the catheter lock 120, the cover 140, and the band 160. The catheter housing 200 can include any one, or any combination of features of the catheter housing 100.

As shown in FIGS. 10A-10B, the catheter housing can wrap around a patient's arm, for example. The catheter housing 200 can include one or more sensors 290. For example, the catheter housing 200 can have one, two, three, four, five, six, seven, eight, nine, ten, eleven, or twelve or more sensors. The one or more sensors sensor 290 can be mounted to and/or otherwise coupled to the hub 201, the catheter lock 220, the cover 240, connecting straps 160B, and/or the band 260.

The sensor 290 can include a temperature sensor (for example, a topical temperature sensor), an artery pressure sensor, a blood oxygen saturation sensor, a sensor for liquid and blood leakage, and/or a skin humidity sensor. The catheter housing 200 can include any one or combination of sensors 190 described herein.

The band 260 can include at least one sensor 290A. The sensor 290A can include one or more bio-sensors. For example, the band 260 can include one, two, three, four, five, six, seven, eight, nine, or ten or more bio-sensors. The bio-sensors can include a micro-processor. For example, the bio-sensors can include an LCD monitor for detecting, measuring, storing and/or displaying patient vital functions, including venous and arterial blood pressure, heart beats, blood oxygen levels, general and topical temperature, and local tissue humidity, and/or venous blood current speed, among others. The measurements and/or calculations performed and/or taken by the at least one sensor 290, 290A can be stored on a flash storage memory positioned on one or more of the band 260, the hub 201, the catheter lock 220, or the cover 240. Alternatively, the sensor measurements can be wirelessly transmitted to a patient monitoring system for analysis, management, organization, and/or display to a care provider or user. Alternatively, the sensor measurements can be transmitted to a personal communications device, such as a tablet or smart device, or a software application or website.

EXAMPLE METHOD

Figure 11:
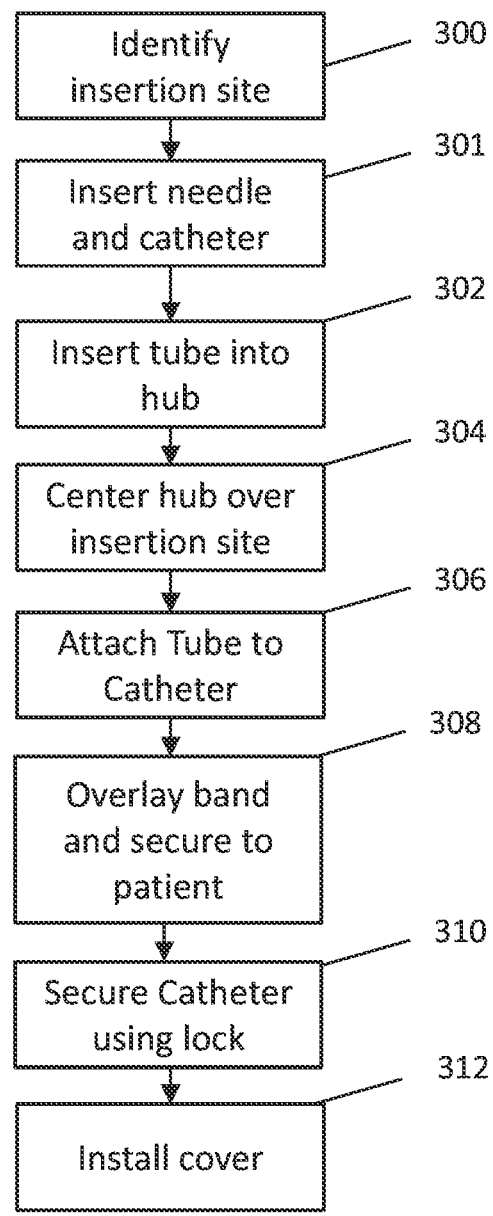
FIG. 11 illustrates a method of providing and removing a catheter housing device.

FIG. 11 illustrates an example method of implementing the catheter housing 100 and/or 200. First, a care provider or other person identifies the appropriate insertion site (step 300), whether it is on an arm, wrist, hand, leg, or other site on a body. At block 301, the needle and catheter are inserted into the patient to establish a line (for example, an IV and/or other fluid supply or withdrawal line). Before or after the needle/catheter is inserted into the patient, catheter tubing can be inserted or coupled to the hub 101 at block 302. Thus, the step described in block 301 can come before or after the step described in block 302. At block 304, the hub 101 is centered over the insertion site. As discussed previously, the hub 101 and/or the catheter housing 100 can be positioned at and/or near any location where an IV can be inserted into a patient. As described above, the hub 101 can be positioned to surround the insertion site and at least a portion of the catheter. Thus, the hub 101 can be advantageously positioned such that a seal is formed around the insertion site and/or catheter. The hub 101 can be provided to the patient before and/or after a catheter is coupled to the needle at the insertion site. For example, if a catheter is already in place, the catheter can be fed through the tubing port and/or tubing port separation 103 of the hub 101 and can be configured to slide over the catheter and form a seal. If a catheter is not already properly positioned, the hub 101 can be provided to the patient and at least partially secured in place before the needle and catheter are inserted. In such configurations, the tubing can then slide through the tubing port and/or tubing port separation 103 in the hub 101.

At block 306, the catheter tube is connected to the catheter. At block 308, the band 160 is laid over the hub 101 and secured to the patient. At block 310, the catheter lock 120 is coupled with the main body 102 and/or with the catheter hub 101 to lock the catheter in place as described herein. It should be understood that block 310 and block 308 can be switched. In other words, the catheter lock 120 can be coupled with the main body 102 and/or with the catheter hub 101 to lock the catheter in place as described herein (block 310) prior to the overlaying and securement of the band 160 to the patient (block 308). Additionally, block 306 can occur before or after block 310 and/or 308. At block 312, the cover 140 is releasably installed over the hub 101 to seal the hub 101 from the outside environment and protect it from contamination. Alternatively, the cover 140 can be installed before the band 160 is laid over the hub 101 and secured in place. Block 312 can occur before or after block 306, block 308, and/or block 310.

When it is time to remove the catheter, the band can be released and removed from the patient. The entire remaining catheter stabilizing device can then be removed, removing the catheter and tubing as well. This allows for quick and efficient removal of the catheter without causing undo discomfort to the patient. Moreover, it should be understood that the entire catheter housing 100, including the band 160, can also be removed in one step. Further, a care provider can also disassemble and remove the catheter housing 100 while the catheter remains in place or before or after the catheter is removed from the patient.

Alternative Design of a Catheter Housing Device

There are a number of alternative designs for the catheter housing discussed above. Some of these alternative designs are further discussed below. One advantage of the alternative designs described below is the reduction in the number of parts/components that comprise the catheter housing. This in turn simplifies the assembly and disassembly process of the device. It should be understood that all features described above are equally applicable to the designs described below. Thus any feature described with respect to FIGS. 1 through 11 are equally applicable to the rest of the figures described herein.

As discussed above, the catheter housing described herein does not use adhesives and avoids applying pressure directly to the needle and/or the insertion site. Because the stabilization system does not use adhesives and does not apply any tape or other layers in the immediate needle insertion area, potential contamination is dramatically reduced. Moreover, because the catheter is not covered with tape, the insertion area can remain readily visible to a care provider. This visibility allows the care provider to easily, quickly, and repeatedly assess the insertion site for signs of inflammation, failure or infection. The disclosed catheter housing also mechanically isolates the catheter from patient movement and holds the catheter at the proper insertion angle. The disclosed catheter housing also provides a securement system that is highly breathable, allowing for patient comfort and reduced skin irritation.

Figure 12A:
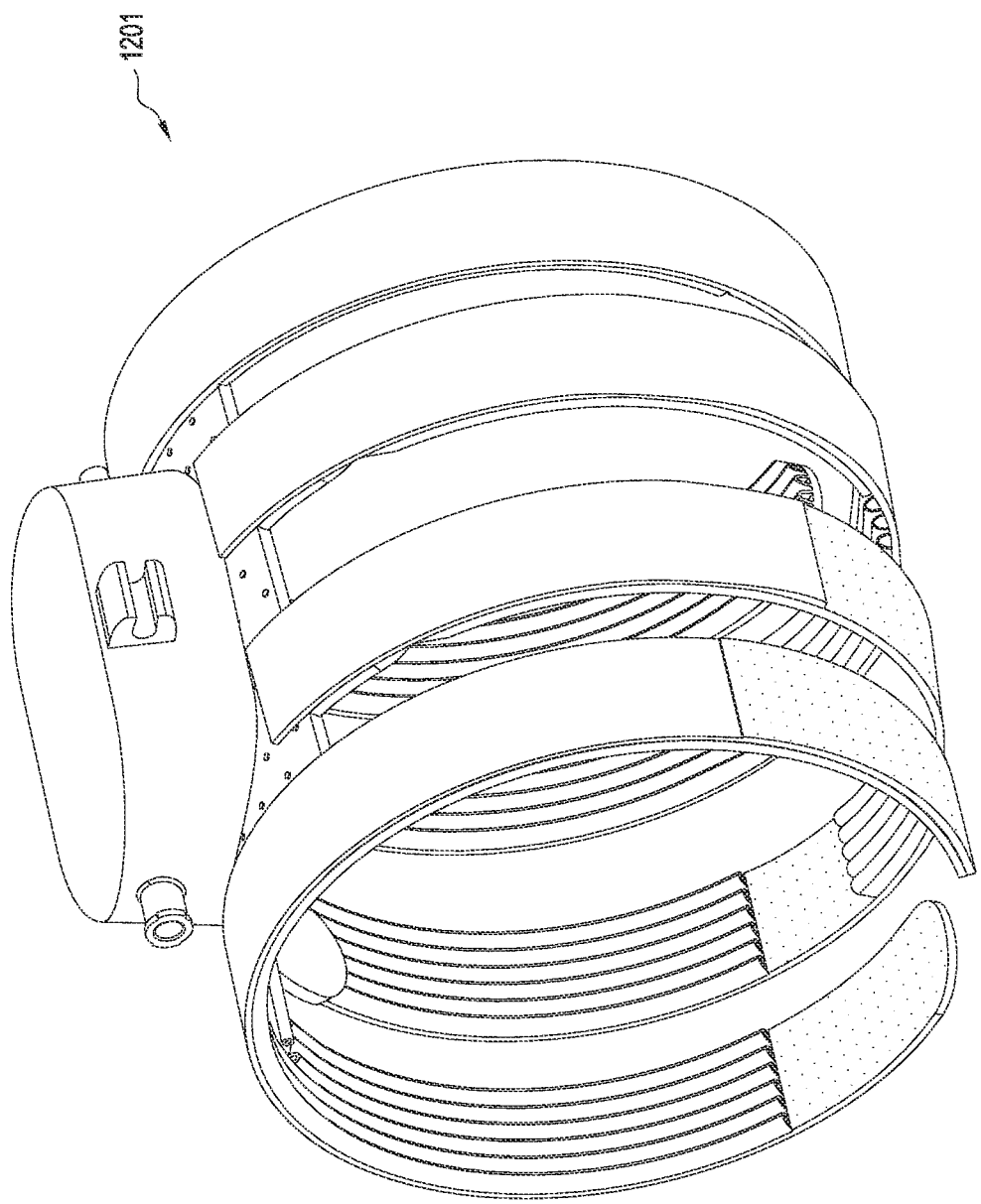
FIG. 12A illustrates a perspective view of an alternative design of a catheter housing device.

FIG. 12A illustrates a perspective view of a fully assembled alternative design for a catheter housing device (also referred to as a "catheter housing" herein) 1201 that can be placed over any portion of a human's body, such as an arm or leg.

Figure 12B:
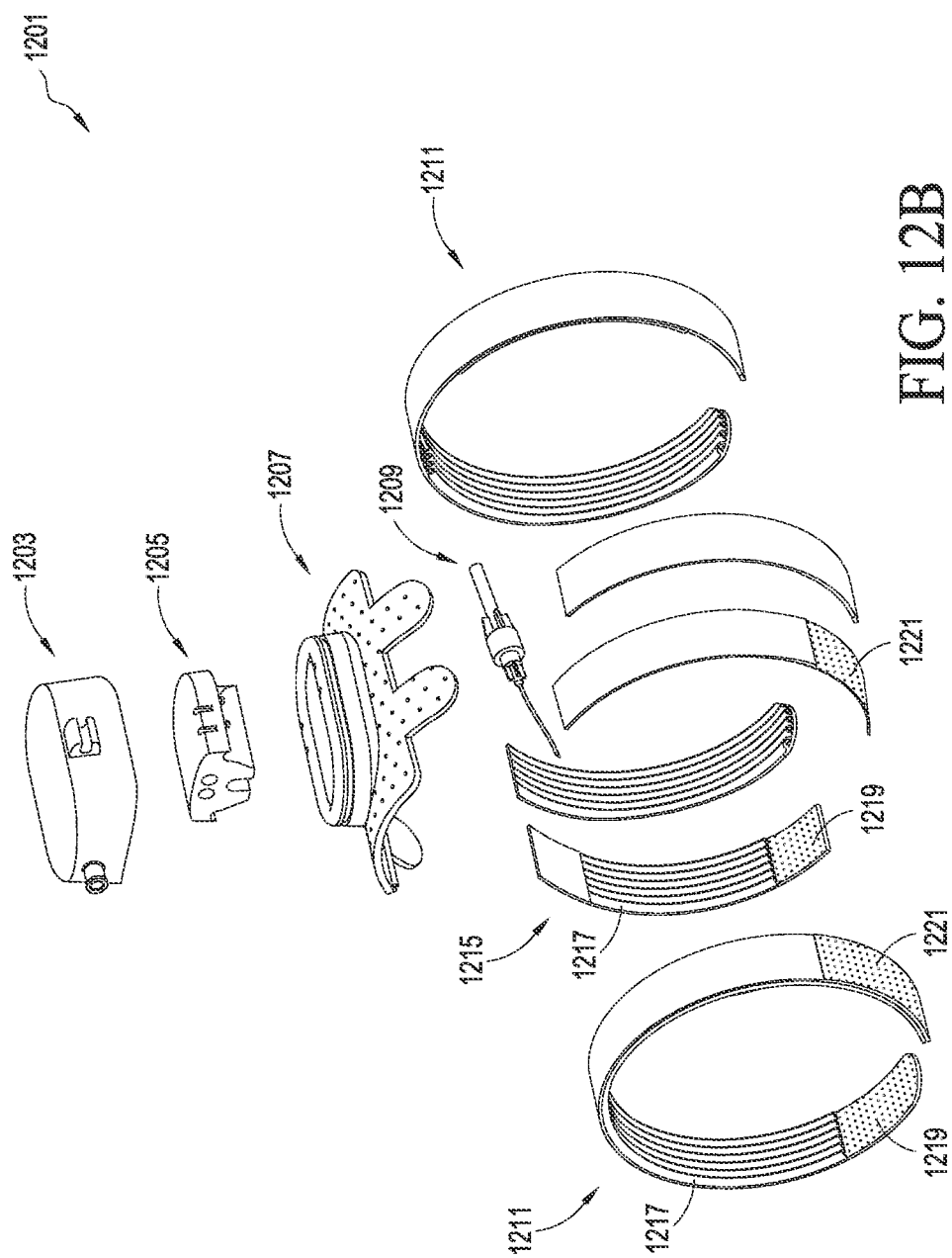
FIG. 12B illustrates an exploded perspective view of an alternative design of a catheter housing device.

FIG. 12B illustrates an exploded view of the catheter housing 1201 of FIG. 12A. The catheter housing 1201 can have a cover 1203, a catheter lock component 1205, a hub component 1207, a full-length fastening strap 1211, and a partial-length fastening strap 1215. The catheter housing can be configured to secure a catheter device which can include a fluid tube connector 1209 or a portion thereof. The catheter housing 1201 can be configured such that a catheter device 1209 is secured to the catheter lock component 1205. The catheter lock component 1205 can be secured to the cover 1203 or the hub component 1207, or both the cover 1203 and the hub component 1207. The cover 1203 can be secured to the hub component 1207 or the catheter lock component 1205, or both the hub component 1207 and the catheter lock component 1205. As illustrated in FIGS. 12A and 12B, when the catheter housing 1201 is assembled, the cover 1203 can substantially surround or enclose the catheter lock component 1205 and/or a portion of the hub component 1207. The hub component 1207 can have an opening 1525 that allows the catheter device 1209 to be inserted in a patient while secured to at least a portion of the catheter housing 1201, for example, the catheter device 1209 can be secured to the catheter lock component 1205. The hub component 1207 can secure to one or more fastening straps, such as one or more full-length fastening straps 1211 or one or more partial-length fastening straps 1215, or both one or more full-length fastening straps 1211 and one or more partial-length fastening straps 1215. Alternatively, the hub component 1207 can be integrally formed with the one or more full-length fastening straps 1211 and/or the one or more partial-length fastening straps 1215. Alternatively, the catheter housing 1201 can have a hub component 1207 that includes one or more bands which can be used to wrap around or otherwise secure to a patient in a manner similar to the manner described below regarding the one or more full-length fastening straps 1211 and/or the one or more partial-length fastening straps 1215.

Figure 12C:
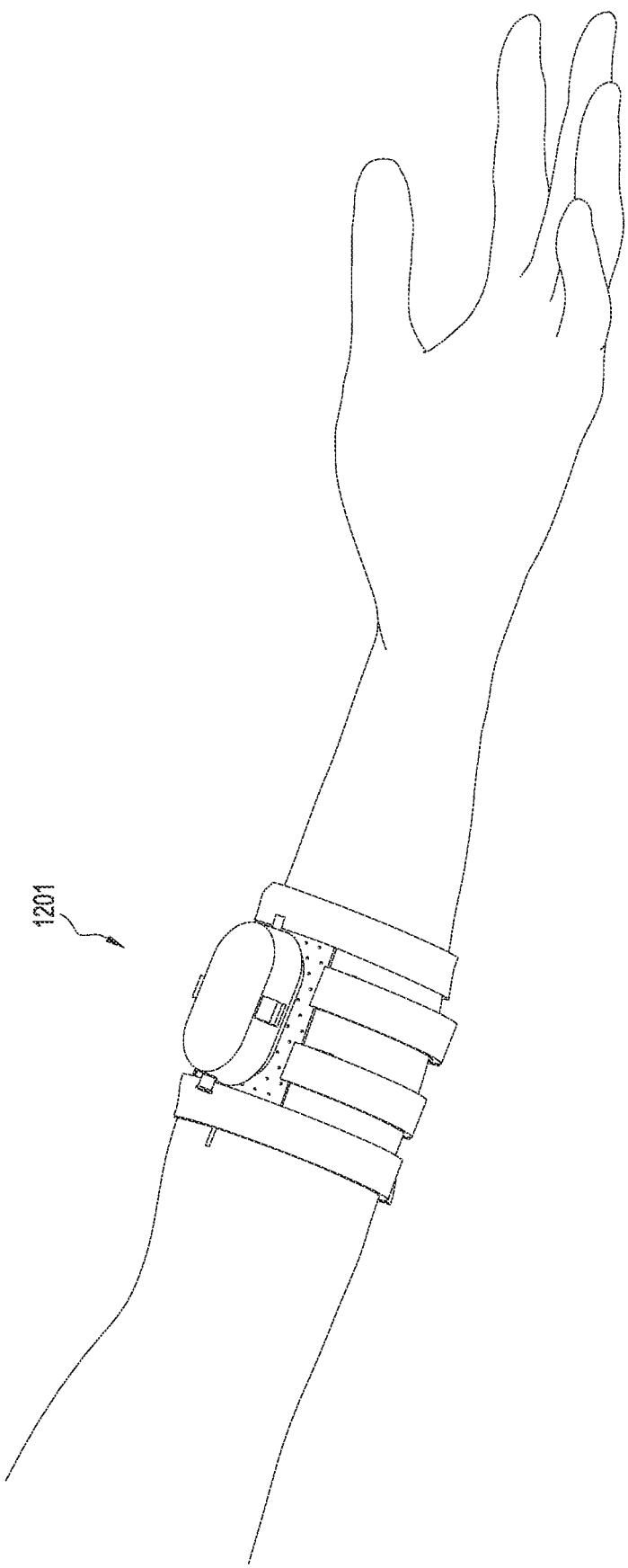
FIG. 12C illustrates a perspective view of alternative design of a catheter housing device in an assembled form on a human arm.

FIG. 12C illustrates a perspective view of a fully assembled catheter housing 1201 while secured to a human arm. As discussed above, the catheter housing 1201 can also be attached to other locations on a human body, such as appendages like a thigh, foot, calf, wrist, leg, hand, and/or neck, among other body parts. For example, the catheter housing 1201 can be attached to various body parts and surround catheter insertion sites located in different regions on a human body, such as near the wrist or elbow-joint area, among other areas. The catheter housing 1201 can be positioned and/or secured at and/or near any location where an IV can be inserted into a patient.

Figure 12D:
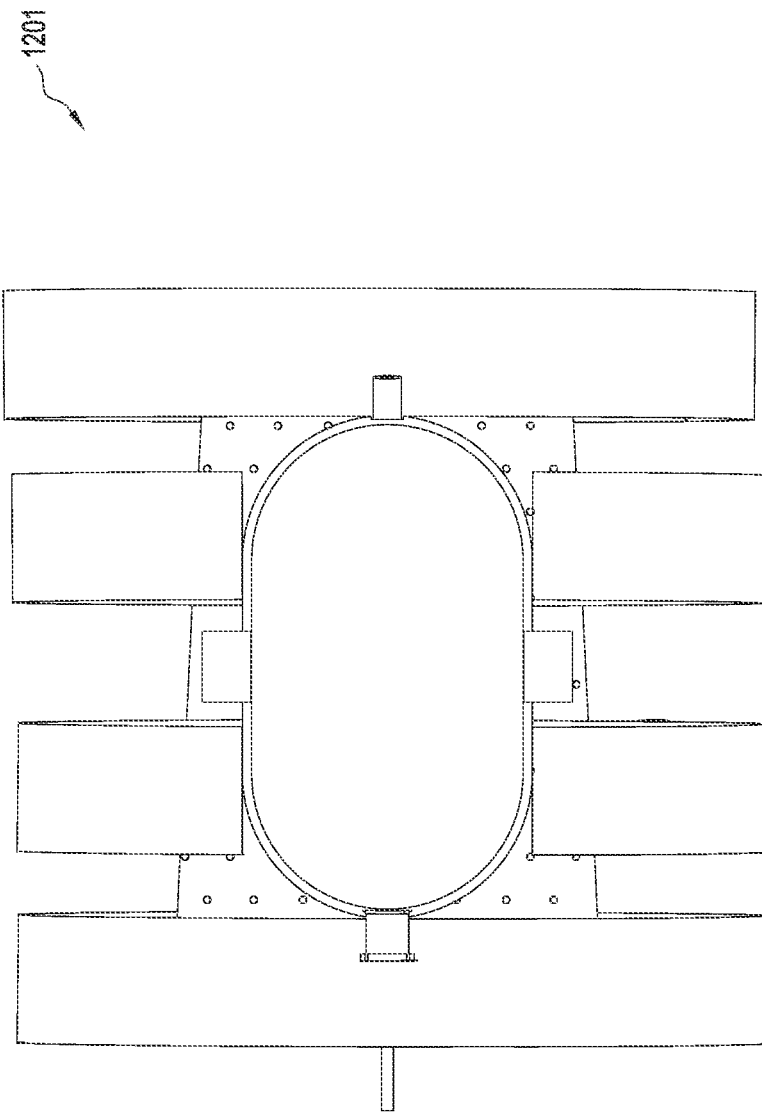
FIG. 12D illustrates a top perspective view of an alternative design of a catheter housing device in an assembled form.

FIG. 12D illustrates a top perspective view of the catheter housing 1201 of FIG. 12A. The catheter housing 1201 described herein can be integrally formed or unitary in structure. For example, the catheter housing 1201 described herein can have a cover 1203, a catheter lock component 1205, a hub component 1207, and one or more fastening straps which comprises a single unit or structure. Additionally, portions of the catheter housing 1201 described herein can comprise a unitary structure. For example, the catheter lock component 1205 and the hub component 1207 can comprise a unitary structure. Additionally, the cover 1203, the catheter lock component 1205 and the hub component 1207 can comprise a unitary structure, for example, they can comprise a housing that secures to a patient and surrounds an insertion site.

Fastening Straps

The catheter housing 1201 can have one or more full-length fastening straps 1211 and/or one or more partial-length fastening straps 1215. For example, the catheter housing 1201 can have one, two, three, four, five, sex, seven, eight, nine, or ten or more full-length fastening straps 1211 and/or one or more partial-length fastening straps 1215. Alternatively, the catheter housing 1201 can have both one or more full-length fastening straps 1211 and one or more partial length fastening straps 1215. These fastening straps can be made from a variety of material or combination of materials. For example, the fastening straps can comprise silicone, plastic, rubber, and/or fabric. Alternatively, the fastening straps can comprise appropriate FDA approved materials. Alternatively, the fastening straps can comprise medical grade soft silicone material. Additionally, the fastening straps can be substantially waterproof, durable, and/or washable. The one or more fastening straps can contain information regarding a patient, such as name, birthdate, and other information.

The full-length fastening straps 1211 and partial-length fastening straps 1215 can include a ventilation portion 1217. The ventilation portion 1217 can exist on the underside of the fastening straps, which can be the side that contacts the skin of a patient. The ventilation portion 1217 can include one or more corrugated protrusions that can facilitate ventilation underneath and around the fastening straps. For example, the ventilation portion 1217 can include one, two, three, four, five, six, seven, eight, nine, ten, eleven or more corrugated protrusions. The ventilation portion 1217 can have corrugated protrusions that extend along a perimeter of the fastening straps. Alternatively, the ventilation portion 1217 can have corrugated protrusions that extend in a direction perpendicular to the perimeter of the fastening strap. Alternatively, the corrugated protrusions can extend partially in both a parallel and perpendicular direction to the perimeter of the fastening straps. The corrugated protrusions of the ventilation portion 1217 can be continuous or intermittent (i.e., noncontinuous), and can be located in different locations along the underside of the fastening straps. For example, the ventilation portion 1217 can be located at one end of the fastening strap, or can be located along a middle portion of the fastening strap. The ventilation portion 1217 can also include any of the structures described with respect to FIGS. 1-11 above, including, for example, suction cups.

The full-length fastening straps 1211 and/or partial-length fastening straps 1215 can include one or more underside securement portions 1219 and one or more exterior securement portions 1221. For example, the full-length fastening straps 1211 and/or partial-length fastening straps 1215 can include one, two, three, four, five, six, seven, eight, nine, ten, eleven or more underside securement portions 1219 and one or more exterior securement portions 1221. The underside securement portion 1219 can be continuous or noncontinuous and can extend along the underside of the fastening straps (i.e., the portion of the fastening strap that contacts the skin of a patient when the fastening straps are secured to a patient). The underside securement portion 1219 can be located in different locations along the underside of the fastening straps. For example, the underside securement portion 1219 can be located at one end of the fastening strap, or can be located along a middle portion of the fastening strap. The exterior securement portion 1221 can be continuous or noncontinuous and can extend along the exterior of the fastening straps. The exterior securement portion 1221 can be located in different locations along the exterior of the fastening straps. For example, the exterior securement portion 1221 can be located at one end of the fastening strap, or can be located along a middle portion of the fastening strap.

The underside securement portion 1219 and exterior securement portion 1221 can comprise various securement means. For example, the underside securement portion 1219 and/or exterior securement portion 1221 can comprise hook and loop fasteners, clips, buckles, fungi-like attachment, or other known attachment systems, or a combination of these attachment systems. For example, the underside securement portion 1219 and/or exterior securement portion 1221 can comprise Velcro. Alternatively, the underside securement portion 1219 and exterior securement portion 1221 can comprise an adhesive attachment system.

The underside securement portion 1219 and exterior securement portion 1221 can be configured to attach and detach from one another. For example, the underside securement portion 1219 can attach underneath the exterior securement portion 1221. Alternatively, the underside securement portion 1219 can attach overtop of the exterior securement portion 1221. Alternatively, the underside securement portion 1219 and exterior securement portion 1221 can secure to one another in another fashion, such as side-by-side.

The one or more full length fastening straps 1211 and the one or more partial length fastening straps 1215 can be configured to at least partially secure to the hub component 1207 and/or the catheter housing 1201. For example, the full-length fastening straps 1211 can secure to a front portion of the hub component 1207, or a back portion of the hub component 1207, or both a front and back portion of the hub component 1207. The full-length fastening straps 1211 can secure to at least a portion of the hub component 1207 and also be secured to itself. For example, as illustrated in FIGS. 12A and 12B, an underside securement portion 1219 of the full-length fastening strap 1211 can secure to at least a portion of the hub component 1207 and an underside securement portion 1219 can also secure to an exterior securement portion 1221 of the full-length fastening strap 1211. As also illustrated in FIGS. 12A and 12B, one or more partial-length fastening straps 1215 can secure to at least a portion of the hub component 1207. For example, an underside securement portion 1219 of a partial-length fastening strap 1215 can secure to at least a portion of the hub component 1207, and another underside securement portion 1219 of the same partial length fastening strap can secure to an exterior securement portion 1221 of a different partial-length fastening strap 1215.

As discussed above, the catheter housing 1201 can include one or more fastening straps. For example, the catheter housing 1201 can include two full-length fastening straps 1211 and four partial length fastening straps 1215. To facilitate comfort of the patient secured to the catheter housing 1201, one or more of the fastening straps can be detached for a given time. For example, one or more full-length fastening straps 1211 can be detached so as to relieve pressure imposed from the attached catheter housing 1201. Alternatively, one or more of the partial-length fastening straps 1215 can be detached so as to relieve pressure imposed from the attached catheter housing 1201. The catheter housing 1201 can be configured to alternate the securement of the fastening straps while maintaining securement of the device to a patient. The one or more fastening straps disclosed herein can be used as a tourniquet to help a caregiver locate a patient's vein without needing any other equipment such as tools, devices, bands, or other devices. A caregiver can attach, adhere, secure, and/or write patient information on the one or more fastening straps disclosed herein. The caregiver can also place or write the insertion date and time on the one or more fastening straps.

Cover

Figure 13A:
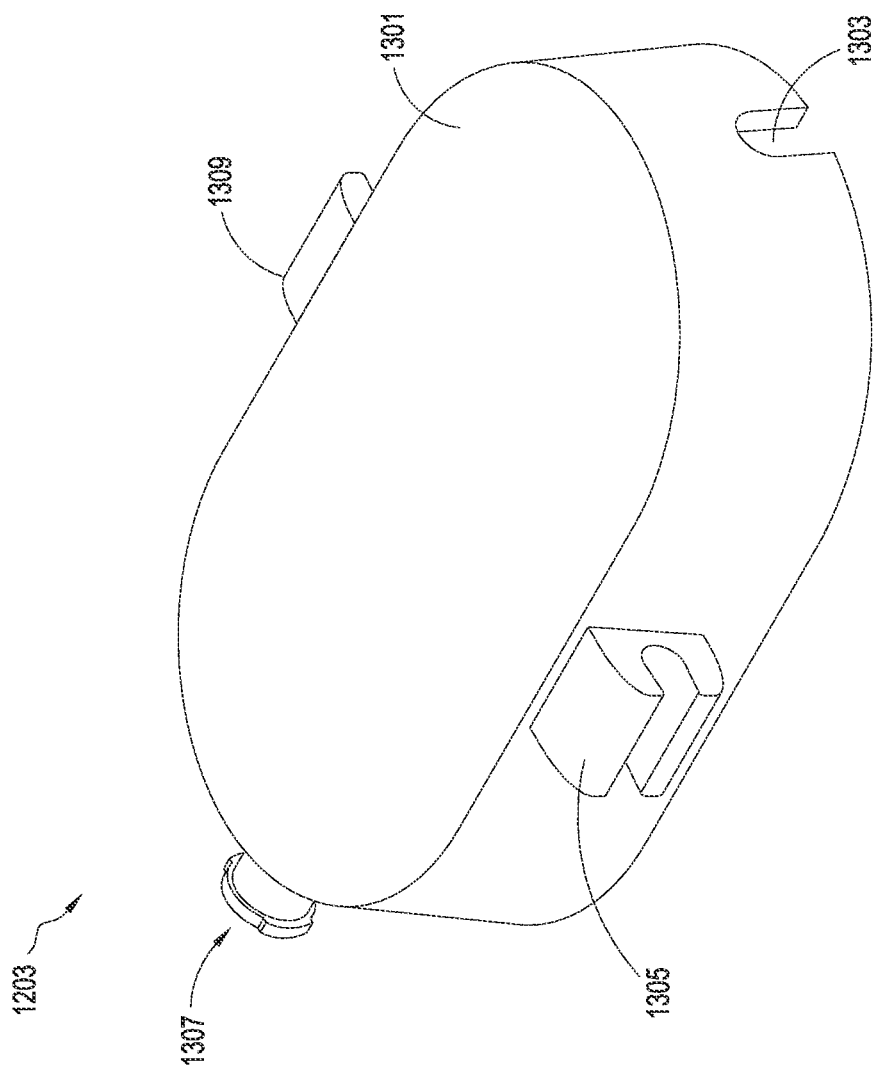
FIG. 13A illustrates a perspective view of a cover of an alternative design of a catheter housing device.
Figure 13C:
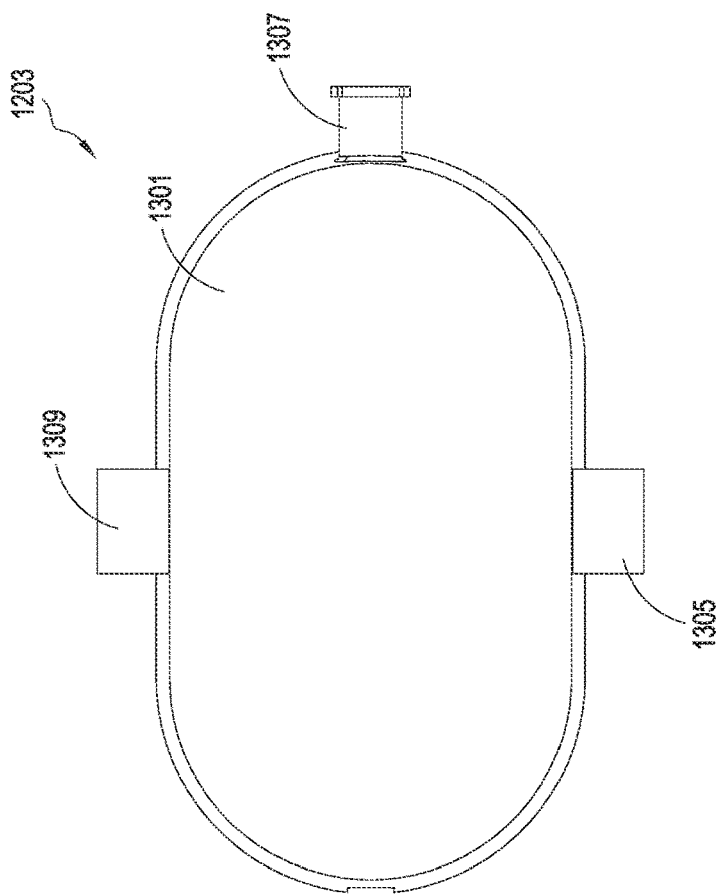
FIG. 13C illustrates a top perspective view of a cover of an alternative design of a catheter housing device.
Figure 13B:
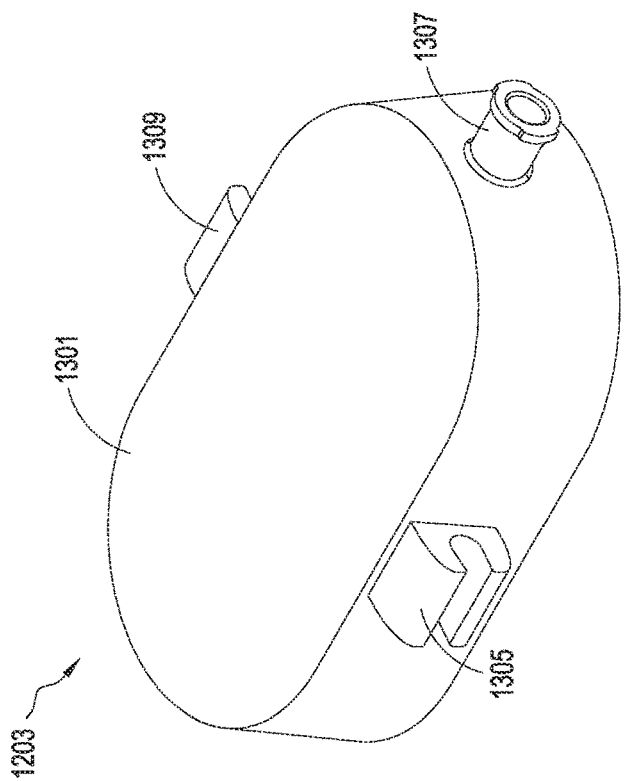
FIG. 13B illustrates another perspective view of a cover of an alternative design of a catheter housing device.

FIGS. 13A and 13B illustrate perspective views of a cover 1203 of the catheter housing 1201 of FIG. 12A. The cover 1203 can be configured to secure to the catheter lock 1205 or the hub component 1207, or both the catheter lock component 1205 and the hub component 1207. Alternatively, the cover 1203 can be configured to secure to a full-length fastening strap 1211 and/or a partial-length fastening strap 1215.

The cover 1203 can be made of transparent material. Alternatively, the cover can be made of nontransparent material. Additionally, the cover 1203 can be comprise both transparent and nontransparent material. For example, the portions of the cover can be made of transparent material where it is advantageous to be able to see through the cover in order to observe the other components of the catheter housing 1201. The cover 1203 can be made of substantially shockproof and/or durable material. This is advantageous because the catheter housing 1201 and the cover 1203 can be subjected to impact during installation or use. The cover 1203 can also be made of substantially waterproof material. This is advantageous because the catheter housing 1201 and the cover 1203 can be subjected to water or other liquids when the device is in use. The cover 1203 can comprise plastic, rubber, and/or silicone, among other materials, or a combination of such materials. The cover 1203 can comprise of a soft, pliable material, such as medical grade silicone. Alternatively, the cover 1203 can comprise harder silicone, or rubber can be used.

The cover 1203 can be configured to form a closed environment over a site where an intravenous catheter is inserted into a patient. Such a closed environment can aid in keeping the site free from contamination. As discussed above, the cover 1203 can be made of at least partially transparent material so as to allow a caregiver or other person to examine the catheter insertion site and/or other portions of the catheter housing 1201 (e.g., the hub component 1207 and/or the catheter lock component 1205) while the cover 1203 is secured to the hub component and/or the catheter lock component 1205.

The cover 1203 can comprise a cover body 1301 and a catheter tube slot 1303. The cover body 1301 can have a rounded shape. Alternatively, the cover body 1301 can have a non-round shape, for example, a rectangular shape. Alternatively, the cover body 1301 can be approximately trapezoidal, rectangular, square, oval and/or circular in shape, among other shapes. The cover 1203 can comprise a single, continuous piece. Alternatively, the cover 1203 can comprise more than one piece. The catheter tube slot 1303 can permit a catheter tube, an intravenous line, or other device to pass through the cover body 1301. For example, the catheter tube slot 1303 can permit a catheter tube, an intravenous line, or other device to pass through the cover body 1301 when the cover is secured to the hub component 1207 and/or the catheter lock component 1205.

The cover 1203 can have one or more ports 1307 which can be used to insert sterilizing and/or anesthetic gas into the catheter housing 1201. For example, the cover 1203 can have one, two, three, four, five, six, seven, eight, nine, ten, eleven or more ports 1307. The one or more ports 1307 can be located on a side of the cover 1203. Alternatively, the one or more ports 1307 can be located on a top portion of the cover 1203. The one or more ports 1307 can be used to provide sterilization gases, such as ethylene oxide gas, hydrogen peroxide gas plasma, or other sterilizing or anesthetic gases. For example, the cover 1203 can include a port 1307 for providing sterilizing gases, and a separate port for providing anesthetic gases.

The cover 1203 can include a catheter tube holder 1305. The catheter tube holder 1305 can be located on a side of the cover body 1301. Alternatively, the catheter tube holder 1305 can be located on a top portion of the cover body 1301. The catheter tube holder 1305 can be configured to secure one or more catheter tubes, or other tubes or devices. The cover 1203 can include a gas tube holder 1309, which can be located on a side and/or a top portion of the cover body 1301. The gas tube holder 1309 can be configured to secure one or more gas tubes, or other tubes or devices.

Figure 13D:
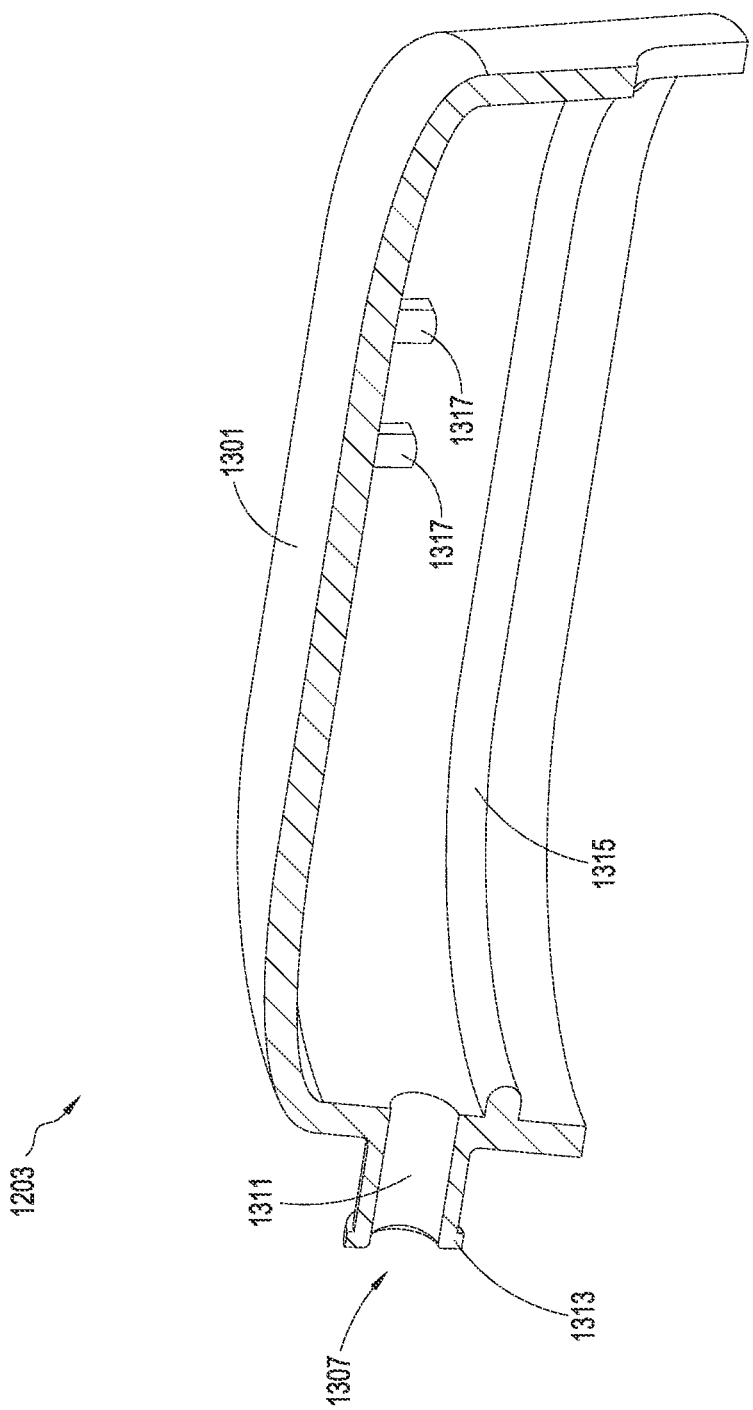
FIG. 13D illustrates a cross-section perspective view of a cover of an alternative design of a catheter housing device.

FIG. 13D illustrates a cross-section of the cover 1203. The cover 1203 can include one or more protrusions 1315. For example, the cover 1203 can include one, two, three, four, or five or more protrusions 1315. In one alternative design, the cover 1203 can have one protrusion 1315. The protrusion 1315 can extend along an interior portion of the cover 1203. The protrusion 1315 can be located at a lower interior portion of the cover 1203, or alternatively, the protrusion 1315 can be located at a middle or higher interior portion of the cover 1203. The protrusion 1315 can be substantially continuous, or alternatively, can be noncontinuous, intermittent or exist in sections. The protrusion 1315 can be configured to secure to at least a portion of the catheter lock component 1205 and/or the hub component 1207. For example, such securement can occur when the cover 1203 is placed over the catheter lock component 1205 and the hub component 1207, so as to encompass both the catheter lock component 1205 and the hub component 1207, and secure to the hub component 1207, whereby the protrusion 1315 can secure to a peripheral groove 1517 of the hub component 1207 (see FIG. 15C). The protrusion 1315 can secure to the peripheral groove 1517 by a snap-fit, press fit, and/or other configuration for securely connecting the cover 1203 to the hub component 1207.

Alternatively, the protrusion 1315 can be replaced with one or more interior grooves (not shown in figures). For example, the protrusion 1315 can be replaced with one, two, three, four, or five, six, seven, or eight or more grooves. Alternatively, the protrusion 1315 can be replaced with one groove. Such interior grooves can secure to at least a portion of the catheter lock component 1205 and/or the hub component 1207. For example, such interior grooves can secure to a protrusion appearing on the hub component 1207. Such securement can occur by a snap-fit, press fit, and/or other configuration. Thus, the cover 1203 can secure to the catheter lock component 1205 and/or the hub component 1207 by insertion of a protrusion located on the cover 1203, or by accepting a protrusion located on the catheter lock component 1205 and/or the hub component 1207.

As further illustrated in FIGS. 13A, 13B, and 13D, the cover 1203 can include one or more ports 1307. The one or more ports 1307 can be substantially cylindrical, rectangular, or another shape. The one or more ports 1307 can include a gas opening 1311 which permits sterilizing gas, anesthetic gas, or other gases, to flow into the catheter housing 1201. The one or more ports 1307 can include a port rim 1313 that extends at least partially around an exterior portion of the one or more ports 1307. The port rim 1313 can extend radially outward from the one or more ports 1307. The port rim 1313 can be located at an end of the one or more ports 1307 (as shown in FIG. 13D) or, alternatively, at another region along the one or more ports 1307. The one or more ports 1307 can extend outwardly from the cover body 1301. The port rim 1313 can be configured to secure to gas tubes or other devices that provide gas to the catheter housing 1201. For example, the port rim 1313 can contain one or more threads by which a gas tube or other device can screw into. Alternatively, the port rim 1313 can comprise a snap mechanism that can secure to a gas tube or other device, whereby a portion of such tube or other device can be configured to snap into or around the snap mechanism of the port rim 1313. Other alternative methods of securing a gas tube or other device to the port rim 1313 of the one or more ports 1307 exist. The one or more ports 1307 can also include one or more valves, such as a control valve and/or a multi-valve.

The cover 1203 can include one or more interior notches 1317. For example, the cover 1203 can include one, two, three, four, five, six, seven, eight, nine, ten, eleven or more notches 1317. The one or more interior notches 1317 can be located along the interior sides of the cover 1203. Alternatively, the one or more interior notches 1317 can be located on the interior top wall of the cover 1203. In one alternative design, the one or more interior notches 1317 can be located along the interior sides of the cover 1203 and can be configured to align with one or more slots 1403 located on the catheter lock component 1205 (see FIGS. 13D and 14C). The one or more interior notches 1317 can align with the one or more slots 1403 so that the catheter lock component 1205 and the cover 1203 are secured to one another. The one or more interior notches 1317 can be cylindrical, rectangular, or another shape, and can extend outward from an interior side of the cover 1203. The one or more interior notches 1317 can extend along the interior side of the cover 1203. The one or more interior notches 1317 can be configured to secure to the one or more slots 1403 located on the catheter lock component 1205 by a snap-fit, press fit, and/or other configuration. For example, the catheter lock component 1205 can include one, two, three, four, five, six, seven, eight, nine, ten, eleven or more slots 1403.

In some configurations, a seal is formed such that the cover 1203 does not allow external air and/or contaminants from entering the enclosed internal volume of the catheter housing 1201. For example, the cover 1203 can engage the catheter lock component 1205 and/or the hub component 1207 to form a closed and/or isolated atmosphere, which encloses the insertion site. In such configurations, the insertion site can advantageously be sterilized by inert gas as described above. Similarly, the cover 1203 can advantageously help to inhibit or prevent microbe contaminate and help to lower contamination vulnerability. The cover 1203 can also be configured to prevent the joint 1510 from separating while the catheter housing 1201 is in use.

Catheter Lock Component

Figure 14D:
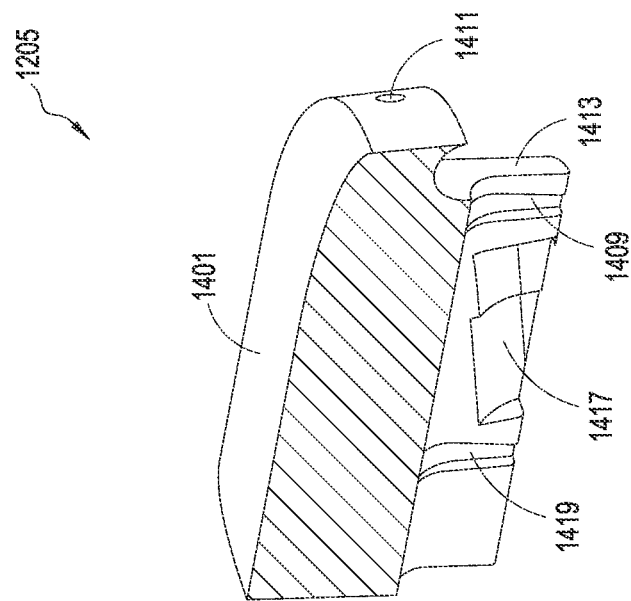
FIG. 14D illustrates a cross-section perspective view of a catheter lock component of an alternative design of a catheter housing device.
Figure 14C:
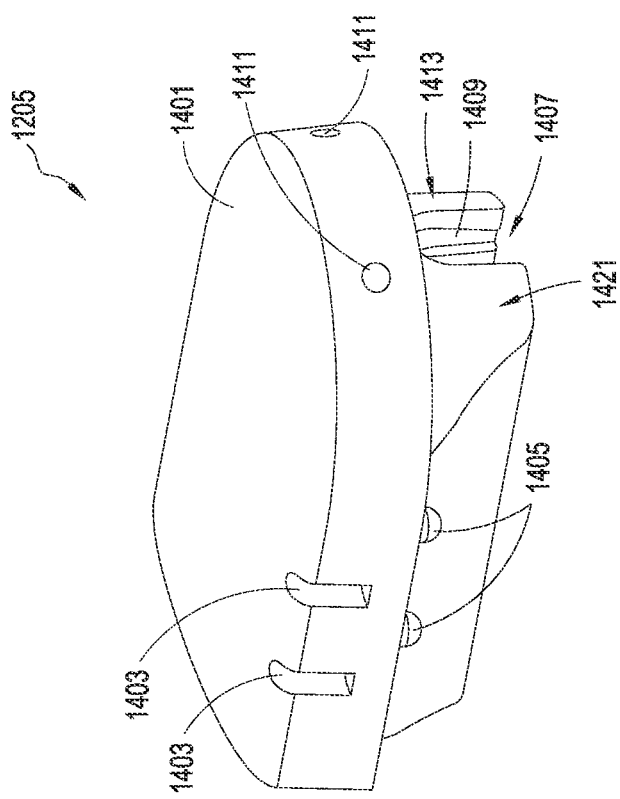
FIG. 14C illustrates a perspective view of a catheter lock component of an alternative design of a catheter housing device.

FIGS. 14A through 14L illustrate various perspectives of the catheter lock component 1205. As shown in FIGS. 14A and 14C, the catheter lock component 1205 can include a catheter lock body 1401, a left jaw 1421, a right jaw 1413, one or more slots 1403, one or more pins 1405, a catheter inlet 1407, a catheter outlet 1408, and a back face 1410.

The catheter lock component 1205 can comprise rigid plastic material, such as a hard plastic, and/or hard rubber, among other hard materials. The catheter lock component 1205 can be made of substantially shockproof and durable material. This is advantageous because the catheter housing 1201 and/or the catheter lock component 1205 can be subjected to impact during installation or use of the device. The catheter lock component 1205 can also be made of substantially waterproof material. This is advantageous because the catheter housing 1201 and/or the catheter lock component 1205 can be subjected to water or other liquids when the device is in use. The catheter lock component 1205 can comprise a clear or transparent material to allow light to spread over the insertion site, for example, through the catheter lock component 1205. The catheter lock component 1205 or portions of the catheter lock component 1205 can also be opaque or partially opaque.

The one or more slots 1403, can be located along an exterior portion of the catheter body 1401. For example, the one or more slots 1403 can be located on one or more sides of the catheter lock component 1205. The one or more slots 1403 can comprise a cylindrical, rectangular, or other shape, so as to engage the one or more interior notches 1317 of the cover 1203. For example, the catheter lock component 1205 can include two slots 1403 on each side of the catheter lock body 1401 to accommodate and secure to two interior notches 1317 on each side of the cover 1203.

FIG. 14C illustrates the catheter lock component 1205 in an upright position. The catheter lock body 1401 can have a top portion, a bottom portion, side portions, and a front portion. The catheter lock body 1401 can also have a back face 1410. The side portions can extend along the perimeter of the catheter lock body 1401. The back face 1410 of the catheter lock body 1401 can be substantially flat (see FIG. 14A). The front portion, which is opposite the back face 1410, can be curved (see FIG. 14C).

As illustrated in FIG. 14C, the one or more pins 1405 can extend downward from a top portion of the catheter lock body 1401. The one or more pins 1405 can be located along the perimeter of the catheter lock body 1401. For example, the one or more pins 1405 can be located along a side of the catheter lock body 1401 (see FIG. 14C). For example, the catheter lock body 1401 can include one, two, three, four, five, six, seven, eight, nine, ten, eleven or more pins 1405. The one or more pins 1405 can be cylindrical, rectangular, or another shape. Additionally, the one or more pins 1405 can have a rounded end. Alternatively, the one or more pins 1405 can have a substantially flat end. Alternatively, the one or more pins 1405 can have a sharp or pointed end. In one alternative design, the catheter lock component 1205 includes two catheter pins on two opposite sides of the catheter lock component 1205 (see FIG. 14E). The one or more pins 1405 can be configured to align with one or more recesses 1515 in the hub component 1207 (see FIG. 15C). For example, the catheter lock component 1205 of FIG. 14C can be secured to the hub component 1207 when the one or more pins 1405 are inserted into the one or more recesses 1515 of the hub component 1207. The one or more pins 1405 can be configured to secure to the one or more recesses 1515 by a snap-fit configuration, press fit configuration, friction fit configuration, and/or other securement structures or methods. The one or more pins 1405 can include one or more ridges (not shown) that can interact with one or more corresponding grooves inside an interior portion of the one or more recesses 1515 so that the one or more pins 1405 are in a locked position when the one or more pins 1405 are secured to the one or more recesses 1515. The one or more pins 1405 can be disengaged, or unlocked from the one or more recesses 1515 when the one or more pins 1405 are subjected to pulling force, so that the one or more ridges of the one or more pins 1405 passes over the corresponding one or more grooves of the one or more recesses 1515. Other connections are possible to secure the one or more pins 1405 of the catheter lock component 1205 to the one or more recesses 1515 of the hub component, and one skilled in the art will be able to recognize them.

The catheter lock component 1205 can include a catheter inlet 1407. The catheter inlet 1407 can permit a catheter or portion thereof to pass into and through the catheter lock component 1205. In one alternative design, the catheter inlet 1407 can align with a hub inlet 1511 when the catheter lock component 1205 is secured to the hub component 1207, thus permitting a catheter or other tube to pass through the hub inlet 1511 and into and through the catheter inlet 1407.

The catheter lock component 1205 can include one or more catheter lights 1411. For example, the catheter lock component 1205 can include one, two, three, four, five, six, seven, eight, nine, ten, eleven or more catheter lights 1411. The one or more lights 1411 can be located on a portion of the catheter lock body 1401. For example, one or more lights 1411 can be located on a top portion or bottom portion of the catheter lock body 1401. Alternatively, the one or more lights 1411 can be located on a side portion of the catheter lock body 1401. Alternatively, the one or more lights 1411 can be located on both a side portion and a top portion of the catheter lock body 1401, or both a side portion and a bottom portion of the catheter lock body 1401, or both a top portion and a bottom portion of the catheter lock body 1401. Alternatively, one or more lights 1411 can be located on a back face 1410 of the catheter lock body 1401. The one or more lights 1411 can be LED.

The one or more lights 1411 can allow the catheter, the catheter housing 1201, or areas in and around the insertion site to be inspected during the day and/or night. The one or more lights 1411 can illuminate a region surrounding or proximate to the catheter housing 1201. For example, the one or more lights 1411 can illuminate a region within 3 feet from the catheter housing 1201. Alternatively, the one or more lights 1411 can illuminate a region within 1 feet from the catheter housing 1201. Alternatively, the one or more lights 1411 can illuminate a region within 5 feet from the catheter housing 1201. The one or more lights 1411 can also indicate that catheter lock component 1205 is properly fit into the hub component 1207 and/or the cover 1203. The one or more lights 1411 can also indicate that the catheter is not properly positioned and/or secured to the patient. For example, the lights can change colors, flash at certain speeds, and/or change brightness to indicate an issue with the catheter lock component 1205 or the catheter.

The catheter lock component 1205 can include one or more cavities 1412 (see FIG. 14A). For example, the catheter lock component 1205 can include one, two, three, four, five, six, seven, eight, nine, ten, eleven or more cavities 1412. The one or more cavities 1412 can extend from a back face 1410 of the catheter lock component 1205 into a portion of the catheter lock component 1205. The one or more cavities 1412 can decrease the total weight of the catheter lock component 1205.

Universal Lock

Figure 14E:
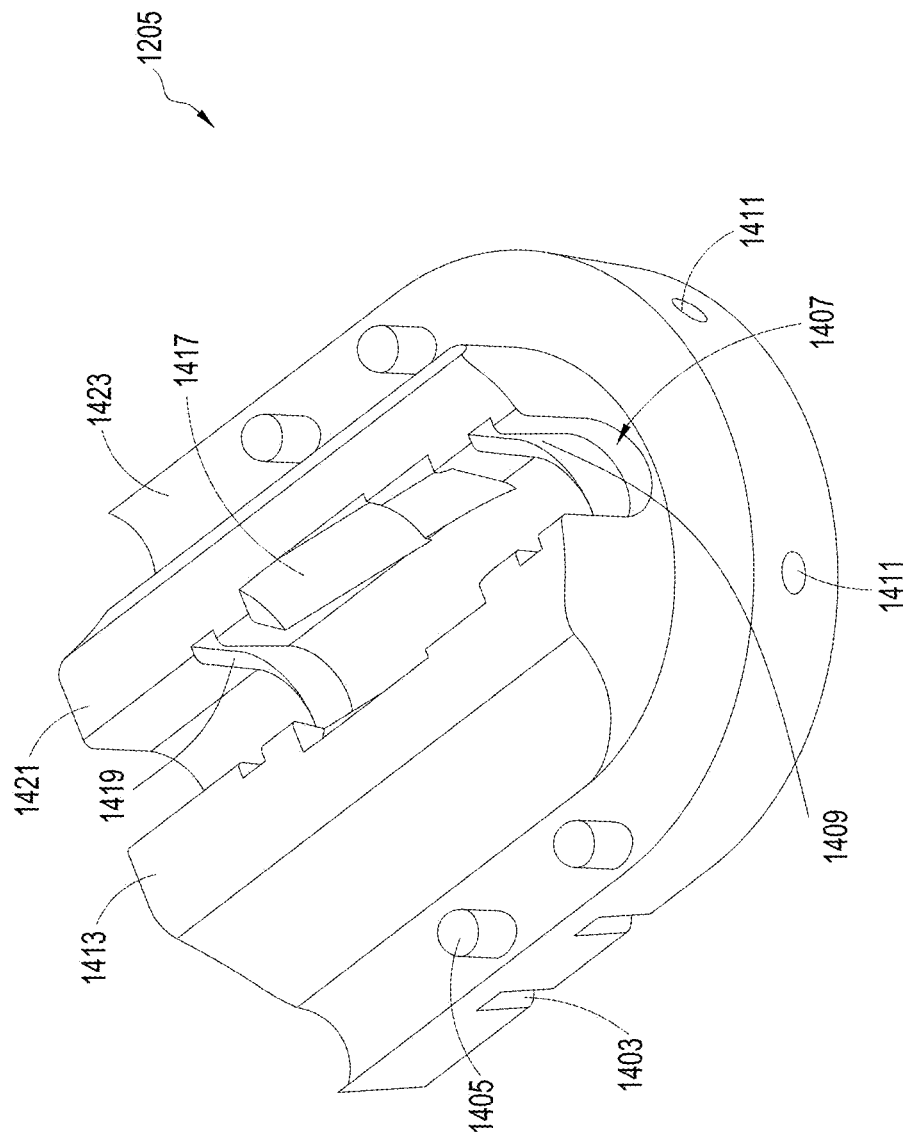
FIG. 14E illustrates a perspective view of an underside of a catheter lock component of an alternative design of a catheter housing device.

FIG. 14D illustrates an interior cross-section of the catheter lock component 1205 of FIG. 14C. As can be seen in FIG. 14E, the catheter lock component 1205 can include one or more recesses that can secure a portion of a catheter, including catheters of different sizes and shapes. The catheter lock component 1205 can be configured to secure a catheter or portion thereof in the proper orientation relative to the patient's skin. The securement of catheter or portion thereof by or with the catheter lock component 1205 can be a physical locking, holding, stabilizing without locking, retaining, stabilizing to prevent or reduce the likelihood of movement, stabilizing to minimize movement, or another type of securement. The catheter lock component 1205 can include one, two, three, four, five, six, or seven or more recesses. The one or more recesses can be located on the bottom surface, a top surface, and/or a side surface of the catheter lock component 1205.

The one or more recesses of the catheter lock component 1205 can be configured to secure a catheter or portion thereof in the proper orientation relative to the patient's skin. The securement of catheter or portion thereof by or with the one or more recesses of the catheter lock component 1205 can be a physical locking, holding, stabilizing without locking, retaining, stabilizing to prevent or reduce the likelihood of movement, stabilizing to minimize movement, or another type of securement. The one or more recesses of the catheter lock component 1205 can include one or more interior grooves for securing a catheter or portion thereof. For example, the one or more recesses of the catheter lock component 1205 can include one, two, three, four, five, six, seven, eight, or nine or more interior grooves for securing a catheter or portion thereof.

Figure 14F:
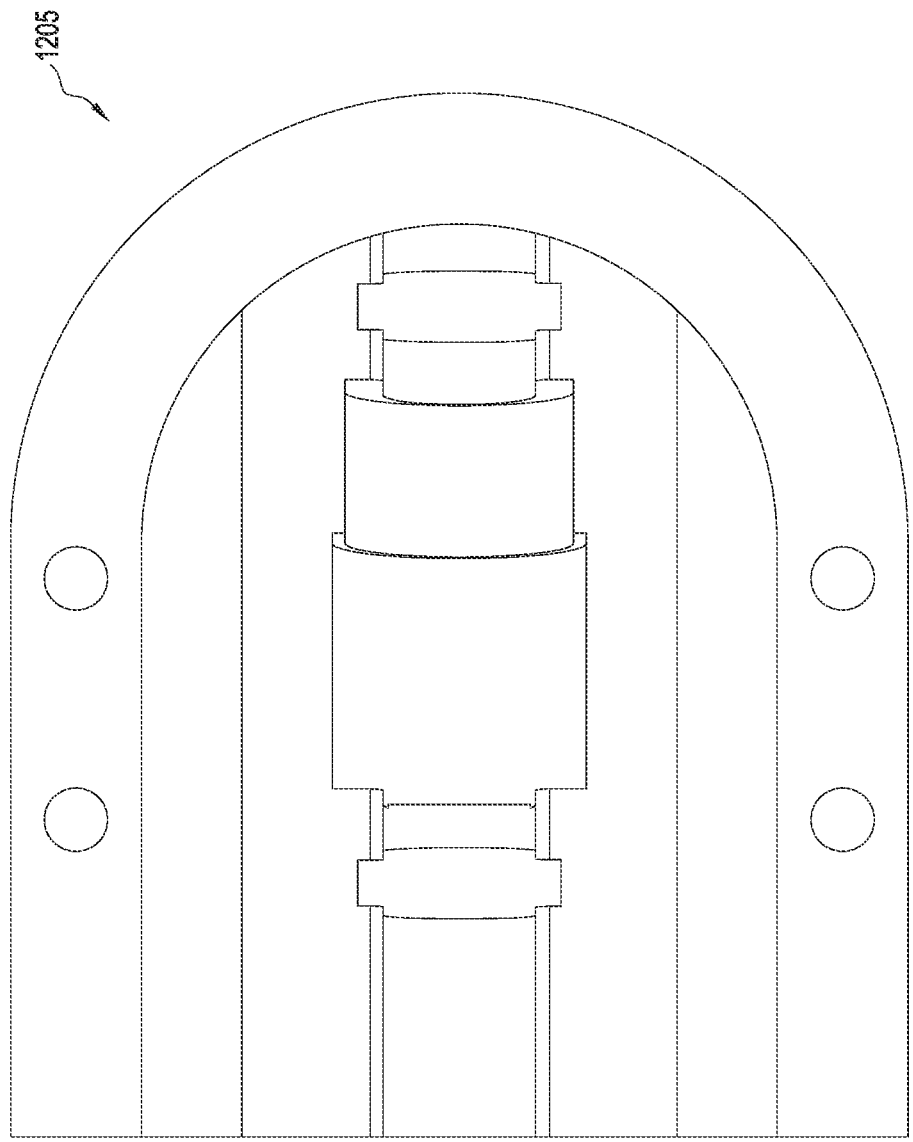
FIG. 14F illustrates a top perspective view of an underside of a catheter lock component of an alternative design of a catheter housing device.

The one or more interior grooves can be sized and shaped differently to secure different types of catheters having different physical dimensions. The one or more interior grooves can secure the catheter or a portion thereof by or with a physical locking, holding, stabilizing without locking, retaining, stabilizing to prevent or reduce the likelihood of movement, stabilizing to minimize movement, or another type of securement. The one or more interior grooves can occupy substantially the same space. For example, the one or more interior grooves can be located in the same portion of the one or more recesses but be sized and shaped differently (see FIG. 14E). The one or more interior grooves can at least partially overlap as well. As illustrated in FIG. 14F, a catheter with different rim or body portions or other portions can be secured by or with the one or more recesses of the catheter lock component 1205 when at least a portion of the catheter secures to the one or more recesses. For example, at least a portion of the catheter can be secured by or with one or more interior grooves located in the one or more recesses. The one or more interior grooves can themselves include one or more sub-grooves. For example, the one or more interior grooves can include one, two, three, four, or five or more sub-grooves. These sub-grooves can be angled differently than each other. For example, the one or more interior grooves can include a first sub-groove that has a surface that is angled in a first direction and a second sub-groove that has a surface that is angled in a second direction, different than the first direction.

The one or more interior grooves can have a wider surface on an upper portion of the one or more interior grooves than on a lower portion of the one or more interior grooves. This can advantageously enable a catheter needle rim to be secured at a final resting angle or inclination angle that approximates the angle at which a needle is inserted into a vein of a patient. As discussed previously this is beneficial because it reduces the chance of injury and/or other complications that can result when the catheter needle and/or catheter moves or is secured at an angle that damages the vein wall or nearby area. Additionally, the one or more interior grooves can have a deeper or shallower recess in at least some portions of the one or more interior grooves. In one alternative design, the one or more recesses can have one interior groove that is deeper recessed (i.e., has a deeper groove) than a different interior groove.

In one alternative design, the one or more recesses of the catheter lock component 1205 can include a first groove sized and shaped to secure a first type of catheter and a second groove sized and shaped to secure a second type of catheter. Additionally, the first type of catheter and the second type of catheter can be different types of catheters having different physical dimensions. Alternatively, the first groove and the second groove can occupy substantially the same space. For example, both the first and second groove can be located in the same portion of the one or more recesses but be sized and shaped differently to secure different types of catheters having different physical dimensions. The first and second groove can be formed in a single recess, or, alternatively, in different recesses. Additionally, the first groove and the second groove can at least partially overlap.

The catheter lock component 1205 can include a back groove 1409. The back groove 1409 can be located near an end of the catheter lock body 1205. For example, the back groove 1409 can be located near the catheter inlet 1407 (see FIG. 14C). The back groove 1409 can be recessed from an interior surface of the right jaw 1413 and/or the left jaw 1421 (see FIG. 14E). The back groove 1409 can permit a rim or portion of a catheter to insert therewithin. Thus, the back groove 1409 of the catheter lock component 1205 can secure a rim or portion of a catheter. The back groove 1409 can have a wider surface on an upper portion of the back groove 1409 than on a lower portion of the back groove 1409. This can advantageously enable a catheter needle rim to be secured at a final resting angle or inclination angle that approximates the angle at which a needle is inserted into a vein of a patient. As discussed previously, this is beneficial because it reduces the chance of injury and/or other complications that can result when the catheter needle and/or catheter moves or is secured at an angle that damages the vein wall or nearby area. For example, the final resting angle or inclination angle can be between 1 and 45 degrees. The inclination angle can also be between 1 and 10 degrees, between 10 and 20 degrees, or between 20 and 30 degrees. The inclination angle can be more than 45 degrees as well, depending on the implementation of the stabilization device. The inclination angle can also be at a very small angle, such as between 0 and 1 degrees. Such configurations can help to limit forces provided to the insertion point. Additionally, the back groove 1409 can have a deeper or shallower recess in at least some portions of the back groove 1409.

The catheter lock component 1205 can include a front groove 1419. The front groove 1419 can be located near an end of the catheter lock body 1205. For example, the front groove 1419 can be located near the catheter outlet 1408 (see FIGS. 14E and 14A). The front groove 1419 can be recessed from an interior surface of the right jaw 1413 and/or the left jaw 1421 (see FIG. 14E). The front groove 1419 can permit a rim or portion of a catheter to insert therewithin. Thus, the front groove 1419 of the catheter lock component 1205 can secure a portion of a rim or portion of a catheter. The front groove 1419 can have a wider surface on an upper portion of the front groove 1419 than on a lower portion of the front groove 1419. This can advantageously enable a catheter needle rim to be secured at a final resting angle or inclination angle that approximates the angle at which a needle is inserted into a vein of a patient. As discussed previously, this is beneficial because it reduces the chance of injury and/or other complications that can result when the catheter needle and/or catheter moves or is secured at an angle that damages the vein wall or nearby area. The inclination angle can be more than 45 degrees as well, depending on the implementation of the stabilization device. The inclination angle can also be at a very small angle, such as between 0 and 1 degrees. Such configurations can help to limit forces provided to the insertion point. The front groove 1419 can have a deeper or shallower recesses in at least some portions of the front groove 1419. Additionally, the front groove 1419 can be deeper recessed (i.e., have a deeper groove) than the back groove 1409, and vice versa.

The catheter lock component 1205 can include a middle groove 1417. The middle groove 1417 can extend along an interior portion of the catheter lock component 1205. For example, the middle groove 1417 can extend from a location proximate to the back groove 1409 to a location proximate to the front groove 1419 (see FIG. 14E). The middle groove 1417 can be longer (i.e., can extend further) than the front groove 1419 and/or the back groove 1409. Alternatively, the middle groove 1417 can be shorter than the front groove 1419 and/or the back groove 1409. Alternatively, the middle groove 1417 can be substantially the same length as the front groove 1419 and/or the back groove 1409. The middle groove 1417 can be recessed from an interior of the right jaw 1413 and/or an interior of the left jaw 1421. The middle groove 1417 can itself comprise more than one groove. These more than one grooves on the middle groove 1417 can be angled differently, or in other words, can have planes that are angled differently with respect to one another (see FIG. 14E). For example, the middle groove 1417 can include one, two, three, four, five, six, seven, eight, nine, ten or eleven or more grooves. Alternatively, the middle groove 1417 can have one or more grooves angled or recessed differently. The middle groove 1417 can be adapted to secure a larger portion of a catheter, and/or a component attached to the catheter, such as a catheter tube connector. The middle groove 1417 can be can be configured to secure a catheter needle rim at a final resting angle or inclination angle that approximates the angle at which a needle is inserted into a vein of a patient. As discussed previously, this is beneficial because it reduces the chance of injury and/or other complications that can result when the catheter needle and/or catheter moves or is secured at an angle that damages the vein wall or nearby area. The inclination angle can be more than 45 degrees as well, depending on the implementation of the stabilization device. The inclination angle can also be at a very small angle, such as between 0 and 1 degrees. Such configurations can help to limit forces provided to the insertion point.

The one or more interior grooves described above can be spaced apart or proximate to one another. For example, there can be one or more gaps between the one or more grooves. The one or more gaps can range in length. The one or more interior grooves, which can be included in the catheter lock component 1205, can provide securement for a variety of types, sizes, and configurations of catheter tubes and devices. The catheter lock component 1205 can include a back groove 1409, a front groove 1419, and a middle groove 1417 that together can secure any type of catheter or portion thereof. For example a catheter can be inserted into and/or secured by, the back groove 1419, the front groove 1409, and/or the middle groove 1417, or a combination of the grooves. FIGS. 14G, 14H, and 14I illustrate how a variety of types of catheters can be inserted into and/or secured by the back groove 1419, the front groove 1409, the middle groove 1417, or a combination thereof.

Figure 14K:
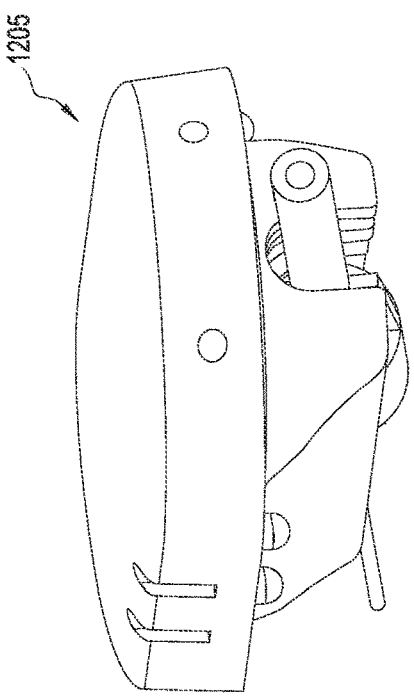
FIG. 14K illustrates a perspective view of a catheter lock component of an alternative design of a catheter housing device wherein a catheter is secured to the catheter lock component and in an angled position.
Figure 14J:
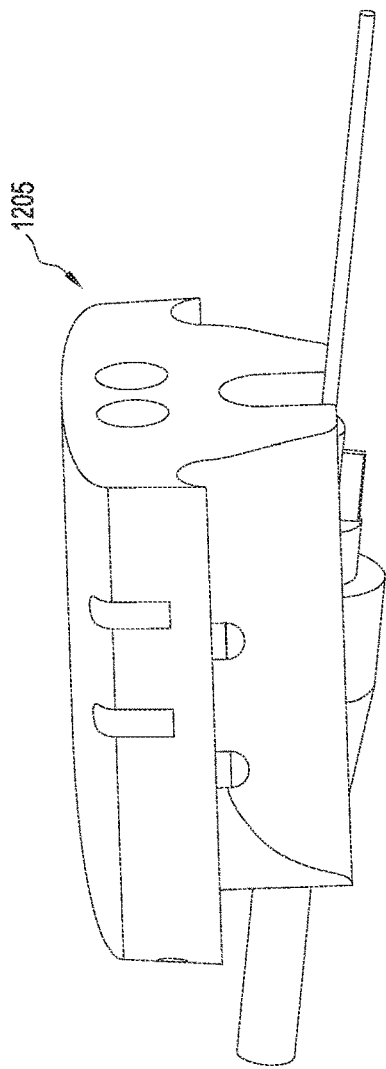
FIG. 14J illustrates a perspective view of a catheter lock component of an alternative design of a catheter housing device wherein a catheter is secured to the catheter lock component and in an angled position.
Figure 14L:
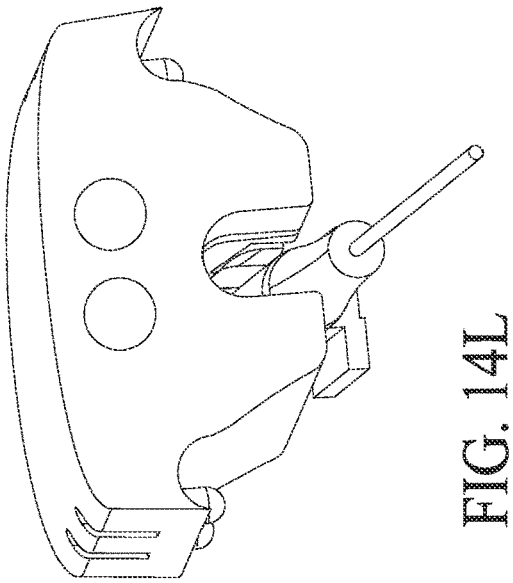
FIG. 14L illustrates a perspective view of a catheter lock component of an alternative design of a catheter housing device wherein a catheter is secured to the catheter lock component and in an angled position.

This provides a tremendous practical benefit for persons who regularly deal with catheters and intravenous devices because the one or more interior grooves of the catheter lock component 1205 can comprise a universal fit. Further, catheters secured by such grooves can be secured at an angle that accommodates a natural inclined position of an intravenous catheter when it is inserted into a patient or when it is in its final resting position after it is inserted into a patient or at a position in between the insertion position and the final resting position. As previously discussed, current techniques for securing a catheter to a patient can result in dislodgment, inappropriate angle of the catheter needle, or twisting or other movement while the needle is inserted into a patient. However, the catheter lock component described in the current disclosure, which can accommodate any type of catheter design, and can secure the catheter and needle in a position that provides for a normal, or optimal, catheter angle. This can help to limit or prevent irritation and/or cannula tip erosion caused by contacting of needle's cannula tip with vein lumen sides. Such configurations can help to limit forces provided to the insertion point. Thus, unlike conventional catheter stabilization methods where securing the catheter typically results in disrupting the natural angle of the needle tip and in the needle tip being awkwardly angled against the wall of the vein and which apply pressure on the catheter's hub in order to secure it to a patient, the securement angle of the catheter in the catheter lock component 1205 and interior grooves therein preserves the integrity of the connection of the needle tip to the vein. FIGS. 14J, 14K, and 14L illustrate various perspective views of a catheter device secured to the catheter lock component 1205 and inclined at a natural angle. Thus, the disclosed catheter lock component 1205 of the catheter stabilizing device 1201 can eliminate a caretaker's need to reapply the catheter securement and reinsert the catheter needle, which can in turn eliminate pain induced to the patient and infection or sickness that can result from reapplication of the catheter device (e.g., phlebitis or other complications).

The catheter lock component can include a lip 1423. The lip 1423 can be substantially flat. Alternatively, the lip 1423 can be sized and shaped to accommodate a portion of the hub component 1207. The lip 1423 can be sized and shaped to accommodate a top surface 1503 of the main body 1501 (see FIGS. 14E and 15C). For example, the lip 1423 can be concave so as to accommodate the top surface 1503 which can be convex. Alternatively, the lip 1423 can be convex so as to accommodate the top surface 1503 which can be concave. When the catheter housing 1201 of FIG. 12B is assembled, the catheter lock component 1205 can be placed upon the hub component 1207 such that the lip 1423 of the catheter lock component 1205 can rest upon the top surface 1503 of the hub component 1207. Additionally, the catheter lock component 1205 can be placed upon the hub component 1207 such that the lip 1423 of the catheter lock component 1205 can rest upon the top surface 1503 of the hub component 1207 when the one or more pins 1405 secure to the one or more recesses 1515 in the hub component 1207.

The engagement between the catheter lock component 1205 and the hub component 1207 can advantageously inhibit and/or prevent movement of the lock component 1205 relative to the hub component 1207. The catheter lock component 1205 can inhibit or prevent the catheter from moving once the catheter lock component 1205 is secured with the hub component 1207. The engagement between the catheter lock component 1205 and the hub component 1207 can advantageously form a hermetic seal around the catheter. Thus, the catheter lock component 1205 (e.g., in combination with the cover 1203) can form a seal around the catheter and/or the insertion site.

The back face 1410 of the catheter lock component 1205 can include one or more lights. The one or more lights can help illuminate interior portions of the catheter housing 1201 in and around the insertion site. The one or more lights can allow the catheter to be inspected during the day and/or night.

The back face 1410 of the catheter lock component 1205 can include one or more sensors (not shown). For example, the back face 1410 can include one, two, three, four, five, six, or seven or more sensors. The back face 1410 can incorporate various sensors to measure physiological parameters or condition of the patient. For example, the sensors can include a temperature sensor to measure a temperature of the measurement site of a patient. The sensors can also include a pulse rate sensor, a blood oximeter sensor, phlebomanometer or artery blood manometer sensor, puncture site hygrometer, blood glucose sensor or any other noninvasive physiological vital signs sensors.

The back face 1410 of the catheter lock component 1205 can include can include one or more bio-sensors (not shown). For example, the back face 1410 can include one, two, three, four, five, six, or seven or more bio-sensors. The bio-sensors can include a micro-processor. For example, the bio-sensors can include an LCD monitor for detecting, measuring, storing and/or displaying patient vital functions, including venous and arterial blood pressure, heartbeat, blood oxygen level (blood oxygen saturation), general and topical temperature, and local tissue or skin humidity, and/or venous blood current speed, among others. The measurements and/or calculations performed and/or taken by the one or more bio-sensors can be stored on a flash storage memory positioned on one or more of the cover 1203, catheter lock component 1205, the hub component 1207, or the one or more the full-length fastening straps 1211 or one or more partial-length fastening straps 1215. Alternatively, the sensor measurements can be wirelessly transmitted to a patient monitoring system for display to a care provider or user. Alternatively, the sensor measurements can be transmitted via a direct or wired transmission.

Hub Component

Figure 15C:
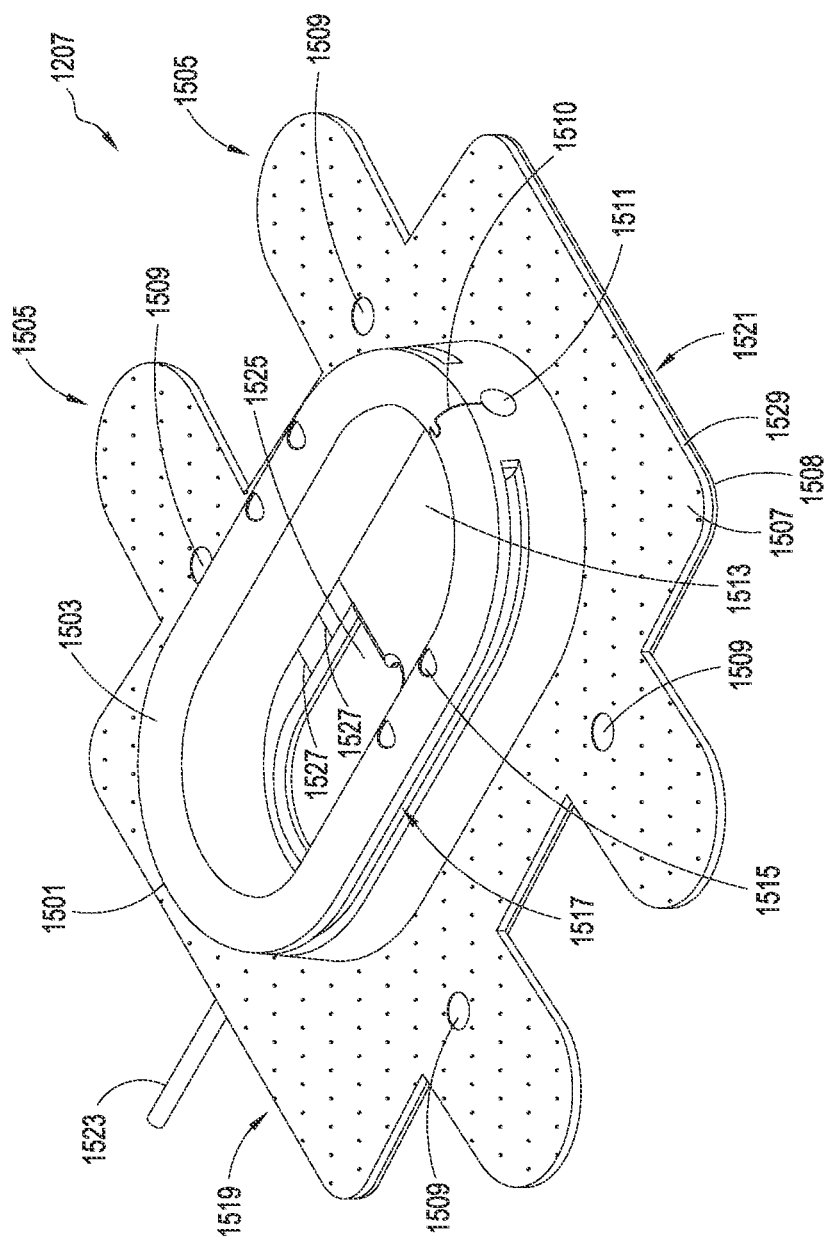
FIG. 15C illustrates a perspective view of a hub component of an alternative design of a catheter housing device.

FIGS. 15A through 15C illustrate different views of the hub component 1207. As shown in FIG. 15A, the hub component 1207 can include a main body 1501, a membrane 1504, and a gas line 1523. In one alternative design, the catheter lock component 1205 and the hub component 1207 can be integrally formed or comprise a unitary structure. A caregiver can attach, adhere, secure, and/or write patient information on the hub component 1207 or a portion thereof. Such patient information can include the insertion date and/or time, the patient's identification, and other information.

The main body 1501 can comprise plastic, rubber, and/or silicone, among other materials. The main body 1501 can comprise a transparent material. Alternatively, the main body 1501 can be made of a nontransparent material. Additionally, the main body 1501 can be comprise both transparent and nontransparent material. For example, portions of the main body 1501 can be made of transparent material where it is advantageous to be able to see through a portion of the main body 1501 in order to observe other components of the catheter housing 1201. The main body 1501 can be made of substantially shockproof and/or durable material. This is advantageous because the catheter housing 1201 and/or the main body 1501 can be subjected to impact during implementation of the device onto, for example, patients in a hospital. The main body 1501 can comprise substantially waterproof material. This is advantageous because the catheter housing 1201 and the main body 1501 can be subjected to water or other liquids when the device is in use. The main body 1501 can include a top surface 1503. As previously discussed, the top surface 1503 can be concave or convex. Additionally, the top surface 1503 can be substantially flat. In one alternative design, the top surface 1503 can be smooth and/or rounded.

As illustrated in FIGS. 15B and 15C, the hub component 1207 can contain an opening 1525 in the membrane 1504. This opening 1525 can be positioned over a site where a catheter needle is to be inserted into a patient. The opening 1525 can be sized and shaped to fit within the main body 1501 (see FIG. 15C). For example, the opening 1525 can be generally egg-shaped, trapezoidal, rectangular, square, oval, and/or circular in shape, among other shapes. Additionally, the opening 1525 can be a combination of these described shapes. For example, as shown in FIGS. 15B and 15C, the opening 1525 can have a rounded end and a substantially straight end. Additionally, the opening 1525 can be bell-shaped, or can contain a rounded end and a substantially straight end with a round recess in the substantially straight end (see, e.g., FIG. 15E) so as to accommodate a cylindrical catheter or needle to advantageously to lay.

As also illustrated in FIGS. 15B and 15C, the membrane 1504 can extend around the opening 1525 in a region defined within the main body 1501 and surrounding an insertion site. Such configurations can confine the insertion site to within the boundaries of the main body 1501 and can thus advantageously reduce and/or elimination ingress of pathogens to the insertion site. The membrane 1504 can include a thin silicone membrane. The membrane 1504 can overlap and/or surround the needle and/or the insertion site. This can advantageously help to ensure that the hub component 1207 is secured and/or sealed to a patient's skin. For example, the membrane 1504 can overlap at least a portion of the insertion site and/or needle to provide a hermetic sealing isolation state between the hub component 1207 and the patient's skin. Accordingly, the membrane 1504 can help to inhibit or prevent air and/or gases from an outside environment from entering the insertion site. Such configurations can also inhibit or prevent lower edges of a catheter device or portion thereof from contacting skin underneath. This can help to inhibit or prevent skin abrasions, ulcers, and/or irritation caused by contact between the catheter device or portion thereof and the patient's skin.

The hub component 1207 can include one or more markers or indicators 1527 located on a portion of the main body 1501 and/or the membrane 1504, near the opening 1525. For example, the hub component 1207 can include one, two, three, four, five, six, or seven or more markers or indicators 1527. In one alternative design, the hub component 1207 has four markers 1527, two of which are disposed proximate to a first side of the opening 1525 and two of which are disposed proximate to a second side of the opening 1525. The one or more markers 1527 can help a caregiver position and align the hub component 1207 over an insertion site where the catheter and/or needle has been already inserted. Alternatively, the one or more markers 1527 can help provide an indication as to where a needle should be inserted into a patient. This can greatly aid caretakers in determining where the optimal insertion location should be so as to comport with the position of a catheter device when it is engaged and secured by the catheter lock component 1205. The one or more markers 1527 can be located on a portion of the main body 1501 and/or the membrane 1504 proximate to the opening 1525 (see FIG. 15C). In one alternative design, the one or more markers 1527 can be located on a portion of the membrane 1504 near a side of the main body 1501 (see FIG. 15C). The one or more markers 1527 can comprise a line, dot, or other indicator.

As illustrated in FIG. 15C, the membrane 1504 of the hub component 1207 can include an inner membrane portion 1513. The inner membrane portion 1513 can be proximate to the opening 1525 and can be contained within the boundaries of the main body 1501. The inner membrane portion 1513 can provide a platform for the catheter or portion thereof to rest or lay on when the catheter and/or needle is inserted into the patient. For example, in one alternative design, the catheter or portion thereof is inserted into the patient and is resting on the inner membrane portion 1513, the catheter lock component 1205 can be placed over the catheter or portion thereof that rests on the inner membrane portion 1513 and can secure the catheter or portion thereof to prevent movement of the catheter or portion thereof.

As shown in FIGS. 15A through 15C, the main body 1501 can comprise a rounded shape. For example, the main body 1501 can be generally egg-shaped. Alternatively, the main body 1501 can be approximately trapezoidal, rectangular, square, oval, and/or circular in shape, among other shapes.

As shown in FIGS. 15B, 15C, 15K, 15L, and 15M (and as discussed previously), the main body 1501 can include one or more recesses 1515. For example, the main body 1501 can include one, two, three, four, five, six, or seven or more recesses 1515. The one or more recesses 1515 can accommodate the one or more pins 1405 on the catheter lock component 1205 (see FIGS. 14C and 14E). The main body 1501 can include one or more peripheral grooves 1517. For example, the main body main body 1501 can include one, two, three, four, five, six, or seven or more peripheral grooves 1517. As discussed previously, the one or more peripheral grooves 1517 can be configured to accommodate a protrusion 1315 on the cover 1203. The one or more peripheral grooves 1517 of the main body 1501 can be continuous around the perimeter of the main body 1501. Alternatively, the one or more peripheral grooves 1517 can be noncontinuous. For example, as shown in FIG. 15C, the one or more peripheral grooves 1517 can extend along a portion of the perimeter of the main body 1501, but not extend continuously around the entire perimeter of the main body 1501. For example, the one or more peripheral grooves 1517 can extend along a perimeter of the main body 1501 proximate to the hub inlet 1511, but terminate at a location before reaching the hub inlet 1511. In one alternative design, the main body 1501 includes more than one peripheral groove 1517 that extend along the perimeter of the main body 1501, which secure to one or more protrusions 1315 on the cover 1203. As discussed previously, the one or more protrusions 1315 can secure to the one or more peripheral grooves 1517 by a snap-fit, press fit, and/or other configuration for securely connecting the cover 1203 to the hub component 1207.

As illustrated in FIG. 15C, the main body 1501 can include one or more joints 1510 that can be pulled apart or pushed together, to allow for a needle, fluid tube, or catheter device or portion thereof to more easily pass through the hub inlet 1511. For example, the main body 1501 can include one, two, three, four, five, six, or seven or more joints 1510. In one alternative design, the main body 1501 includes one joint 1510. The joint 1510 can be proximate to the hub inlet 1511. Thus, the joint 1510 can provide a mechanism whereby a needle, fluid tube, or catheter device or portion thereof can be accommodated by the main body 1501 so as to be able to pass into and through the main body 1501 with relative ease and in a short timeframe. The joint 1510 can be configured to hermetically close the main body 1501, and can form a seal in the main body 1501 and the hub component 1207. The joint 1510 can permit the main body 1501 to be spaced apart, pulled apart, pushed apart, and/or otherwise partially separated. Alternatively, the joint 1510 can extend down an entire side portion of the hub main body 1501 so that the joint 1510 separates an entire cross-section of the side portion of the hub main body 1501. Alternatively, the joint 1510 can separate at least in part by flexing the main body 1501.

The membrane 1504 of the hub component 1207 can be sized and shaped to accommodate a patient's arm, leg, appendage, or other portion of a patient's body. The membrane 1504 can be rectangular in shape. Alternatively, the membrane 1504 can be egg-shaped, trapezoidal, square, oval, and/or circular in shape, among other shapes. Additionally, the membrane 1504 can comprise a combination of these described shapes. As illustrated in FIG. 15C, the membrane 1504 can have a front side 1519 and a back side 1521, wherein the front side 1519 is wider than the back side 1521. Alternatively, the membrane 1504 can have a front side 1519 that is substantially equal in width to, or of less width than, the back side 1521.

The membrane 1504 can be integrally formed with the main body 1501. For example, the membrane 1504 can be molded with the main body 1501. The main body 1501 can be pressed onto, adhered to, and/or otherwise attached to a portion of the membrane 1504, which can include a top layer 1507 of membrane 1504. The membrane 1504 can include a recessed portion to accommodate the main body 1501. For example, as illustrated in FIG. 15N, the membrane 1504 can contain a recessed portion that surrounds the opening 1525 and allows a portion of the main body 1501 to sit within or be accommodated by the recessed portion of the membrane 1504. Additionally, the membrane 1504 can contain a recessed portion to accommodate other portions of the catheter housing 1201, such as the cover 1203 or a portion of the cover 1203. The membrane 1504 can include one or more different materials. Additionally, the membrane 1504 can include substantially the same material. The main body 1501 and the membrane 1504 can include the same material. Alternatively, the main body 1501 and the membrane 1504 can include different materials. The membrane 1504 can comprise silicone, plastic, and/or rubber, among other materials. The membrane 1504 can comprise, at least in part, FDA approved materials.

The membrane 1504 can extend outwardly from a base of the main body 1501 (see FIG. 15C). For example, the membrane 1504 can be coupled with an outer edge of the base of the main body 1501. A bottom surface of the base of the main body 1501 can be coupled with the membrane 1504. For example, at least a portion of the membrane 1504 can extend inwardly towards an inner region of the main body 1501 (see, e.g., FIGS. 15B and 15C). The membrane 1504 can surround at least a portion of a perimeter of the main body 1501. Thus, the membrane 1504 can surround all or a portion of a perimeter of an inner edge and/or an outer edge of the base of the main body 1501.

Figure 15D:
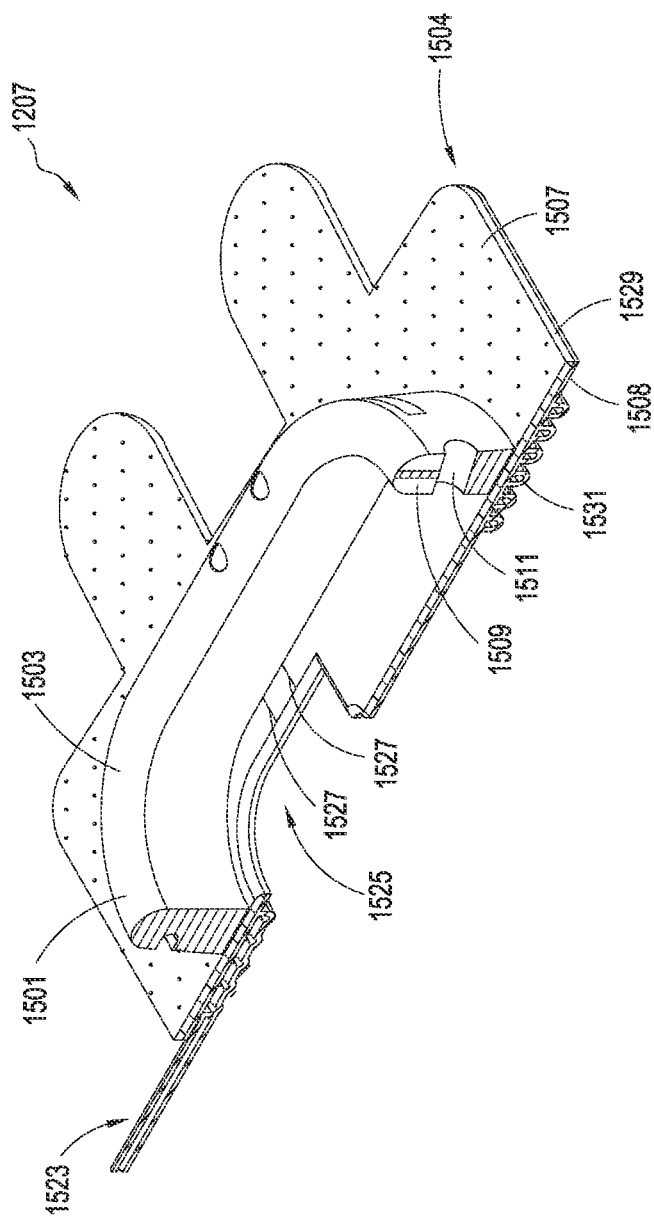
FIG. 15D illustrates a cross-section perspective view of a hub component of an alternative design of a catheter housing device.

As illustrated in the cross-section perspective view of the hub component 1207 of FIG. 15D, the membrane 1504 can have one or more layers. For example, the membrane 1504 can have one, two, three, four, five, six, or seven or more layers. In one alternative design, the membrane can have a top layer 1507, a middle layer 1529, and a bottom layer 1508. At least a portion of the top layer 1507 can include a plurality of hook and loop structures, buckles, fungi-like attachment, and/or other attachment structures or methods. In one alternative design, at least a portion of the top layer 1507 can include Velcro. The top layer 1507 can facilitate connection of the one or more full-length fastening straps 1211 and/or partial-length fastening straps 1215. In one alternative design, the full-length fastening straps 1211 and/or partial length fastening straps 1215 can wrap around a patient's arm, leg, other or body part and secure to at least a portion of the top layer 1507 such that the hub component 1207 is secured to the patient. The top layer 1507 can be a varied thickness. For example, the bottom layer can be between 0 and 10 mm in thickness. Alternatively, the top layer 1507 can be between 10 and 20 mm in thickness. The top layer 1507 can be other thicknesses as well.

As shown in FIG. 15C, in one alternative design, the membrane 1504 can include one or more arms 1505, which can extend outwardly from a portion of the membrane 1504. For example, the membrane 1504 can have one, two, three, four, five, six, seven, or eight or more arms 1505. The one or more arms 1505 can be sized and shaped to accommodate and secure to one or more of the partial-length fastening straps 1215. Alternatively, the one or more full-length fastening straps 1211 can be configured to secure to the one or more arms 1505. Including one or more arms 1505 to the membrane 1504 provides a practical method by which the one or more partial-length fastening straps 1215 can be secured to the membrane 1504 without requiring the membrane 1504 to extend far beyond the exterior perimeter of the main body 1501. Thus, the amount of material used in the membrane 1504 can be optimized and/or minimized.

The middle layer 1529 of the membrane 1504 can be in between the top layer 1507 and the bottom layer 1508. The middle layer 1529 can be integrally formed with, or molded to, the top layer 1507 and/or the bottom layer 1508. Alternatively, the middle layer 1529 can be pressed onto, adhered to, and/or otherwise attached to the top layer 1507 and/or the bottom layer 1508. The middle layer 1529 can be thicker than the top layer 1507 and/or the bottom layer 1508. The middle layer 1529 can include a stronger and/or stiffer material than the top layer 1507 and/or the bottom layer 1508. For example, the middle layer 1529 can serve to structurally reinforce the membrane 1504. The middle layer 1529 can comprise silicone, plastic, and/or rubber, among other materials. Additionally, the middle layer 1529 can comprise a combination of materials. In one alternative design, the middle layer 1529 is approximately 1 mm thick or less, for example, 0.5 mm in thickness In some alternative designs, the middle layer 1529 is between 1 mm and 10 mm in thickness. In some alternative designs, the middle layer 1529 is between 10 mm and 20 mm in thickness.

The bottom layer 1508 of the membrane 1504 can at least partially contact the skin of a patient when the hub component 1207 and/or the catheter housing 1201 is attached to the patient. The bottom layer 1508 can include different structures, shapes, and functions. The bottom layer 1508 can comprise silicone, plastic, and/or rubber, among other materials. Additionally, the bottom layer 1508 can comprise a combination of materials. The bottom layer 1508 can be a varied thickness. For example, the bottom layer can be between 0 and 10 mm in thickness. Alternatively, the bottom layer 1508 can be between 10 and 20 mm in thickness. The bottom layer 1508 can be other thicknesses as well.

Figure 15E:
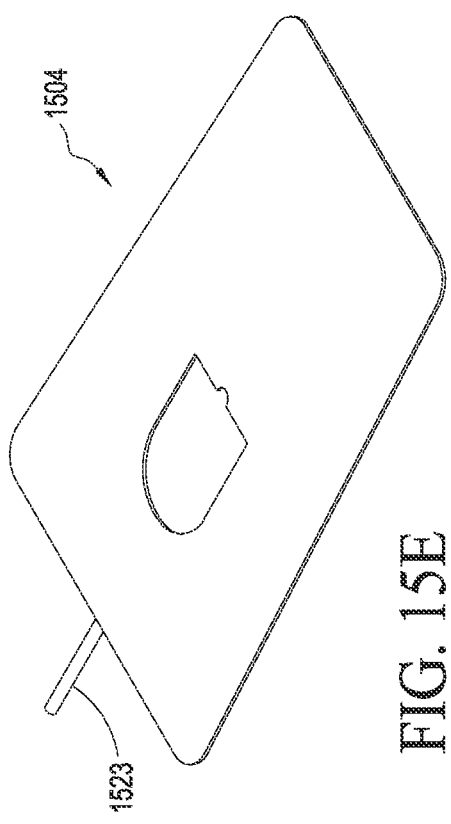
FIG. 15E illustrates a perspective view of a top portion of a membrane of a hub component of an alternative design of a catheter housing device.
Figure 15G:
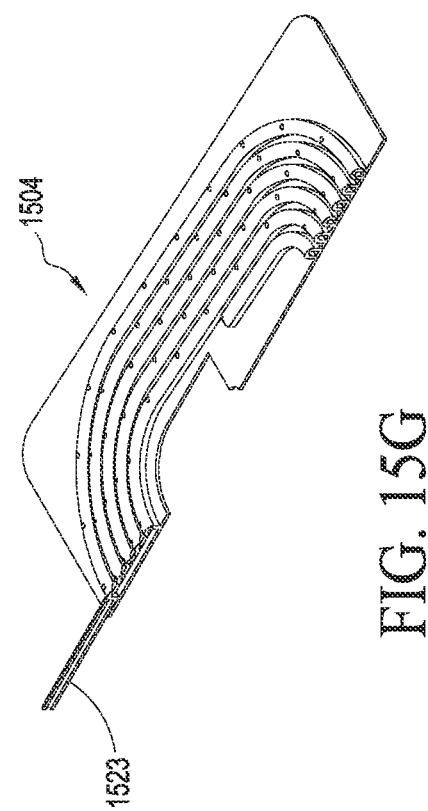
FIG. 15G illustrates a cross-section perspective view of a bottom portion of a membrane of a hub component of an alternative design of a catheter housing device where the membrane comprises perforated loop tubes.
Figure 15F:
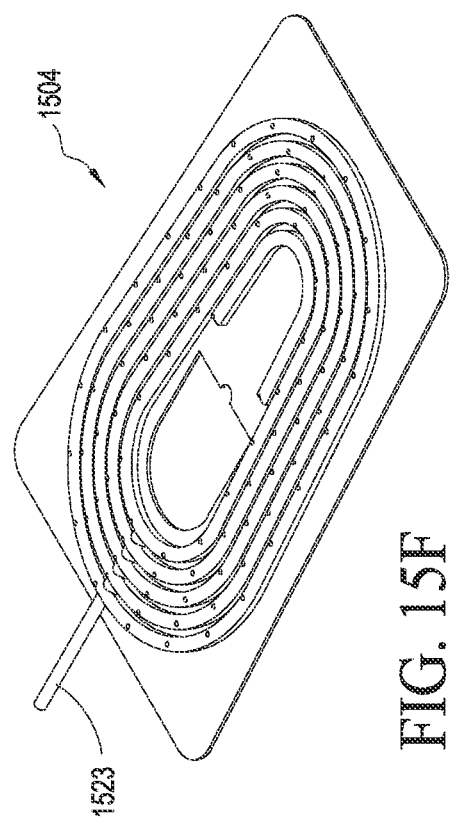
FIG. 15F illustrates a perspective view of a bottom portion of a membrane of a hub component of an alternative design of a catheter housing device where the membrane comprises perforated loop tubes.

In one alternative, as shown in FIGS. 15E through 15G, the bottom layer 1508 can include one or more perforated loop tubes. For example, the bottom layer 1508 can include one, two, three, four, five, six, seven, eight, nine, or ten or more perforated loop tubes. The perforated loop tubes of the bottom layer 1508 can be substantially cylindrical, circular, square, or rectangular, among other shapes. The perforate loop tubes can also comprise a combination of these shapes. The perforated loop tubes can be sized, shaped, and spaced apart to accommodate ventilation or for other reasons. For example, the perforated loop tubes can provide spacing to allow air to flow between the perforated loop tubes and a patient's skin. Thus, even if the hub component 1207 and/or the catheter housing 1201 is secured to a patient, the patient can still benefit from ventilation to the region in and around the insertion site and attachment location of the hub component 1207 because of such perforated look tubes. The perforated loop tubes can be arranged adjacent to one another so that they at least partially surround the opening 1525 in the membrane 1504 (see FIG. 15F). The perforated loop tubes can be continuous or noncontinuous. Alternatively, the perforated loop tubes can be noncontinuous—i.e., can terminate at two ends (see FIG. 15F).

The one or more perforated loop tubes of the bottom layer 1508 can alternatively be connected to the gas line 1523 of the hub component 1207. The gas line 1523 can be used to insert inert gas that is free from oxygen to inhibit microbe development. This inert gas can contain sterilizing and/or soothing properties. This inert gas can be supplied from an ampoule attached to the gas line 1523. The gas line 1523 can be connected to the one or more perforated loop tubes such that, when gas flows from the ampoule through the gas line 1523, the gas travels through the perforated loop tubes. The perforated loop tubes can contain holes that allow the gas flowing from the gas line 1523 to exit through the holes and contact the patient's skin. The gas can be provided through the gas line 1523 and to the holes so that a gas cushion is formed when the gas flows through the holes and contacts the patient's skin. The gas can further be configured to be applied, or flow, continuously or on an intermittent basis. The supply of gas in this manner can substantially increase patient comfort in an around the insertion site and location where the hub component 1207 and/or membrane 1504 is attached. For example, the application of such gas can have a soothing effect, or can prevent numbing or itching from prolonged attachment times. The application of such gas can also prevent contamination of the site.

Figure 15H:
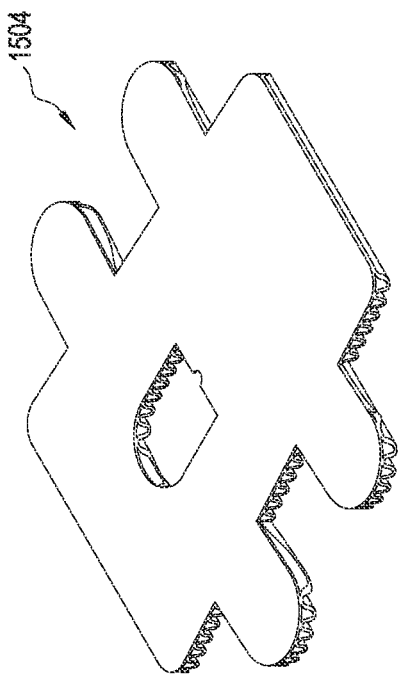
FIG. 15H illustrates a perspective view of a top portion of a membrane of a hub component of an alternative design of a catheter housing device.
Figure 15J:
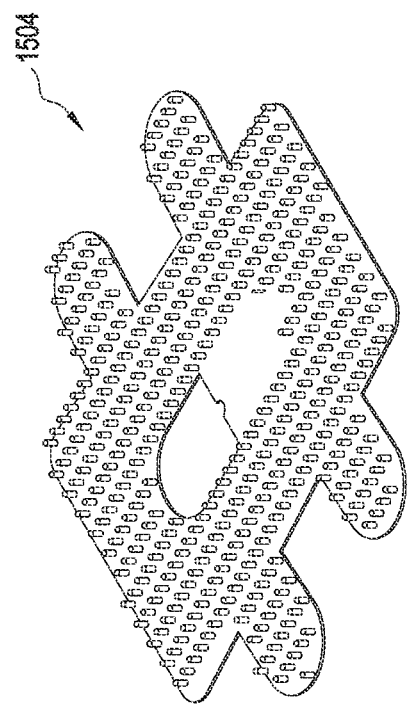
FIG. 15J illustrates a perspective view of a bottom portion of a membrane of a hub component of an alternative design of a catheter housing device where the membrane comprises suction cups.
Figure 15I:
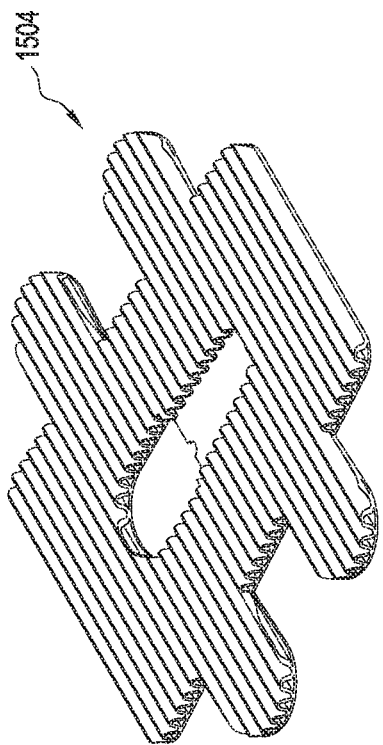
FIG. 15I illustrates a perspective view of a bottom portion of a membrane of a hub component of an alternative design of a catheter housing device where the membrane comprises a corrugated structure.
Figure 15L:
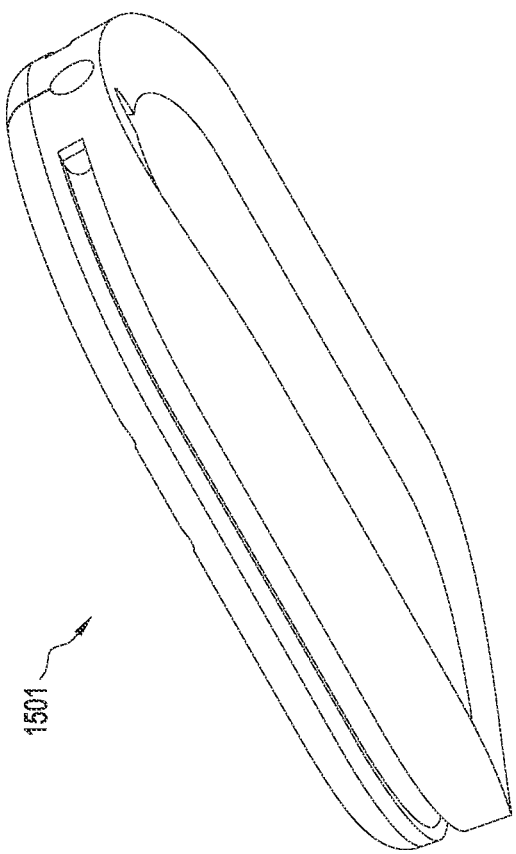
FIG. 15L illustrates a perspective view of a main body of a hub component of an alternative design of a catheter housing device.
Figure 15K:
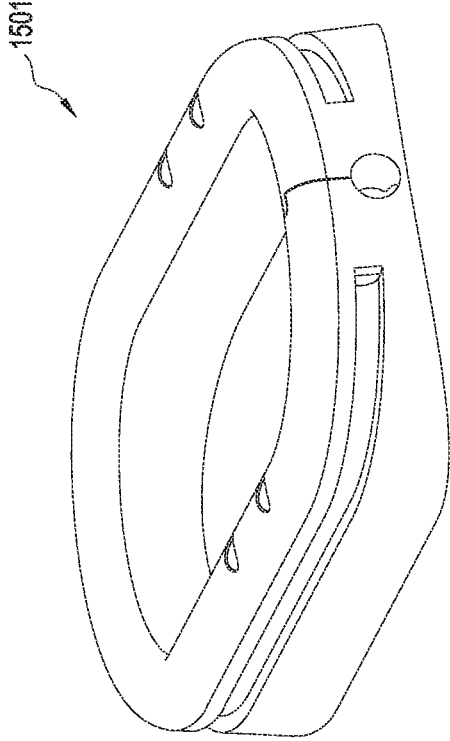
FIG. 15K illustrates a perspective view of a main body of a hub component of an alternative design of a catheter housing device.
Figure 15M:
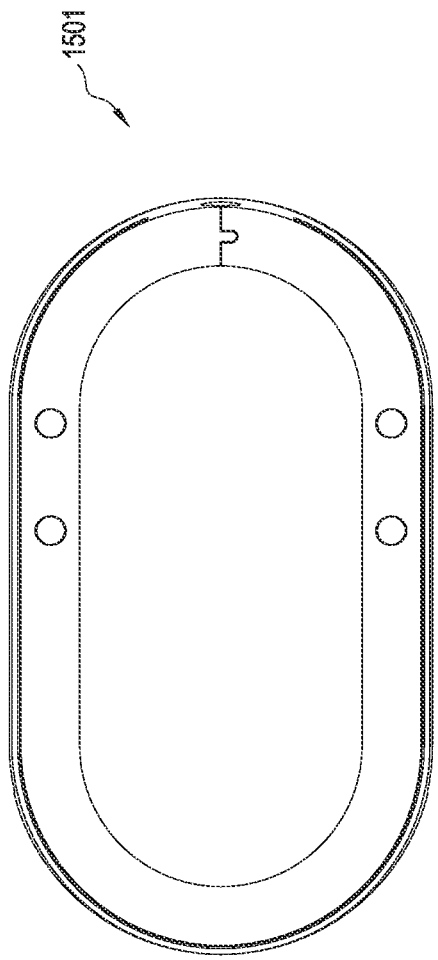
FIG. 15M illustrates a top perspective view of a main body of a hub component of an alternative design of a catheter housing device.
Figure 15N:
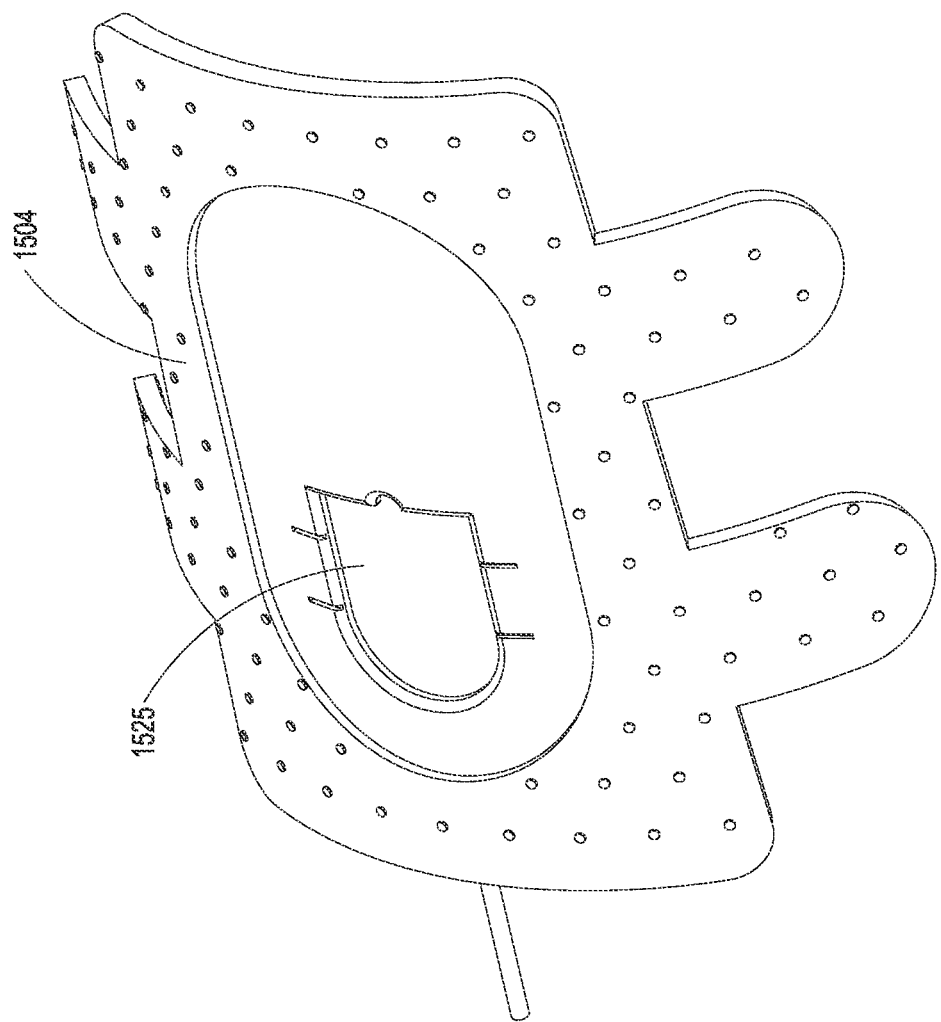
FIG. 15N illustrates a recessed portion of a membrane of a hub component of an alternative design of a catheter housing device.

In another alternative, as shown in FIGS. 15H and 15I, the bottom layer 1508 can comprise a corrugated structure. The corrugated structure can be substantially cylindrical, circular, square, or rectangular, among other shapes. The corrugated structure can also comprise a combination of these shapes. The corrugated structure can be sized, shaped, and spaced apart to accommodate ventilation or for other reasons. The corrugated structure can provide gaps to allow air to flow between the corrugated structure and contact the patient's skin. Thus, even if the hub component 1207 and/or the catheter housing 1201 is secured to a patient, the patient can still benefit from ventilation to the region/section of the bottom layer 1508 that contacts the skin of the patient. The corrugated structure can be one continuous piece, or alternatively, can comprise more than one piece.

As shown in FIG. 15J, the bottom layer 1508 can include one or more suction cups. For example, the bottom layer 1508 can have one or more, two or more, three or more, four or more, five or more, six or more, seven or more, eight or more, nine or more, ten or more, or eleven or more. For example, the bottom layer 1508 can have between twenty and fifty suction cups. Alternatively, the bottom layer 1508 can have between 50 and a hundred suctions cups. The one or more suction cups can be positioned in one or more rows. The suction cups can be configured to stabilize a connection between the hub component 1207 and the patient's skin. The hub component 1207 and/or the membrane 1504 can be manually pressed onto the patient's skin to secure the hub component 1207 to the patient. The suction cups can engage with the patient's skin such that the hub component 1207 can be at least partially secured to the patient without requiring the fastening straps to be connected to the hub component 1207 and/or wrapped around a portion of the patient's body.

The one or more suction cups can be substantially cylindrical, circular, square, or rectangular, among other shapes. The suction cups can also comprise a combination of these shapes. The suction cups can be sized, shaped, and spaced apart to accommodate ventilation or for other reasons. The suction cups can be spaced to provide gaps to allow air to flow between the suction cups and the patient's skin. Thus, even if the hub component 1207 and/or the catheter housing 1201 is secured to a patient, the patient can still benefit from ventilation to the region/section of the bottom layer 1508 that contacts the skin of the patient.

At least a portion of the membrane 1504 can be used for fixing various peripheral tools, such as a catheter tube, an LCD monitor of a micro-processor, and/or a metallic ampule of the soothing and sterilizing gas. Such peripheral tools can be fixed or secured to at least a portion of the membrane 1504 through hook and loop structures, buckles, fungi-like attachment, and/or other attachment structures or methods.

Sensors on Catheter Housing Device

As shown in FIG. 15C, the hub component 1207 can include one or more sensors 1509. Additionally, the one or more sensors 1509 can be located on various components of the catheter housing 1201. For example, as discussed previously in part, the one or more sensors 1509 can be located and/or mounted on the cover 1203, the catheter lock component 1205, the one or more full-length fastening straps 1211, and/or the one or more partial-length fastening straps 1215. Additionally, the number of sensors 1509 located on and/or mounted to the various components described above can be one, two, three, four, five, six, seven, eight, nine, ten, eleven, twelve, or thirteen or more.

The one or more sensors 1509 can be used to measure various physiological parameters or condition of a patient. The one or more sensors 1509 can include a temperature sensor (for example, a topical temperature sensor), a blood pressure sensor, a blood oxygen saturation sensor, a sensor for liquid and blood leakage, and/or a skin humidity sensor. The sensors 1509 can be located in various locations on the membrane 1504. For example, the sensors 1509 can be located near the front side 1519 and/or the back side 1521 of the membrane 1504. Additionally, the sensors 1509 can be located in regions proximate to the arms 1505 of the membrane 1504 (see FIG. 15C).

The one or more sensors can include one or more bio-sensors. The bio-sensors can include a micro-processor. For example, the bio-sensors can include an LCD monitor for detecting, measuring, storing and/or displaying patient vital functions, including venous and arterial blood pressure, heart beats, blood oxygen levels, general and topical temperature, and local tissue humidity, and/or venous blood current speed, among others. The measurements and/or calculations performed and/or taken by the one or more sensors 1509, can be stored on a flash storage memory positioned on one or more of the cover 1203, the catheter lock component 1205, the hub component 1207, the full-length fastening strap 1211, the partial-length fastening strap 1215, and/or the membrane 1504. Any of the sensor measurements discussed herein can be wirelessly transmitted to a patient monitoring system for analysis, management, organization, and/or display to a care provider or user. Alternatively, the sensor measurements can be transmitted to a personal communications device, such as a tablet or smart device, or a software application or website.

Example Method

The catheter stabilizing device 1201 described herein can be assembled and/or secured to a patient during a catheter insertion procedure in a number of different ways. For example, in one alternative, after the caregiver identifies the insertion site and inserts the needle and catheter into a patient, the catheter or portion thereof can be placed within a portion of the catheter housing device 1201, such as the hub component 1207. Then, the hub component 1207 can be centered over the insertion site. The indicators or markers 1527 of the hub component 1207 can help with the positioning of the hub component 1207 on the patient around the insertion site. Next, a fluid tube can be inserted through a portion of the hub component, for example, the hub inlet 1511 of the main body 1501 of the hub component 1207 and connected to a portion of the catheter (such as a body of the catheter). Next, at least a portion of the hub component 1207 can be secured to the patient with one or more fastening straps. For example, a full-length fastening strap 1211 can secure to a portion of the patient's body and also secure to a front side 1519 of the membrane 1504 of the hub component 1207. Additionally, another full-length fastening strap 1211 can secure to a portion of the patient's body and also secure to a back side 1521 of the membrane 1504 of the hub component 1207. To further secure the hub component 1207, one or more partial length fastening straps 1221 can secure to a portion of the patient's body and also to a portion of the hub component 1207, such as an arm 1505 of the hub component 1207. After the hub component 1207 has been secured to the patient and the catheter is resting on a portion of the hub component 1207, such as the inner membrane portion 1513 of the membrane 1504 of the hub component 1207, the catheter or portion thereof can be secured with the catheter lock component 1205. The catheter lock component 1205 can secure a catheter or a portion thereof by or with a physical locking, holding, stabilizing without locking, retaining, stabilizing to prevent movement, stabilizing to minimize or reduce the likelihood of movement, or another type of securement. The catheter lock component 1205 can also be secured to at least a portion of the hub component 1207, for example, a main body 1501 of the hub component 1207. Next, a cover 1203 can be placed over the catheter lock component 1205 and/or a portion of the hub component 1207 to seal the insertion site from the outside environment and protect it from contamination. The cover 1203 can secure to the catheter lock component 1205 and/or a portion of the hub component 1207. In some alternatives, the method further includes connecting a gas tube to an at least one port of the catheter housing device 1201 and permitting sterilizing and/or anesthetic gas to flow to the insertion site.

In some alternatives, the method of assembling and/or securing a catheter stabilizing device 1201 to a patient during a catheter insertion procedure can begin by first identifying an insertion site, and then securing at least a portion of the catheter housing device 1201, such as the hub component 1207, to the patient around the insertion site. The opening 1525 of the hub component 1207 can be positioned so that the insertion site is at least partially aligned with indicators 1527 on the hub component 1207 and the insertion site is located within the opening 1525 of the hub component 1207. The securing of at least a portion of the catheter housing device 1201, such as the hub component 1207, to the patient around the insertion site can include use of one or more fastening straps, for example, in the manner described in the method previously described. Once the insertion site has been identified and the hub component 1207 secured to the patient, the catheter and needle can then be inserted into the patient at the insertion site and the catheter can then be laid atop a portion of the hub component 1207, for example, the inner membrane portion 1513 of the membrane 1504 of the hub component 1207. Next, a fluid tube can be inserted through a portion of the catheter housing device 1201, such as the hub component 1207 and for example, the hub inlet 1511 of the main body 1501 of the hub component 1207, and connected to a portion of the catheter (such as a body or rim of the catheter). After the catheter housing device 1201 or a portion thereof such as the hub component 1207 has been secured to the patient and the catheter is resting on a portion of the hub component 1207, such as the inner membrane portion 1513 of the membrane 1504 of the hub component 1207, the catheter or portion thereof can be secured with the catheter lock component 1205. The catheter lock component 1205 can secure a catheter or a portion thereof by or with a physical locking, holding, stabilizing without locking, retaining, stabilizing to prevent movement, stabilizing to minimize or reduce the likelihood of movement, or another type of securement. The catheter lock component 1205 can also secure to at least a portion of the hub component 1207, for example, a main body 1501 of the hub component 1207. Next, a cover 1203 can be placed over the catheter lock component 1205 and/or a portion of the hub component 1207 to seal the insertion site from the outside environment and protect it from contamination. The cover 1203 can secure to the catheter lock component 1205 and/or a portion of the hub component 1207. In some alternatives, the method further includes connecting a gas tube to an at least one port of the catheter housing device 1201 and permitting sterilizing and/or anesthetic gas to flow to the insertion site.

As discussed previously, the catheter housing (also referred to as "catheter housing device") 1201 and/or the various components discussed herein can comprise a single unit or structure. Thus, the method of securing the catheter housing device 1201 to a patient during a catheter insertion procedure can comprise placing a single unit catheter housing device 1201 over an insertion site after the caregiver has identified the insertion site and inserted the needle and/or catheter into a patient. Once the single unit catheter housing device 1201 is secured to the patient over the insertion site and the catheter or portion thereof is secured by the catheter housing device 1201, the catheter housing device 1201 can seal the insertion site.

Terminology

Certain terminology can be used in the following description for the purpose of reference only, and thus are not intended to be limiting. For example, terms such as "above" and "below" refer to directions in the drawings to which reference is made. Terms such as "proximal," "distal," "front," "back," "rear," and "side" describe the orientation and/or location of portions of the components or elements within a consistent but arbitrary frame of reference which is made clear by reference to the text and the associated drawings describing the components or elements under discussion. Such terminology can include the words specifically mentioned above, derivatives thereof, and words of similar import.

It should be emphasized that many variations and modifications can be made to the herein-described embodiments, the elements of which are to be understood as being among other acceptable examples. All such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein can be combined in different ways to form additional embodiments, all of which fall within the scope of the present disclosure.

Conditional language used herein, such as, among others, "can," "might," "can," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a" and "an" are to be construed to mean "one or more" or "at least one" unless specified otherwise.

Conjunctive language such as the phrase "at least one of X, Y and Z," unless specifically stated otherwise, is otherwise understood with the context as used in general to convey that an item, term, etc. can be either X, Y or Z. Thus, such conjunctive language is not generally intended to imply that certain embodiments require at least one of X, at least one of Y and at least one of Z to each be present.

What is claimed is:

1. A catheter housing device configured to be positioned atop a catheter insertion site on a subject, the catheter housing device comprising:
    a hub component comprising a membrane configured to secure to skin of the subject around the catheter insertion site when the catheter housing device is in use, wherein the membrane includes an opening configured to be positioned over the catheter insertion site;
    a cover configured to secure to the hub component and configured to at least partially enclose the catheter insertion site when the catheter housing device is in use, wherein the cover comprises an interior surface and an exterior surface;
    a catheter lock component configured to at least partially retain a catheter hub coupled to a catheter to reduce movement of the catheter when the catheter is inserted into the subject at the catheter insertion site; and
    at least one port extending outwardly from a portion of the exterior surface of the cover, wherein the at least one port is configured to allow gas to flow into an interior of the cover.

2. The catheter housing device of claim 1, wherein the membrane extends around an entirety of a perimeter of the cover when the cover is secured to the hub component.

3. The catheter housing device of claim 1, wherein the at least one port is configured to secure to a tube to allow gas flowing through the tube to flow into the interior of the cover.

4. The catheter housing device of claim 1, wherein the at least one port is configured to allow a sterilizing gas to flow into the interior of the cover.

5. The catheter housing device of claim 1, wherein the at least one port comprises a valve.

6. The catheter housing device of claim 1, wherein the at least one port comprises an at least partially cylindrical fluid passage.

7. The catheter housing device of claim 1, wherein a bottom surface of the membrane is configured to secure to the skin of the subject.

8. The catheter housing device of claim 1, wherein the hub component further comprises a main body connected to the membrane and configured to surround the catheter insertion site when the catheter housing device is in use, and wherein the cover is configured to secure to the main body.

9. The catheter housing device of claim 1, wherein the cover comprises one or more protrusions, each of the one or more protrusions configured to engage a portion of the hub component and secure the cover and the hub component to each other.

10. The catheter housing device of claim 1, wherein the catheter lock component and the hub component comprise a unitary structure that is removably securable to the cover.

11. The catheter housing device of claim 1, wherein the catheter housing device is configured to allow said gas to flow through said at least one port, into said interior, and toward the catheter insertion site when the catheter housing device is in use.

12. A catheter housing device configured to be positioned atop a catheter insertion site on a subject, the catheter housing device comprising:
   a hub component comprising a membrane configured to secure to skin of the subject around the catheter insertion site, wherein the membrane includes an opening configured to be positioned over the catheter insertion site when the membrane is secured to the skin around the catheter insertion site;
   a cover configured to at least partially enclose the catheter insertion site when the catheter housing device is in use, wherein the cover comprises an interior surface and an exterior surface; and
   at least one port extending outwardly from a portion of the exterior surface of the cover, wherein the at least one port is configured to allow gas to flow into an interior of the cover.

13. The catheter housing device of claim 12, wherein the cover is configured to secure to the hub component, and wherein the membrane extends around an entirety of a perimeter of the cover when the cover is secured to the hub component.

14. The catheter housing device of claim 12, wherein the at least one port is configured to allow a sterilizing gas to flow into the interior of the cover.

15. The catheter housing device of claim 12, wherein the at least one port is configured to secure to a tube to allow gas flowing through the tube to flow into the interior of the cover.

16. The catheter housing device of claim 12, wherein a bottom surface of the membrane is configured to secure to the skin of the subject.

17. The catheter housing device of claim 12, wherein the cover comprises one or more protrusions, each of the one or more protrusions configured to engage a portion of the hub component and secure the cover and the hub component to each other.

18. The catheter housing device of claim 12, wherein the catheter housing device is configured to allow said gas to flow through said at least one port, into said interior, and toward the catheter insertion site when the catheter housing device is in use.

19. A catheter housing device configured to be positioned atop a catheter insertion site on a subject, the catheter housing device comprising:
   a hub component comprising a membrane configured to secure to skin of the subject around the catheter insertion site, wherein the membrane includes an opening configured to be positioned over the catheter insertion site when the membrane is secured to the skin around the catheter insertion site;
   a cover configured to at least partially enclose the catheter insertion site when the catheter housing device is in use, wherein the cover comprises one or more protrusions, each of the one or more protrusions configured to engage a portion of the hub component and secure the cover and the hub component to each other; and
   at least one port extending outwardly from a portion of the cover, wherein the at least one port is configured to allow gas to flow into an interior of the cover.

20. A catheter housing device configured to be positioned atop a catheter insertion site on a subject, the catheter housing device comprising:
   a hub component comprising a membrane configured to secure to skin of the subject around the catheter insertion site when the catheter housing device is in use, wherein the membrane includes an opening configured to be positioned over the catheter insertion site;
   a cover configured to secure to the hub component and configured to at least partially enclose the catheter insertion site when the catheter housing device is in use;
   a catheter lock component configured to at least partially retain a catheter hub coupled to a catheter to reduce movement of the catheter when the catheter is inserted into the subject at the catheter insertion site, wherein the catheter lock component and the hub component comprise a unitary structure that is removably securable to the cover; and
   at least one port extending outwardly from a portion of the cover, wherein the at least one port is configured to allow gas to flow into an interior of the cover.

21. The catheter housing device of claim 20, wherein the hub component further comprises a main body connected to the membrane, and wherein the cover is configured to secure to the main body.

* * * * *